(12) United States Patent
Goertzen et al.

(10) Patent No.: US 10,799,281 B2
(45) Date of Patent: Oct. 13, 2020

(54) DETECTING IMPROPER ENERGY TRANSMISSION CONFIGURATION IN MEDICAL DEVICE SYSTEM

(71) Applicant: Kardium, Inc., Burnaby (CA)

(72) Inventors: Douglas Wayne Goertzen, New Westminster (CA); Daniel Martin Reinders, Richmond (CA); Daniel Robert Weinkam, Coquitlam (CA)

(73) Assignee: KARDIUM, INC., Burnaby (CA)

( * ) Notice: Subject to any disclaimer, the term of this patent is extended or adjusted under 35 U.S.C. 154(b) by 966 days.

(21) Appl. No.: 14/845,447

(22) Filed: Sep. 4, 2015

(65) Prior Publication Data

US 2015/0374427 A1 Dec. 31, 2015

Related U.S. Application Data

(63) Continuation of application No. PCT/US2014/024280, filed on Mar. 12, 2014.
(Continued)

(51) Int. Cl.
*A61B 18/14* (2006.01)
*A61B 18/12* (2006.01)
(Continued)

(52) U.S. Cl.
CPC ...... *A61B 18/1233* (2013.01); *A61B 18/1492* (2013.01); *A61B 34/20* (2016.02);
(Continued)

(58) Field of Classification Search
CPC .. A61B 2018/0022; A61B 2018/00267; A61B 2018/00351; A61B 2018/00904; A61B 18/1233

See application file for complete search history.

(56) References Cited

U.S. PATENT DOCUMENTS 5,357,956 A 10/1994 Nardella
5,562,720 A 10/1996 Stern et al.
(Continued)

FOREIGN PATENT DOCUMENTS

JP 2002065691 A 3/2002
WO 9848722 A1 11/1998
(Continued)

OTHER PUBLICATIONS

Office Action issued in copending U.S. Appl. No. 14/206,218 dated Jun. 29, 2018.
(Continued)

*Primary Examiner* — Michael F Peffley
*Assistant Examiner* — Bo Ouyang
(74) *Attorney, Agent, or Firm* — Rossi, Kimms & McDowell LLP

(57) ABSTRACT

A medical device system may be configured to detect an improper energy transmission configuration therein. The condition may be detected by way of a detection of a condition where an energy-transmitting electrode of the medical device system becomes too close to or becomes in contact with an object resulting in an inability of the electrode to properly transmit energy. For example, if the energy-transmitting electrode is a first electrode configured in its operational state to transmit energy to bodily tissue adjacent the first electrode, but the first electrode is inadvertently contacting a second electrode, such contact may cause at least some energy transmitted by the first electrode to follow an unintended path away from its intended path to the adjacent tissue. Such a condition may be detected based at least upon an analysis of information acquired from a sensing device system.

22 Claims, 16 Drawing Sheets

Related U.S. Application Data

(60) Provisional application No. 61/780,824, filed on Mar. 13, 2013.

(51) Int. Cl.
  *A61B 34/20* (2016.01)
  *A61B 18/00* (2006.01)
  *A61B 90/00* (2016.01)

(52) U.S. Cl.
  CPC .............. *A61B 2018/0016* (2013.01); *A61B 2018/00178* (2013.01); *A61B 2018/00267* (2013.01); *A61B 2018/00351* (2013.01); *A61B 2018/00577* (2013.01); *A61B 2018/00654* (2013.01); *A61B 2018/00791* (2013.01); *A61B 2018/00863* (2013.01); *A61B 2018/00875* (2013.01); *A61B 2018/00898* (2013.01); *A61B 2018/00988* (2013.01); *A61B 2090/065* (2016.02)

(56) References Cited

U.S. PATENT DOCUMENTS

| | | | |
|---|---|---|---|
| 5,575,810 A | | 11/1996 | Swanson et al. |
| 5,836,990 A | * | 11/1998 | Li .................... A61N 1/056 607/28 |
| 5,935,079 A | * | 8/1999 | Swanson ............. A61B 5/0422 600/374 |
| 5,944,022 A | | 8/1999 | Nardella et al. |
| 6,391,024 B1 | | 5/2002 | Sun et al. |
| 6,679,269 B2 | | 1/2004 | Swanson |
| 6,692,489 B1 | | 2/2004 | Heim et al. |
| 6,882,885 B2 | | 4/2005 | Levy, Jr. et al. |
| 7,172,591 B2 | | 2/2007 | Harano et al. |
| 7,251,531 B2 | | 7/2007 | Mosher et al. |
| 7,666,182 B2 | | 2/2010 | Klett et al. |
| 7,706,888 B2 | | 4/2010 | Jolly |
| 7,792,589 B2 | | 9/2010 | Levy, Jr. et al. |
| 7,824,400 B2 | | 11/2010 | Keppel |
| 8,160,690 B2 | | 4/2012 | Wilfley et al. |
| 8,696,656 B2 | | 4/2014 | Abboud et al. |
| 8,939,970 B2 | | 1/2015 | Stone et al. |
| 9,198,601 B2 | | 12/2015 | Hauck et al. |
| 2002/0115941 A1 | | 8/2002 | Whayne et al. |
| 2003/0028183 A1 | | 2/2003 | Sanchez et al. |
| 2006/0041253 A1 | | 2/2006 | Newton et al. |
| 2006/0106375 A1 | | 5/2006 | Werneth et al. |
| 2008/0009905 A1 | | 1/2008 | Zeijlemaker |
| 2009/0118729 A1 | * | 5/2009 | Auth .................. A61B 18/1492 606/42 |
| 2009/0125019 A1 | | 5/2009 | Douglass et al. |
| 2009/0131930 A1 | * | 5/2009 | Gelbart .............. A61B 18/1492 606/41 |
| 2011/0118727 A1 | | 5/2011 | Fish et al. |
| 2011/0313417 A1 | * | 12/2011 | De La Rama ..... A61B 18/1492 606/41 |
| 2012/0259327 A1 | | 10/2012 | Klimovitch et al. |
| 2013/0289551 A1 | * | 10/2013 | Condie .............. A61B 18/1233 606/33 |
| 2014/0276769 A1 | | 9/2014 | Goertzen et al. |

FOREIGN PATENT DOCUMENTS

| | | |
|---|---|---|
| WO | 2008049084 A2 | 4/2008 |
| WO | 2008082802 A2 | 7/2008 |
| WO | 2014/165062 A1 | 10/2014 |

OTHER PUBLICATIONS

Office Action issued in U.S. Appl. No. 14/206,218 dated Jan. 10, 2017.
International Search Report issued in PCT/US2014/024280 (Form PCT/ISA/210), dated Aug. 21, 2014.
Written Opinion issued in PCT/US2014/024280 (Form PCT/ISA/237), dated Aug. 21, 2014.
"Constellation Mapping Catheters", Brochure, Boston Scientific Corp., 2 pgs, © 2007 Boston Scientific Corporation.
"Phased RF Catheter Ablation System", 2014 Medtronic Inc., 2 pgs, http://www.medtronic.eu/your-health/atrial-fibrillation/about-the-therapy/our-phased-rf-ablation-system/[Jun. 24, 2014 2:38:05 PM].
"ThermoCool® Irrigated Tip Catheter", Brochure, Biosense Webster, 4 pgs, Biosense Webster, Inc. 3333 Diamond Canyon Road Diamond Bar, CA 91765, USA, © Biosense Webster, Inc. 2009 All rights reserved. 1109003.0.
Biotronik's "AlCath Flutter Gold Cath for Atrial Flutter Available in EU", Sep. 19, 2013, medGadget, 3 pgs, http://www.medgadget.com/2013/09/biotroniks-alcath-flutter-gold-cath-for-atrial-flutter-unveiled-in-europe.html [Jun. 24, 2014 2:37:09 PM].
Non-Final Office Action issued in U.S. Appl. No. 14/206,218 dated Mar. 24, 2016.
Extended European Search Report issued in European Appln. No. 14778054.8, dated Oct. 20, 2016.
Response to Office Action filed in U.S. Appl. No. 14/206,218 dated Sep. 16, 2016.
Office Action issued in U.S. Appl. No. 14/206,218 dated Nov. 30, 2017.
Office Action issued in European Application No. 14778054.8 dated Jun. 13, 2018.
Response filed in U.S. Appl. No. 14/206,218 dated Mar. 29, 2017.
Amendment filed in U.S. Appl. No. 14/206,218 dated Feb. 26, 2018.
Office Action issued in copending U.S. Appl. No. 14/206,218 dated Apr. 11, 2019.
Response to Office Action filed in U.S. Appl. No. 14/206,218 dated Aug. 28, 2018.
Response to Office Action filed in U.S. Appl. No. 14/206,218 dated Sep. 18, 2018.
Summons to Attend Oral Proceedings issued in European Application No. 14778054.8 mailed Feb. 20, 2019.
Pre-Appeal Brief Request for Review and Remarks to Accompany Request for Pre-Appeal Brief Review filed in copending U.S. Appl. No. 14/206,218 on Nov. 28, 2018.
Notice of Panel Decision from Pre-Appeal Brief Review issued in copending U.S. Appl. No. 14/206,218 mailed on Jan. 2, 2019.
Response filed in copending U.S. Appl. No. 14/206,218 dated Jun. 10, 2019.
Pre-Appeal Brief Request for Review and Remarks to Accompany Request for Pre-Appeal Brief Review filed in copending U.S. Appl. No. 14/206,218 on Aug. 15, 2019.
Notice of Panel Decision from Pre-Appeal Brief Review issued in copending U.S. Appl. No. 14/206,218 mailed on Sep. 26, 2019.
Intention to Grant issued in European Application No. 14778054.8 dated Sep. 26, 2019.
Office Action issued in copending U.S. Appl. No. 14/206,218 dated Feb. 24, 2020.
Response filed in copending U.S. Appl. No. 14/206,218 dated Apr. 17, 2020.

* cited by examiner

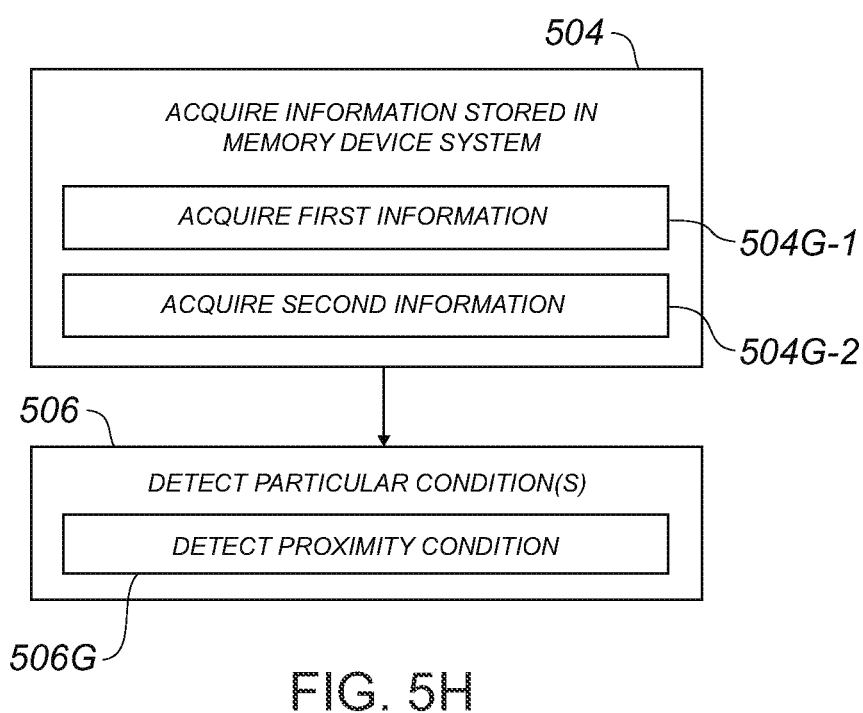

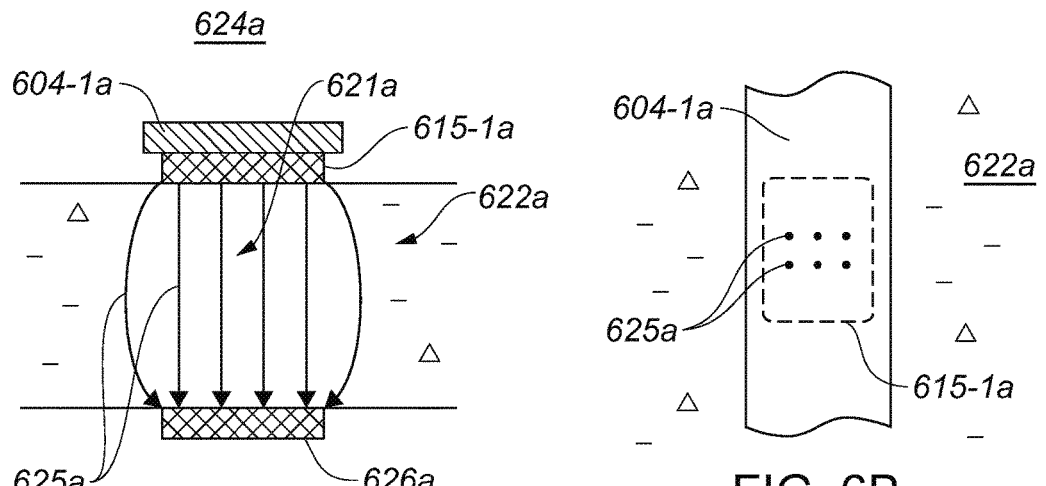
FIG. 6A
FIG. 6B
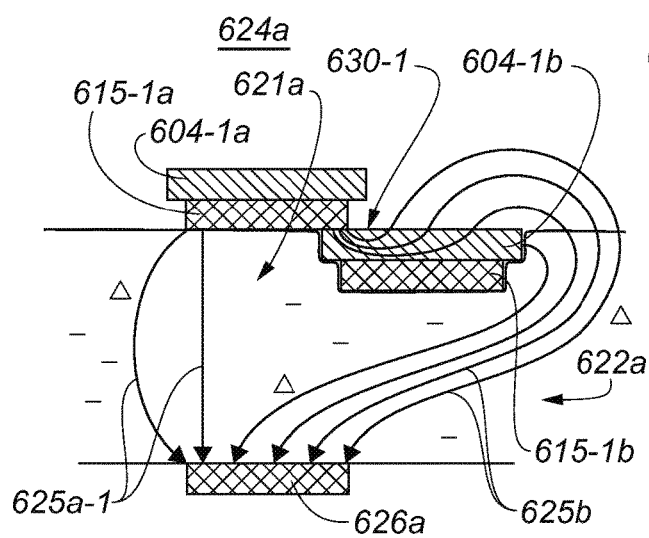
FIG. 6C
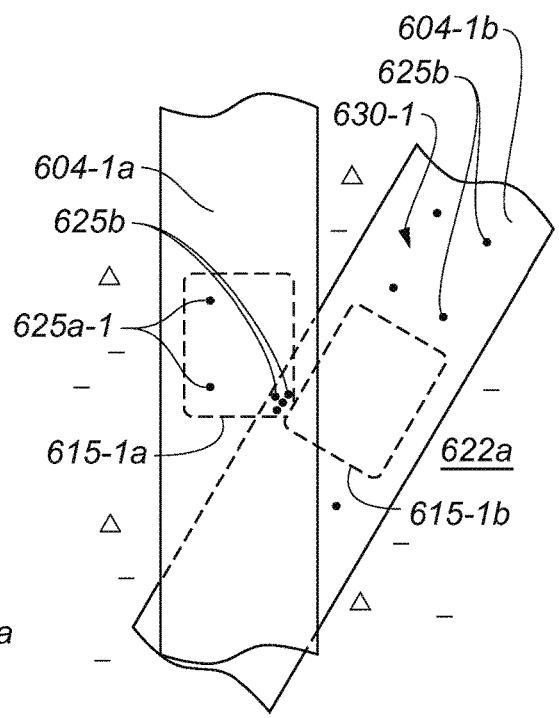
FIG. 6D

DETECTING IMPROPER ENERGY TRANSMISSION CONFIGURATION IN MEDICAL DEVICE SYSTEM

CROSS-REFERENCE TO RELATED APPLICATION

This application is a continuation of International Patent Application PCT/US2014/024280, filed Mar. 12, 2014, which claims priority benefit of U.S. Provisional Application No. 61/780,824, filed Mar. 13, 2013, the entire disclosure of each of these applications is hereby incorporated herein by reference.

TECHNICAL FIELD

Aspects of this disclosure generally are related to detecting one or more improper energy transmission configurations in systems in which successful energy transmission is a priority, such as, but not limited to, medical device systems where energy transmission may need to be properly controlled to successfully treat a patient or at least avoid unintended consequences.

BACKGROUND

Cardiac surgery was initially undertaken using highly invasive open procedures. A sternotomy, which is a type of incision in the center of the chest that separates the sternum was typically employed to allow access to the heart. In the past several decades, more and more cardiac operations are performed using intravascular or percutaneous techniques, where access to inner organs or other tissue is gained via a catheter.

Intravascular or percutaneous surgeries benefit patients by reducing surgery risk, complications and recovery time. However, the use of intravascular or percutaneous technologies also raises some particular challenges. Medical devices used in intravascular or percutaneous surgery need to be deployed via catheter systems which significantly increase the complexity of the device structure. As well, doctors do not have direct visual contact with the medical devices once the devices are positioned within the body.

One example of where intravascular or percutaneous medical techniques have been employed is in the treatment of a heart disorder called atrial fibrillation. Atrial fibrillation is a disorder in which spurious electrical signals cause an irregular heartbeat. Atrial fibrillation has been treated with open heart methods using a technique known as the "Cox-Maze procedure". During this procedure, physicians create specific patterns of lesions in the left and right atria to block various paths taken by the spurious electrical signals. Such lesions were originally created using incisions, but are now typically created by ablating the tissue with various techniques including radio-frequency (RF) energy, microwave energy, laser energy and cryogenic techniques. The procedure is performed with a high success rate under the direct vision that is provided in open procedures, but is relatively complex to perform intravascularly or percutaneously because of the difficulty in creating the lesions in the correct locations. Various problems, potentially leading to severe adverse results, may occur if the lesions are placed incorrectly. It is particularly important to know the position of the various transducers that may include electrodes operable for creating the lesions relative to cardiac features such as the pulmonary veins and mitral valve. The continuity, transmurality and placement of the lesion patterns that are formed can impact the ability to block paths taken within the heart by spurious electrical signals. Accordingly, it can be critically important to ensure that the lesion patterns are properly formed and placed.

In this regard, there is a need for techniques that ensure that lesions are properly formed and placed or ensure that improperly formed or placed lesions are prevented.

SUMMARY

At least the above-discussed need is addressed and technical solutions are achieved by various embodiments of the present invention. In some embodiments, device systems and methods executed by such systems exhibit enhanced capabilities for the detection of one or more improper energy transmission configurations in systems in which energy transmission is a priority, such as, but not limited to, medical device systems where energy transmission may need to be properly controlled to successfully treat a patient or at least avoid unintended consequences. In some embodiments, one or more positional deviations associated with one or more electrodes are detected, the one or more electrodes may be located within a bodily cavity such as an intra-cardiac cavity. In some embodiments, the suitability of one or more electrodes for tissue ablation, such as cardiac tissue ablation, is detected. In some embodiments, the system or systems, or a portion thereof, may be percutaneously or intravascularly delivered to position various electrodes within the bodily cavity. Various ones of the electrodes may be used to treat tissue within a bodily cavity. Treatment may include tissue ablation by way of non-limiting example. Various ones of the electrodes may be used to map tissue within the bodily cavity. Mapping can include mapping electrophysiological activity by way of non-limiting example. Mapping may be employed in a diagnosis of various conditions. Various ones of the electrodes may be used to stimulate tissue within the bodily cavity. Stimulation can include pacing by way of non-limiting example. Other characteristics and advantages will become apparent from the teaching herein to those of ordinary skill in the art.

In some embodiments, a medical device system medical system may be summarized as including a data processing device system and a memory device system communicatively connected to the data processing device system and storing a program executable by the data processing device system. The program includes acquisition instructions configured to cause an acquisition of information stored in the memory device system. The program includes detection instructions configured to cause a detection of a shunt condition created in an electric circuit based at least upon an analysis of the information acquired according to the acquisition instructions. The electric circuit includes at least a first electrode of one or more electrodes of an electrode-based device system that includes a structure and the one or more electrodes which are located on the structure. The one or more electrodes are positionable in a bodily cavity defined at least in part by a tissue wall. The shunt condition is associated with a diversion of a portion, but not all, of energy transmittable by the first electrode of the one or more electrodes away from a portion of adjacent tissue of the tissue wall, the adjacent tissue adjacent the first electrode of the one or more electrodes. The energy transmittable by the first electrode of the one or more electrodes is sufficient for tissue ablation. The program further includes storage instructions configured to cause a storage in the memory device system of detection information indicating the detection of the shunt condition according to the detection instructions.

The medical device system may further include an input-output device system communicatively connected to the data processing device system, the input-output device system including the electrode-based device system. The program may further include reception instructions configured to cause (a) a reception of first information at least from, via, by way of, utilizing, or by employing the electrode-based device system, and (b) a storage of the first information or a derivative thereof in the memory device system. The information acquired according to the acquisition instructions may be the first information or the derivative of the first information stored in the memory device system according to the reception instructions. The electrode-based device system may include one or more transducers, the one or more transducers configured to, while positioned in the bodily cavity, provide one or more electrical signals to the tissue wall. The first information or the derivative thereof may indicate a result of an interaction between the one or more electrical signals and the tissue wall, and the one or more electrical signals may include one or more energy levels insufficient for tissue ablation.

The medical device system may further include the electrode-based device system, which is communicatively connected to the data processing device system. The program may further include restriction instructions configured to cause a restriction of the energy transmittable by the first electrode of the one or more electrodes in response to the detected shunt condition. The shunt condition may be associated with a diversion of the portion of energy transmittable by the first electrode of the one or more electrodes from traveling along (a) a first electrical path extending from the first electrode of the one or more electrodes to the portion of the adjacent tissue of the tissue wall, to (b) a second electrical path extending from the first electrode of the one or more electrodes away from the portion of the adjacent tissue of the tissue wall. The shunt condition may be associated with a diversion of the portion of energy transmittable by the first electrode of the one or more electrodes to an electrically conductive portion of the structure. The shunt condition may be associated with a diversion of the portion of energy transmittable by the first electrode of the one or more electrodes to a metallic portion of the structure. The shunt condition may be associated with a diversion of the portion of energy transmittable by the first electrode of the one or more electrodes to a second electrode positionable in the bodily cavity. The one or more electrodes may include a second electrode, and the shunt condition may be associated with a diversion of the portion of energy transmittable by the first electrode of the one or more electrodes to the second electrode of the one or more electrodes. The shunt condition may be defined to occur at least due to contact between the first electrode of the one or more electrodes and a non-tissue based electrically conductive surface positionable in the bodily cavity. The non-tissue based electrically conductive surface may not form part of any electrode. The shunt condition may be defined to occur at least due to contact between the first electrode of the one or more electrodes and a metallic surface positionable in the bodily cavity. The shunt condition may be defined to occur at least due to contact between the first electrode of the one or more electrodes and an electrically conductive portion of the structure. The shunt condition may be defined to occur at least due to contact between the first electrode of the one or more electrodes and a second electrode positionable in the bodily cavity. The one or more electrodes may include a second electrode, and the shunt condition may be defined to occur at least due to contact between the first electrode of the one or more electrodes and the second electrode of the one or more electrodes.

The medical device system may further include an input-output device system communicatively connected to the data processing device system, and the program may further include failure state instructions configured to cause the input-output device system to present an error notification to a user in response to the detection of the shunt condition according to the detection instructions.

The information acquired according to the acquisition instructions may include impedance information associated with at least the first electrode of the one or more electrodes. The information acquired according to the acquisition instructions may include positional information indicative of a deviation in an expected positioning between the first electrode of the one or more electrodes and a physical portion of the electrode-based device system. The information acquired according to the acquisition instructions may include positional information indicative of a deviation in an expected positioning between a portion of the structure and the adjacent tissue of the tissue wall.

The medical device system may further include the electrode-based device system, which is communicatively connected to the data processing device system. The structure of the electrode-based device system may include a plurality of elongate members. The one or more electrodes may include a plurality of the electrodes, at least some of the plurality of the electrodes located on each of the plurality of elongate members. The first electrode of the one or more electrodes may be located on a first elongate member of the plurality of elongate members. The information acquired according to the acquisition instructions may include positional information indicative of a deviation in an expected positioning between the first electrode of the one or more electrodes and at least a second elongate member of the plurality of elongate members, the first elongate member being other than the second elongate member. The structure may be selectively moveable between a delivery configuration in which the structure is sized for percutaneous delivery to the bodily cavity and a deployed configuration in which the structure is sized too large for percutaneous delivery to the bodily cavity.

The medical device system may further include the electrode-based device system, which is communicatively connected to the data processing device system. The electric circuit may include a first electrical path extending at least from the first electrode of the one or more electrodes to a second electrode. The first electrical path may extend at least from the first electrode of the one or more electrodes to the second electrode via at least the portion of the adjacent tissue. The shunt condition may be associated with a diversion of the portion of energy transmittable by the first electrode from the first electrical path to a second electrical path other than the first electrical path, the second electrical path extending from the first electrode of the one or more electrodes to the second electrode. The second electrical path may extend from the first electrode of the one or more electrodes to the second electrode via tissue of the tissue wall other than the portion of the adjacent tissue. The second electrode may be an indifferent electrode positioned outside of the bodily cavity. The second electrode may be positionable in the bodily cavity. The one or more electrodes may include the second electrode.

The shunt condition may be associated with a smaller portion of the energy transmittable by the first electrode of the one or more electrodes being receivable by the portion of the adjacent tissue as compared to an unshunted condition. In some embodiments, the shunt condition is associated with a larger portion of the energy transmittable by the first electrode of the one or more electrodes being receivable by tissue of the tissue wall other than the portion of the adjacent tissue as compared to an unshunted condition. The shunt condition may be associated with an increase in the diversion of the portion of the energy transmittable by the first electrode of the one or more electrodes.

The medical device system may further include an input-output device system communicatively connected to the data processing device system, the input-output device system including a sensing device system. The program may further include reception instructions configured to cause (a) a reception of first information at least from, via, by way of, utilizing, or by employing the sensing device system, and (b) a storage of the first information or a derivative thereof in the memory device system, and the information acquired according to the acquisition instructions may be the first information or the derivative of the first information stored in the memory device system according to the reception instructions.

In some embodiments, various systems may include combinations and subsets of the systems summarized above.

In some embodiments, a medical device system may be summarized as including a data processing device system and a memory device system communicatively connected to the data processing device system and storing a program executable by the data processing device system. The data processing device system is configured by the program at least to acquire information stored in the memory device system and detect a shunt condition created in an electric circuit based at least upon an analysis of the acquired information. The electric circuit includes at least a first electrode of one or more electrodes of an electrode-based device system that includes a structure and the one or more electrodes located on the structure, the one or more electrodes positionable in a bodily cavity defined at least in part by a tissue wall. The shunt condition is associated with a diversion of a portion, but not all, of energy transmittable by the first electrode of the one or more electrodes away from a portion of adjacent tissue of the tissue wall, the adjacent tissue adjacent the first electrode of the one or more electrodes, and the energy transmittable by the first electrode of the one or more electrodes sufficient for tissue ablation. The data processing device system is configured by the program to store, in the memory device system, detection information indicating the detection of the shunt condition.

In some embodiments, a method is executed by a data processing device system according to a program stored by a memory device system communicatively connected to the data processing device system. The method may be summarized as including acquiring information stored in the memory device system and detecting a shunt condition created in an electric circuit based at least upon an analysis of the acquired information. The electric circuit includes at least a first electrode of one or more electrodes of an electrode-based device system that includes a structure and the one or more electrodes located on the structure, the one or more electrodes positionable in a bodily cavity defined at least in part by a tissue wall. The shunt condition is associated with a diversion of a portion, but not all, of energy transmittable by the first electrode of the one or more electrodes away from a portion of adjacent tissue of the tissue wall, the adjacent tissue adjacent the first electrode of the one or more electrodes. The energy transmittable by the first electrode of the one or more electrodes is sufficient for tissue ablation. The method further includes storing, in the memory device system, detection information indicating the detection of the shunt condition.

In some embodiments, a computer-readable storage medium system may be summarized as including one or more computer-readable storage mediums storing a program executable by one or more data processing devices of a data processing device system. The program includes an acquisition module configured to cause an acquisition of information stored in a memory device system and a detection module configured to cause a detection of a shunt condition created in an electric circuit based at least upon an analysis of the information acquired according to the acquisition instructions. The electric circuit includes at least a first electrode of one or more electrodes of an electrode-based device system that includes a structure and the one or more electrodes located on the structure, the one or more electrodes positionable in a bodily cavity defined at least in part by a tissue wall. The shunt condition is associated with a diversion of a portion, but not all, of energy transmittable by the first electrode of the one or more electrodes away from a portion of adjacent tissue of the tissue wall, the adjacent tissue adjacent the first electrode of the one or more electrodes. The energy transmittable by the first electrode of the one or more electrodes is sufficient for tissue ablation. The program further includes a storage module configured to cause a storage in the memory device system of detection information indicating the detection of the shunt condition according to the detection module. In some embodiments, the computer-readable storage medium system is a non-transitory computer-readable storage medium system that includes one or more non-transitory computer-readable storage mediums.

In some embodiments, a medical device may be summarized as including a data processing device system and a memory device system communicatively connected to the data processing device system and storing a program executable by the data processing device system. The program includes acquisition instructions configured to cause an acquisition of information stored in the memory device system. The program includes detection instructions configured to cause a detection of a shunt condition based at least upon an analysis of the information acquired according to the acquisition instructions. The shunt condition is associated with a diversion of a portion of energy transmittable by at least a first electrode of a plurality of electrodes of an electrode-based device system that includes a structure on which each of the plurality of electrodes is located. The plurality of electrodes are positionable in a bodily cavity. The structure is selectively movable between a delivery configuration in which the structure is sized for percutaneous delivery to the bodily cavity and a deployed configuration in which the structure is sized too large for percutaneous delivery to the bodily cavity. The program further includes determination instructions configured to cause a determination of, at least in response to the detected shunt condition, a deviation in an expected positioning between the first electrode of the plurality of electrodes and a physical portion of the electrode-based device system at least when the structure is in the deployed configuration, and storage instructions configured to cause a storage in the memory device system of determination information indicating a result of the determination of the deviation according to the determination instructions.

The medical device system may further include the electrode-based device system, which is communicatively connected to the data processing device system.

The program may include restriction instructions configured to cause a restriction of the energy transmittable by at least the first electrode of the plurality of electrodes in response to the detected shunt condition. In some embodiments, the program may include restriction instructions configured to prevent initiation of transmission of the energy transmittable by at least the first electrode of the plurality of electrodes in response to the detected shunt condition.

The medical device system may further include an input-output device system communicatively connected to the data processing device system, the input-output device system including the electrode-based device system. The program may further include reception instructions configured to cause (a) a reception of first information at least from, via, by way of, utilizing, or by employing the electrode-based device system, and (b) a storage of the first information or a derivative thereof in the memory device system, and the information acquired according to the acquisition instructions may be the first information or the derivative of the first information stored in the memory device system according to the reception instructions.

The medical device system may further include an input-output device system communicatively connected to the data processing device system, the input-output device system including a sensing device system. The program may further include reception instructions configured to cause (a) a reception of first information at least from, via, by way of, utilizing, or by employing the sensing device system, and (b) a storage of the first information or a derivative thereof in the memory device system, and the information acquired according to the acquisition instructions may be the first information or the derivative of the first information stored in the memory device system according to the reception instructions.

The bodily cavity is defined at least in part by a tissue wall, and the shunt condition may be associated with a diversion of the portion of transmittable energy from traveling (a) along a first electrical path extending from the first electrode of the plurality of electrodes to a portion of adjacent tissue of the tissue wall to (b) a second electrical path extending from the first electrode of the plurality of electrodes away from the portion of the adjacent tissue of the tissue wall, the adjacent tissue adjacent the first electrode of the plurality of electrodes.

The medical device system may further include the electrode-based device system, which is communicatively connected to the data processing device system. The shunt condition may be associated with a diversion of the portion of energy transmittable by the first electrode of the plurality of electrodes to an electrically conductive portion of the structure. The shunt condition may be associated with a diversion of the portion of energy transmittable by the first electrode of the plurality of electrodes to a metallic portion of the structure. The shunt condition may be associated with a diversion of the portion of energy transmittable by the first electrode of the plurality of electrodes to a second electrode positionable in the bodily cavity, the diversion to the physical portion of the electrode-based device system. The plurality of electrodes may include a second electrode, and the shunt condition may be associated with a diversion of the portion of energy transmittable by the first electrode of the plurality of electrodes to the second electrode of the plurality of electrodes, the diversion to the physical portion of the electrode-based device system. The shunt condition may be associated with contact between the first electrode of the plurality of electrodes and a non-tissue based electrically conductive surface positionable in the bodily cavity. The non-tissue based electrically conductive surface may not form part of any electrode.

The information acquired according to the acquisition instructions may include impedance information associated with at least the first electrode of the plurality of electrodes.

The medical device system may further include an input-output device system communicatively connected to the data processing device system, the input-output device system including the electrode-based device system. The program may further include reception instructions configured to cause (a) a reception of first information at least from, via, by way of, utilizing, or by employing the electrode-based device system, and (b) a storage of the first information or a derivative thereof in the memory device system, and the information acquired according to the acquisition instructions may be the first information or the derivative of the first information stored in the memory device system according to the reception instructions. The bodily cavity is defined at least part by a tissue wall, and the electrode-based device system may include one or more transducers, the one or more transducers configured to, while positioned in the bodily cavity, provide one or more electrical signals to the tissue wall. The first information or the derivative thereof may indicate a result of an interaction between the one or more electrical signals and the tissue wall. The one or more electrical signals may include one or more energy levels insufficient for tissue ablation. In some embodiments, the program includes restriction instructions configured to cause a restriction of the energy transmittable by at least the first electrode of the plurality of electrodes in response to the detected shunt condition. In some embodiments, the program includes restriction instructions configured to prevent initiation of transmission of the energy transmittable by at least the first electrode of the plurality of electrodes in response to the detected shunt condition.

The medical device system may further include the electrode-based device system, which is communicatively connected to the data processing device system. The shunt condition may be associated with at least a portion of the first electrode being overlapped by a structural member of the structure at least when the structure is in the deployed configuration. The structure may include one or more elongate members, at least some of the plurality of the electrodes located on each of the one or more elongate members. The shunt condition may be associated with at least a portion of the first electrode being overlapped by an elongate member of the one or more elongate members at least when the structure is in the deployed configuration. The structure may include a plurality of elongate members, the first electrode located on a first elongate member of the plurality of elongate members. The shunt condition may be associated with at least a portion of the first electrode being overlapped by an elongate member of the plurality of elongate members other than the first elongate member at least when the structure is in the deployed configuration. In some embodiments, the physical portion of the electrode-based device system is a portion of the structure. In some embodiments, the physical portion of the electrode-based device system is a second electrode. The plurality of electrodes may include the second electrode. The physical portion of the electrode-based device system is positionable in the bodily cavity in some embodiments.

In some embodiments, various systems may include combinations and subsets of the systems summarized above.

In some embodiments, a medical device system may be summarized as including a data processing device system and a memory device system communicatively connected to the data processing device system and storing a program executable by the data processing device system. The data processing device system is configured by the program at least to acquire information stored in the memory device system and detect a shunt condition based at least upon an analysis of the acquired information. The shunt condition is associated with a diversion of a portion of energy transmittable by at least a first electrode of a plurality of electrodes of an electrode-based device system that includes a structure on which each of the plurality of electrodes is located, the plurality of electrodes positionable in a bodily cavity. The structure is selectively movable between a delivery configuration in which the structure is sized for percutaneous delivery to the bodily cavity and a deployed configuration in which the structure is sized too large for percutaneous delivery to the bodily cavity. The data processing device system is further configured by the program to determine, at least in response to the detected shunt condition, a deviation in an expected positioning between the first electrode of the plurality of electrodes and a physical portion of the electrode-based device at least when the structure is in the deployed configuration; and store, in the memory device system, determination information indicating a result of the determination of the deviation.

In some embodiments, a method is executed by a data processing device system according to a program stored by a memory device system communicatively connected to the data processing device system. The method may be summarized as including acquiring information stored in the memory device system and detecting a shunt condition based at least upon an analysis of the acquired information. The shunt condition is associated with a diversion of a portion of energy transmittable by at least a first electrode of a plurality of electrodes of an electrode-based device system that includes a structure on which each of the plurality of electrodes is located, the plurality of electrodes positionable in a bodily cavity. The structure is selectively movable between a delivery configuration in which the structure is sized for percutaneous delivery to the bodily cavity and a deployed configuration in which the structure is sized too large for percutaneous delivery to the bodily cavity. The method further includes determining, at least in response to the detected shunt condition, a deviation in an expected positioning between the first electrode of the plurality of electrodes and a physical portion of the electrode-based device at least when the structure is in the deployed configuration, and storing, in the memory device system, determination information indicating a result of the determination of the deviation.

In some embodiments, a computer-readable storage medium system may be summarized as including one or more computer-readable storage mediums storing a program executable by one or more data processing devices of a data processing device system. The program includes an acquisition module configured to cause an acquisition of information stored in a memory device system and a detection module configured to cause a detection of a shunt condition based at least upon an analysis of the information acquired according to the acquisition module. The shunt condition is associated with a diversion of a portion of energy transmittable by at least a first electrode of a plurality of electrodes of an electrode-based device system that includes a structure on which each of the plurality of electrodes is located, the plurality of electrodes positionable in a bodily cavity. The structure is selectively movable between a delivery configuration in which the structure is sized for percutaneous delivery to the bodily cavity and a deployed configuration in which the structure is sized too large for percutaneous delivery to the bodily cavity. The program further includes a determination module configured to cause a determination of, at least in response to the detected shunt condition, a deviation in an expected positioning between the first electrode of the plurality of electrodes and a physical portion of the electrode-based device at least when the structure is in the deployed configuration, and a storage module configured to cause a storage in the memory device system of determination information indicating a result of the determination of the deviation according to the determination module. In some embodiments, the computer-readable storage medium system is a non-transitory computer-readable storage medium system that includes one or more non-transitory computer-readable storage mediums.

In some embodiments, a medical device system may be summarized as including a data processing device system and a memory device system communicatively connected to the data processing device system and storing a program executable by the data processing device system. The program includes acquisition instructions configured to cause an acquisition of information stored in the memory device system. The program includes detection instructions configured to cause a detection of a condition, based at least upon an analysis of the information acquired according to the acquisition instructions. The condition indicates that some, but not all, of a respective electrically conductive surface portion of each of at least a first electrode of one or more electrodes is available to contact tissue of a tissue wall of a bodily cavity when a structure, on which each of the one or more electrodes is located, is positioned in the bodily cavity in a deployed configuration, the deployed configuration being different than a delivery configuration in which the structure is sized for percutaneous delivery to the bodily cavity. The entirety of the respective electrically conductive surface portion of each of at least the first electrode of the one or more electrodes is configured, in absence of the condition, to contact a contiguous surface portion of the tissue wall when the structure is positioned in the bodily cavity in the deployed configuration. For each respective electrically conductive surface portion, energy is transmittable between the respective electrically conductive surface portion and the tissue wall, the energy sufficient for tissue ablation. The program further includes storage instructions configured to cause a storage in the memory device system of detection information indicating the detection of the condition according to the detection instructions.

The medical device system may further include an electrode-based device system communicatively connected to the data processing device system, the electrode-based device system including the structure and the one or more electrodes located on the structure, the structure selectively movable between the delivery configuration and the deployed configuration.

The medical device system may further include an input-output device system communicatively connected to the data processing device system, the input-output device system including the electrode-based device system. The program may further include reception instructions configured to cause (a) a reception of first information at least from, via, by way of, utilizing, or by employing the electrode-based device system, and (b) a storage of the first information or a derivative thereof in the memory device system, and the information acquired according to the acquisition instructions may be the first information or the derivative of the first information stored in the memory device system according to the reception instructions.

The medical device system may further include an input-output device system communicatively connected to the data processing device system, the input-output device system including a sensing device system. The program may further include reception instructions configured to cause (a) a reception of first information at least from, via, by way of, utilizing, or by employing the sensing device system, and (b) a storage of the first information or a derivative thereof in the memory device system, and the information acquired according to the acquisition instructions may be the first information or the derivative of the first information stored in the memory device system according to the reception instructions.

The program may include restriction instructions configured to cause a restriction of the energy transmittable by at least the first electrode of the one or more electrodes in response to the detected condition. In some embodiments, the program includes restriction instructions configured to prevent initiation of transmission of the energy transmittable by at least the first electrode of the plurality of electrodes in response to the detected condition. The medical device system may further include an input-output device system communicatively connected to the data processing device system and the program may further include failure state instructions configured to cause the input-output device system to present an error notification to a user in response to the detection of the condition according to the detection instructions.

The medical device system may further include an electrode-based device system communicatively connected to the data processing device system, the electrode-based device system including the structure and the one or more electrodes located on the structure, the structure selectively movable between the delivery configuration and the deployed configuration. The condition may be associated with contact between a non-tissue based surface positioned in the bodily cavity and the electrically conductive surface portion of the first electrode of the one or more electrodes when the structure is positioned in the bodily cavity in the deployed configuration. In some embodiments, the non-tissue based surface does not form part of any electrode. The condition may be associated with contact between the electrically conductive surface portion of the first electrode of the one or more electrodes and a portion of the structure when the structure is positioned in the bodily cavity in the deployed configuration. The condition may be associated with contact between a second electrode positioned in the bodily cavity and the electrically conductive surface portion of the first electrode of the one or more electrodes when the structure is positioned in the bodily cavity in the deployed configuration. The one or more electrodes may include a second electrode, and the condition may be associated with contact between the electrically conductive surface portion of the first electrode of the one or more electrodes and the second electrode of the one or more electrodes when the structure is positioned in the bodily cavity in the deployed configuration. At least part of the electrically conductive surface portion of the first electrode of the one or more electrodes may be outward facing, e.g., positioned to face outward or towards an adjacent surface portion of the tissue wall when the structure is positioned in the bodily cavity in the deployed configuration, and the condition may be associated with a positioning of a physical portion of the electrode-based device system between the electrically conductive surface portion of the first electrode of the one or more electrodes and the surface portion of the tissue wall when the structure is positioned in the bodily cavity in the deployed configuration. At least part of the electrically conductive surface portion of the first electrode of the one or more electrodes may be outward facing, e.g., positioned to face outward or towards an adjacent surface portion of the tissue wall when the structure is positioned in the bodily cavity in the deployed configuration, and the condition may be associated with a positioning of a portion of the structure between the electrically conductive surface portion of the first electrode of the one or more electrodes and the surface portion of the tissue wall when the structure is positioned in the bodily cavity in the deployed configuration.

The information acquired according to the acquisition instructions may include impedance information associated with at least the first electrode of the one or more electrodes. The medical device system may further include an electrode-based device system communicatively connected to the data processing device system, the electrode-based device system including the structure and the one or more electrodes located on the structure, the structure selectively movable between the delivery configuration and the deployed configuration. The information acquired according to the acquisition instructions may include positional information indicative of a deviation in an expected positioning between the first electrode of the one or more electrodes and a physical portion of the electrode-based device system when the structure is positioned in the bodily cavity in the deployed configuration. The electrode-based device system may include one or more transducers, the one or more transducers configured to, while positioned in the bodily cavity, provide one or more electrical signals to the tissue wall, and the first information or the derivative thereof may indicate a result of an interaction between the one or more electrical signals and the tissue wall. The one or more electrical signals may include one or more energy levels insufficient for tissue ablation. The structure may include one or more elongate members and the one or more electrodes may include a plurality of the electrodes, at least some of the plurality of the electrodes located on each of the one or more elongate members. The first electrode of the one or more electrodes may be located on a first elongate member of the one or more elongate members, and the information acquired according to the acquisition instructions may include positional information indicative of a deviation in an expected positioning between the first electrode of the one or more electrodes and an elongate member of the one or more elongate members when the structure is positioned in the bodily cavity in the deployed configuration. The structure may include a plurality of elongate members, and the one or more electrodes may include a plurality of the electrodes, at least some of the plurality of the electrodes located on each of the plurality of elongate members. The first electrode of the one or more electrodes may be located on a first elongate member of the plurality of elongate members, and the information acquired according to the acquisition instructions may include positional information indicative of a deviation in an expected positioning between the first electrode of the one or more electrodes and at least a second elongate member of the plurality of elongate members when the structure is positioned in the bodily cavity in the deployed configuration, the first elongate member being other than the second elongate member. The structure may include a plurality of elongate members, each of the elongate members including a proximal end, a distal end, an intermediate portion positioned between the proximal end and the distal end, and a thickness, each intermediate portion including a front surface and a back surface opposite across the thickness of the elongate member from the front surface. The one or more electrodes may include a plurality of the electrodes, at least some of the plurality of the electrodes located on each of the respective front surfaces of the plurality of elongate members. The first electrode of the one or more electrodes may be located on the respective front surface of a first elongate member of the plurality of elongate members, and the information acquired according to the acquisition instructions may include positional information indicative of positioning where at least part of the electrically conductive surface portion of the first electrode of the one or more electrodes faces the respective back surface of a second elongate member of the plurality of elongate members when the structure is positioned in the bodily cavity in the deployed configuration, the first elongate member being other than the second elongate member.

In some embodiments, the structure is sized too large for percutaneous delivery to the bodily cavity when the structure is in the deployed configuration.

In some embodiments, various systems may include combinations and subsets of the systems summarized above.

In some embodiments, a medical device system may be summarized as including a data processing device system and a memory device system communicatively connected to the data processing device system and storing a program executable by the data processing device system. The data processing device system is configured by the program at least to acquire information stored in the memory device system and detect a condition, based at least upon an analysis of the acquired information. The condition indicates that some, but not all, of a respective electrically conductive surface portion of each of at least a first electrode of one or more electrodes is available to contact tissue of a tissue wall of a bodily cavity when a structure, on which each of the one or more electrodes is located, is positioned in the bodily cavity in a deployed configuration, the deployed configuration being different than a delivery configuration in which the structure is sized for percutaneous delivery to the bodily cavity. The entirety of the respective electrically conductive surface portion of each of at least the first electrode of the one or more electrodes is configured, in absence of the condition, to contact a contiguous surface portion of the tissue wall when the structure is positioned in the bodily cavity in the deployed configuration. For each respective electrically conductive surface portion, energy is transmittable between the respective electrically conductive surface portion and the tissue wall, the energy sufficient for tissue ablation. The data processing device system is further configured by the program to store, in the memory device system, detection information indicating the detection of the condition.

In some embodiments, a method is executed by a data processing device system according to a program stored by a memory device system communicatively connected to the data processing device system. The method may be summarized as including acquiring information stored in the memory device system and detecting a condition, based at least upon an analysis of the acquired information. The condition indicates that some, but not all, of a respective electrically conductive surface portion of each of at least a first electrode of one or more electrodes is available to contact tissue of a tissue wall of a bodily cavity when a structure, on which each of the one or more electrodes is located, is positioned in the bodily cavity in a deployed configuration, the deployed configuration being different than a delivery configuration in which the structure is sized for percutaneous delivery to the bodily cavity. The entirety of the respective electrically conductive surface portion of each of at least the first electrode of the one or more electrodes is configured, in absence of the condition, to contact a contiguous surface portion of the tissue wall when the structure is positioned in the bodily cavity in the deployed configuration, and for each respective electrically conductive surface portion, energy is transmittable between the respective electrically conductive surface portion and the tissue wall, the energy sufficient for tissue ablation. The method further includes storing, in the memory device system, detection information indicating the detection of the condition.

In some embodiments, a computer-readable storage medium system may be summarized as including one or more computer-readable storage mediums storing a program executable by one or more data processing devices of a data processing device system. The program includes an acquisition module configured to cause an acquisition of information stored in a memory device system and a detection module configured to cause a detection of a condition, based at least upon an analysis of the information acquired according to the acquisition module. The condition indicates that some, but not all, of a respective electrically conductive surface portion of each of at least a first electrode of one or more electrodes is available to contact tissue of a tissue wall of a bodily cavity when a structure, on which each of the one or more electrodes is located, is positioned in the bodily cavity in a deployed configuration, the deployed configuration being different than a delivery configuration in which the structure is sized for percutaneous delivery to the bodily cavity. The entirety of the respective electrically conductive surface portion of each of at least the first electrode of the one or more electrodes is configured, in absence of the condition, to contact a contiguous surface portion of the tissue wall when the structure is positioned in the bodily cavity in the deployed configuration, and for each respective electrically conductive surface portion, energy is transmittable between the respective electrically conductive surface portion and the tissue wall, the energy sufficient for tissue ablation. The program further includes a storage module configured to cause a storage in the memory device system of detection information indicating the detection of the condition according to the detection module. In some embodiments, the computer-readable storage medium system is a non-transitory computer-readable storage medium system that includes one or more non-transitory computer-readable storage mediums.

In some embodiments, a medical device system may be summarized as including a data processing device system and a memory device system communicatively connected to the data processing device system and storing a program executable by the data processing device system. The program includes acquisition instructions configured to cause an acquisition of information stored in the memory device system and detection instructions configured to cause a detection of a condition, based at least upon an analysis of the information acquired according to the acquisition instructions. The condition indicates that a distance between a first non-tissue based electrically conductive surface positioned in a bodily cavity and a first electrode located on a structure positioned in the bodily cavity in a deployed configuration is less than a target distance between the first non-tissue based electrically conductive surface and the first electrode when the structure is in the deployed configuration, the deployed configuration being different than a delivery configuration in which the structure is sized for percutaneous delivery to the bodily cavity. When the structure is positioned in the bodily cavity in the deployed configuration, energy sufficient for tissue ablation is transmittable by the first electrode, at least some of the energy transmittable to adjacent tissue of a tissue wall of the bodily cavity. The program further includes storage instructions configured to cause a storage in the memory device system of detection information indicating the detection of the condition according to the detection instructions.

In some embodiments, the medical device system further includes an electrode-based device system that includes the first electrode and the structure. In some embodiments, the medical device system includes the first non-tissue based electrically conductive surface.

The medical device system may further include an input-output device system communicatively connected to the data processing device system, the input-output device system including a sensing device system. The program may further include reception instructions configured to cause (a) a reception of first information at least from, via, by way of, utilizing, or by employing the sensing device system, and (b) a storage of the first information or a derivative thereof in the memory device system, and the information acquired according to the acquisition instructions may be the first information or the derivative of the first information stored in the memory device system according to the reception instructions.

The medical device system may further include an input-output device system communicatively connected to the data processing device system, the input-output device system including an electrode-based device system that that includes the first electrode and the structure. The program may further include reception instructions configured to cause (a) a reception of first information at least from, via, by way of, utilizing, or by employing the electrode-based device system, and (b) a storage of the first information or a derivative thereof in the memory device system, and the information acquired according to the acquisition instructions may be the first information or the derivative of the first information stored in the memory device system according to the reception instructions. The electrode-based device system may include one or more transducers, the one or more transducers configured to, while positioned in the bodily cavity, provide one or more electrical signals to the tissue wall. The first information or the derivative thereof may indicate a result of an interaction between the one or more electrical signals and the tissue wall, and the one or more electrical signals may include one or more energy levels insufficient for tissue ablation. In some embodiments, the first information or the derivative thereof is indicative of an electrical impedance between the first electrode and a second non-tissue based electrically conductive surface other than the first non-tissue based electrically conductive surface, the electrical impedance being lower than a target electrical impedance between the first electrode and the second non-tissue based electrically conductive surface. The target electrical impedance may be associated with an occurrence in which the first electrode and the first non-tissue based electrically conductive surface are spaced with respect to one another by the target distance when the structure is in the deployed configuration. In some embodiments, the first non-tissue based electrically conductive surface is part of a portion of the structure, and the second non-tissue based electrically conductive surface is part of a second electrode other than the first electrode. The second electrode may be an indifferent electrode configured to be positioned outside of the bodily cavity. The second electrode may be located on the structure.

In some embodiments, the first non-tissue based electrically conductive surface is part of a second electrode other than the first electrode. The second electrode may be located on the structure. The second non-tissue based electrically conductive surface may be part of an indifferent electrode configured to be positioned outside of the bodily cavity. The second non-tissue based electrically conductive surface may be part of a non-electrode portion of the structure. The second non-tissue based electrically conductive surface may be part of a third electrode located on the structure, the third electrode being other than each of the first electrode and the second electrode.

In some embodiments, the structure includes a plurality of elongate members, and electrode-based device system includes a plurality of electrodes that include the first electrode, at least some of the plurality of the electrodes located on each of the plurality of elongate members. The first electrode may be located on a first elongate member of the plurality of elongate members, and the first non-tissue based electrically conductive surface may be part of a second elongate member of the plurality of elongate members, the second elongate member being other than the first elongate member. In some embodiments, the structure includes one or more elongate members, and the electrode-based device system includes a plurality of electrodes that include the first electrode, at least some of the plurality of the electrodes located on each of the one or more elongate members. The first electrode may be located on a first elongate member of the one or more elongate members, and the first non-tissue based electrically conductive surface may be part of a second electrode of the plurality of electrodes, the second electrode located on an elongate member of the one or more elongate members, the second electrode being other than the first electrode. The second non-tissue based electrically conductive surface may be part of an indifferent electrode configured to be positioned outside of the bodily cavity.

The bodily cavity may be an intra-cardiac cavity, and at least some of the energy being transmittable to blood in the intra-cardiac cavity. The target distance may be determined to be sufficient to limit the at least some of the energy transmittable to the blood to have a magnitude insufficient for thermal coagulation of the blood.

The program may include restriction instructions configured to cause a restriction of the energy transmittable by at least the first electrode in response to the detected condition. In some embodiments, the program includes restriction instructions configured to prevent initiation of transmission of the energy transmittable by at least the first electrode in response to the detected condition. The medical device system may further include an input-output device system communicatively connected to the data processing device system, and the program may further include failure state instructions configured to cause the input-output device system to present an error notification to a user in response to the detection of the condition according to the detection instructions. In some embodiments, the structure is sized too large for percutaneous delivery to the bodily cavity when the structure is in the deployed configuration.

In some embodiments, various systems may include combinations and subsets of the systems summarized above.

In some embodiments, a medical device system may be summarized as including a data processing device system and a memory device system communicatively connected to the data processing device system and storing a program executable by the data processing device system. The processing device system is configured by the program at least to acquire information stored in the memory device system and detect a condition, based at least upon an analysis of the acquired information. The condition indicates that a distance between a first non-tissue based electrically conductive surface positionable in a bodily cavity and a first electrode located on a structure positionable in the bodily cavity in a deployed configuration is less than a target distance between the first non-tissue based electrically conductive surface and the first electrode when the structure is in the deployed configuration, the deployed configuration being different than a delivery configuration in which the structure is sized for percutaneous delivery to the bodily cavity. When the structure is positioned in the bodily cavity in the deployed configuration, energy sufficient for tissue ablation is transmittable by the first electrode, at least some of the energy transmittable to adjacent tissue of a tissue wall of the bodily cavity. The processing device system is further configured by the program to store, in the memory device system, detection information indicating the detection of the condition.

In some embodiments, a method is executed by a data processing device system according to a program stored by a memory device system communicatively connected to the data processing device system. The method may be summarized as including acquiring information stored in the memory device system and detecting a condition, based at least upon an analysis of the acquired information. The condition indicates that a distance between a first non-tissue based electrically conductive surface positioned in a bodily cavity and a first electrode located on a structure positioned in the bodily cavity in a deployed configuration is less than a target distance between the first non-tissue based electrically conductive surface and the first electrode when the structure is in the deployed configuration, the deployed configuration being different than a delivery configuration in which the structure is sized for percutaneous delivery to the bodily cavity. When the structure is positioned in the bodily cavity in the deployed configuration, energy sufficient for tissue ablation is transmittable by the first electrode, at least some of the energy transmittable to adjacent tissue of a tissue wall of the bodily cavity. The method further includes storing, in the memory device system, detection information indicating the detection of the condition.

In some embodiments, a computer-readable storage medium system may be summarized as including one or more computer-readable storage mediums storing a program executable by one or more data processing devices of a data processing device system. The program includes an acquisition module configured to cause an acquisition of information stored in a memory device system and a detection module configured to cause a detection of a condition, based at least upon an analysis of the information acquired according to the acquisition module. The condition indicates that a distance between a first non-tissue based electrically conductive surface positioned in a bodily cavity and a first electrode located on a structure positioned in the bodily cavity in a deployed configuration is less than a target distance between the first non-tissue based electrically conductive surface and the first electrode when the structure is in the deployed configuration, the deployed configuration being different than a delivery configuration in which the structure is sized for percutaneous delivery to the bodily cavity. When the structure is positioned in the bodily cavity in the deployed configuration, energy sufficient for tissue ablation is transmittable by the first electrode, at least some of the energy transmittable to adjacent tissue of a tissue wall of the bodily cavity. The program further includes a storage module configured to cause a storage in the memory device system of detection information indicating the detection of the condition according to the detection module. In some embodiments, the computer-readable storage medium system is a non-transitory computer-readable storage medium system that includes one or more non-transitory computer-readable storage mediums.

In some embodiments, a medical device system may be summarized as including a data processing device system and an input-output device system communicatively connected to the data processing device system. The input-output device system includes an electrode-based device system and a sensing device system, a first electrode of the electrode-based-device system located on a structure of the electrode-based device system. The structure is selectively moveable between a delivery configuration in which the structure is sized for percutaneous delivery to a bodily cavity defined at least in part by a tissue wall and a deployed configuration in which at least the first electrode is positioned in the bodily cavity. The medical device system further includes a memory device system communicatively connected to the data processing device system and storing a program executable by the data processing device system. The program includes proximity detection instructions configured to cause a detection of a proximity condition based at least on an analysis of first information provided by or derived from information provided by the sensing device system. The proximity condition indicates a proximity between a first non-tissue based electrically conductive surface and the first electrode when the structure is in the deployed configuration. The first non-tissue based electrically conductive surface is positionable along with the structure in the bodily cavity, and the first information is indicative of, when the structure is positioned in the deployed configuration, an electrical impedance between (a) either the first electrode or the first-non-tissue based electrically conductive surface and (b) a second non-tissue based electrically conductive surface. The second non-tissue based electrically conductive surface is other than the first non-tissue based electrically conductive surface, and the second non-tissue based electrically conductive surface does not form part of the first electrode.

The electrical impedance may be between the first electrode and the second non-tissue based electrically conductive surface. The second non-tissue based electrically conductive surface may be part of an indifferent electrode configured to be positioned outside of the bodily cavity. The electrode-based device system may include a plurality of electrodes that include the first electrode and at least a second electrode, and the second non-tissue based electrically conductive surface may form part of the second electrode. The second electrode may be located on the structure.

The analysis may include an analysis of a combination of the first information and second information, the second information provided by or derived from information provided by the sensing device system, and the second information may be indicative of an amount of contact between the first electrode and tissue of the tissue wall. The second information may include fluid flow information indicative of fluid flow at least proximate the first electrode. The bodily cavity may be an intra-cardiac cavity, and the fluid flow information may be indicative of blood flow at least proximate the first electrode. The bodily cavity may be an intra-cardiac cavity, and the second information may include convective heat information indicative of convective heat transfer caused by blood flow at least proximate the first electrode. The second information may include temperature information determined at a location at least proximate the first electrode.

The first non-tissue based electrically conductive surface may be a portion of the structure, and the second non-tissue based electrically conductive surface may be part of a second electrode other than the first electrode. The second electrode may be an indifferent electrode configured to be positioned outside of the bodily cavity. The second electrode may be located on the structure.

The first non-tissue based electrically conductive surface may be part of a second electrode other than the first electrode. The second electrode may be located on the structure. The second non-tissue based electrically conductive surface may be part of an indifferent electrode configured to be positioned outside of the bodily cavity. The second non-tissue based electrically conductive surface may be a non-electrode portion of the structure. The second non-tissue based electrically conductive surface may be part of a third electrode located on the structure, the third electrode other than each of the first electrode and the second electrode.

The structure may include a plurality of elongate members, and the electrode-based device system may include a plurality of electrodes that include the first electrode, at least some of the plurality of the electrodes located on each of the plurality of elongate members. The first electrode may be located on a first elongate member of the plurality of elongate members, and the first non-tissue based electrically conductive surface may be part of a second elongate member of the plurality of elongate members, the second elongate member being other than the first elongate member. The second non-tissue based electrically conductive surface may be part of an indifferent electrode configured to be positioned outside of the bodily cavity.

The structure may include one or more elongate members, and the electrode-based device system may include a plurality of electrodes that include the first electrode, at least some of the plurality of the electrodes located on each of the one or more elongate members. The first electrode may be located on a first elongate member of the one or more elongate members, and the first non-tissue based electrically conductive surface may be part of a second electrode of the plurality of electrodes, the second electrode located on an elongate member of the one or more elongate members, the second electrode being other than the first electrode. The second non-tissue based electrically conductive surface may be part of an indifferent electrode configured to be positioned outside of the bodily cavity.

The structure may be sized too large for percutaneous delivery to the bodily cavity in the deployed configuration. When the structure is positioned in the bodily cavity in the deployed configuration, energy sufficient for tissue ablation may be transmittable by the first electrode. The sensing device system may form at least part of the electrode-based device system.

The proximity condition may indicate a proximity between the first non-tissue based electrically conductive surface and the first electrode when the first non-tissue based electrically conductive surface, the first electrode or each of the first non-tissue based electrically conductive surface and the first electrode contacts a surface of the tissue wall. The first information may be indicative of the electrical impedance when the first non-tissue based electrically conductive surface, the first electrode or each of the first non-tissue based electrically conductive surface and the first electrode contacts a surface of the tissue wall. In some embodiments, the first information is derived from energy levels insufficient for tissue ablation. In some embodiments, the detection of the proximity condition occurs at a time when energy levels sufficient for tissue ablation (a) have not been applied by the first electrode since the structure was last placed in the deployed configuration, or (b) are not being applied by the first electrode.

In some embodiments, various systems may include combinations and subsets of the systems summarized above.

In some embodiments, a medical device system may be summarized as including a data processing device system and an input-output device system communicatively connected to the data processing device system. The input-output device system includes an electrode-based device system and a sensing device system. A first electrode of the electrode-based-device system is located on a structure of the electrode-based device system, the structure selectively moveable between a delivery configuration in which the structure is sized for percutaneous delivery to a bodily cavity defined at least in part by a tissue wall and a deployed configuration in which at least the first electrode is positionable in the bodily cavity. The medical device system further includes a memory device system communicatively connected to the data processing device system and storing a program executable by the data processing device system. The data processing device system is configured by the program at least to detect a proximity condition based at least on an analysis of first information provided by or derived from information provided by the sensing device system, the proximity condition indicating a proximity between a first non-tissue based electrically conductive surface and the first electrode when the structure is in the deployed configuration. The first non-tissue based electrically conductive surface is positionable along with the structure in the bodily cavity, and the first information is indicative of, when the structure is positioned in the deployed configuration, an electrical impedance between (a) either the first electrode or the first-non-tissue based electrically conductive surface and (b) a second non-tissue based electrically conductive surface. The second non-tissue based electrically conductive surface is other than the first non-tissue based electrically conductive surface, and the second non-tissue based electrically conductive surface does not form part of the first electrode.

In some embodiments, a method is executed by a data processing device system according to a program stored by a memory device system communicatively connected to the data processing device system. The data processing device system is communicatively connected to an input-output device system, the input-output device system including an electrode-based device system and a sensing device system. A first electrode of the electrode-based-device system is located on a structure of the electrode-based device system, the structure selectively moveable between a delivery configuration in which the structure is sized for percutaneous delivery to a bodily cavity defined at least in part by a tissue wall and a deployed configuration in which at least the first electrode is positionable in the bodily cavity. The method may be summarized as including detecting a proximity condition based at least on an analysis of first information provided by or derived from information provided by the sensing device system, the proximity condition indicating a proximity between a first non-tissue based electrically conductive surface and the first electrode when the structure in the deployed configuration. The first non-tissue based electrically conductive surface is positionable along with the structure in the bodily cavity, and the first information is indicative of, when the structure is in the deployed configuration, an electrical impedance between (a) either the first electrode or the first non-tissue based electrically conductive surface and (b) a second non-tissue based electrically conductive surface. The second non-tissue based electrically conductive surface is other than the first non-tissue based electrically conductive surface, and the second non-tissue based electrically conductive surface does not form part of the first electrode.

In some embodiments, a method employs an electrode-based device system and a sensing device system, a first electrode of the electrode-based-device system located on a structure of the electrode-based device system, the structure selectively moveable between a delivery configuration in which the structure is sized for percutaneous delivery to a bodily cavity defined at least in part by a tissue wall and a deployed configuration in which at least the first electrode is positionable in the bodily cavity. The method may be summarized as including detecting a proximity condition based at least on an analysis of first information provided by or derived from information provided by the sensing device system, the proximity condition indicating a proximity between a first non-tissue based electrically conductive surface and the first electrode when the structure is positioned in the deployed configuration, wherein the first non-tissue based electrically conductive surface is positionable along with the structure in the bodily cavity, and the first information is indicative of, when the structure is positioned in the deployed configuration, an electrical impedance between (a) either the first electrode or the first non-tissue based electrically conductive surface and (b) a second non-tissue based electrically conductive surface, wherein the second non-tissue based electrically conductive surface is other than the first non-tissue based electrically conductive surface, and the second non-tissue based electrically conductive surface does not form part of the first electrode. The analysis may include an analysis of a combination of the first information and second information, the second information is provided by or derived from information provided by the sensing device system, and the second information is indicative of an amount of contact between the first electrode and tissue of the tissue wall.

In some embodiments, a computer-readable storage medium system may be summarized as including one or more computer-readable storage mediums storing a program executable by one or more data processing devices of a data processing device system communicatively connected to an input-output device system, the input-output device system including an electrode-based device system and a sensing device system. A first electrode of the electrode-based-device system is located on a structure of the electrode-based device system, the structure selectively moveable between a delivery configuration in which the structure is sized for percutaneous delivery to a bodily cavity defined at least in part by a tissue wall and a deployed configuration in which at least the first electrode positionable in the bodily cavity. The program includes a proximity detection module configured to cause a detection of a proximity condition based at least on an analysis of first information provided by or derived from information provided by the sensing device system, the proximity condition indicating a proximity between a first non-tissue based electrically conductive surface and the first electrode when the structure is in the deployed configuration. The first non-tissue based electrically conductive surface is positionable along with the structure in the bodily cavity, and the first information is indicative of, when the structure is in the deployed configuration, an electrical impedance between (a) either the first electrode or the first-non-tissue based electrically conductive surface and (b) a second non-tissue based electrically conductive surface. The second non-tissue based electrically conductive surface is other than the first non-tissue based electrically conductive surface, and the second non-tissue based electrically conductive surface does not form part of the first electrode. In some embodiments, the computer-readable storage medium system is a non-transitory computer-readable storage medium system that includes one or more non-transitory computer-readable storage mediums.

In some embodiments, a medical device system may be summarized as including a data processing device system; an input-output device system communicatively connected to the data processing device system and comprising an electrode-based device system operable to be inserted into a bodily cavity and to perform tissue ablation in the bodily cavity; and a memory device system communicatively connected to the data processing device system and storing a program executable by the data processing device system. The program includes acquisition instructions configured to acquire information at least from, via, by way of, utilizing, or by employing an electrode of the electrode-based device system, the information derived from energy levels insufficient for tissue ablation. The program also includes detection instructions configured to detect a shunt condition created in an electric circuit in the electrode-based device system based at least upon an analysis of the acquired information, the shunt condition being detected at a time when energy levels sufficient for tissue ablation are not being applied by the electrode. Further, the program includes prevention instructions configured to prevent, in response to the detecting of the shunt condition according to the detection instructions, the electrode from transmitting energy levels sufficient for tissue ablation at least until the shunt condition is detected to no longer exist. In addition, the program includes permission instructions configured to permit the electrode to transmit energy levels sufficient for tissue ablation when the shunt condition is detected to no longer exist.

In some embodiments, a medical device system may be summarized as including a data processing device system; an input-output device system communicatively connected to the data processing device system and comprising an electrode-based device system operable to be inserted into a bodily cavity and to perform tissue ablation in the bodily cavity; and a memory device system communicatively connected to the data processing device system and storing a program executable by the data processing device system. The data processing device system is configured by the program at least to: acquire information at least from, via, by way of, utilizing, or by employing an electrode of the electrode-based device system, the information derived from energy levels insufficient for tissue ablation; detect a shunt condition created in an electric circuit in the electrode-based device system based at least upon an analysis of the acquired information, the shunt condition being detected at a time when energy levels sufficient for tissue ablation are not being applied by the electrode; prevent, in response to the detecting of the shunt condition, the electrode from transmitting energy levels sufficient for tissue ablation at least until the shunt condition is detected to no longer exist; and permit the electrode to transmit energy levels sufficient for tissue ablation when the shunt condition is detected to no longer exist.

In some embodiments, a method is executed by a data processing device system according to a program stored by a memory device system communicatively connected to the data processing device system, the data processing device system communicatively connected to an input-output device system, and the input-output device system comprising an electrode-based device system operable to be inserted into a bodily cavity and to perform tissue ablation in the bodily cavity. The method may be summarized as including: acquiring information at least from, via, by way of, utilizing, or by employing an electrode of the electrode-based device system, the information derived from energy levels insufficient for tissue ablation; detecting a shunt condition created in an electric circuit in the electrode-based device system based at least upon an analysis of the acquired information, the shunt condition being detected at a time when energy levels sufficient for tissue ablation are not being applied by the electrode; preventing, in response to the detecting of the shunt condition, the electrode from transmitting energy levels sufficient for tissue ablation at least until the shunt condition is detected to no longer exist; and permitting the electrode to transmit energy levels sufficient for tissue ablation when the shunt condition is detected to no longer exist.

In some embodiments, a computer-readable storage medium system may be summarized as including one or more computer-readable storage mediums storing a program executable by one or more data processing devices of a data processing device system communicatively connected to an input-output device system comprising an electrode-based device system operable to be inserted into a bodily cavity and to perform tissue ablation in the bodily cavity. The program includes an acquisition module configured to cause an acquisition of information at least from, via, by way of, utilizing, or by employing an electrode of the electrode-based device system, the information derived from energy levels insufficient for tissue ablation; a detection module configured to cause a detection of a shunt condition created in an electric circuit in the electrode-based device system based at least upon an analysis of the acquired information, the shunt condition being detected at a time when energy levels sufficient for tissue ablation are not being applied by the electrode; a prevention module configured to cause a prevention of, in response to the detecting of the shunt condition according to the detection module, the electrode from transmitting energy levels sufficient for tissue ablation at least until the shunt condition is detected to no longer exist; and a permission module configured to cause permission of the electrode to transmit energy levels sufficient for tissue ablation when the shunt condition is detected to no longer exist.

In some embodiments, a medical device system may be summarized as including a data processing device system; an input-output device system communicatively connected to the data processing device system, the input-output device system comprising an electrode-based device system that includes a plurality of electrodes, a portion of the electrode-based device system receivable in a bodily cavity to perform tissue ablation in the bodily cavity; and a memory device system communicatively connected to the data processing device system and storing a program executable by the data processing device system. The program includes: energy transmission instructions configured to cause transmission of energy between a first electrode of the electrode-based device system and a second electrode of the electrode-based device system; detection instructions configured to detect a shunt condition in which a portion of the energy transmitted between the first and the second electrodes of the electrode-based device system is diverted to a physical portion of the electrode-based device system other than the first and the second electrodes of the electrode-based device system; prevention instructions configured to, at least in response to the detected shunt condition, prevent the first electrode of the electrode-based device system, the second electrode of the electrode-based device system, or both the first and the second electrodes of the electrode-based device system from transmitting energy levels sufficient for tissue ablation at least until the shunt condition is detected to no longer exist; and permission instructions configured to permit the first electrode of the electrode-based device system, the second electrode of the electrode-based device system, or both the first and the second electrodes of the electrode-based device system to transmit energy levels sufficient for tissue ablation when the shunt condition is detected to no longer exist. Each of the first and the second electrodes of the electrode-based device system may be receivable in the bodily cavity. The physical portion of the electrode-based device system may be receivable in the bodily cavity. The physical portion of the electrode-based device system may include at least one electrode of the plurality of electrodes. The physical portion of the electrode-based device system may include a non-electrode portion of the electrode-based device system. The electrode-based device system may include a structure receivable in the bodily cavity, at least some of the plurality of electrodes located on the structure, and the physical portion of the electrode-based device system may include a non-electrode portion of the structure. The non-electrode portion of the structure may include an external electrically conductive surface. The structure may be selectively moveable between a delivery configuration in which the structure is sized for percutaneous delivery to the bodily cavity and a deployed configuration in which the structure is sized too large for percutaneous delivery to the bodily cavity. The energy caused to be transmitted between the first and the second electrodes of the electrode-based device system by the energy transmission instructions may be energy insufficient for tissue ablation, and the shunt condition may be defined to be detected according to the detection instructions least in response to a portion of the energy insufficient for tissue ablation being diverted to the physical portion of the electrode-based device system. The diverted portion of the energy may be insufficient for tissue ablation.

In some embodiments, a medical device system may be summarized as including a data processing device system; an input-output device system communicatively connected to the data processing device system, the input-output device system comprising an electrode-based device system that includes a plurality of electrodes, at least a portion of the electrode-based device system receivable in a bodily cavity to perform tissue ablation in the bodily cavity; and a memory device system communicatively connected to the data processing device system and storing a program executable by the data processing device system. The data processing device system is configured by the program at least to: cause a transmission of energy between a first electrode of the electrode-based device system and a second electrode of the electrode-based device system; detect a shunt condition in which a portion of the energy transmitted between the first and the second electrodes of the electrode-based device system is diverted to a physical portion of the electrode-based device system other than the first and the second electrodes of the electrode-based device system; prevent, at least in response to the detected shunt condition, the first electrode of the electrode-based device system, the second electrode of the electrode-based device system, or both the first and the second electrodes of the electrode-based device system from transmitting energy levels sufficient for tissue ablation at least until the shunt condition is detected to no longer exist; and permit the first electrode of the electrode-based device system, the second electrode of the electrode-based device system, or both the first and the second electrodes of the electrode-based device system to transmit energy levels sufficient for tissue ablation when the shunt condition is detected to no longer exist.

In some embodiments, a method employs an electrode-based device system that includes a plurality of electrodes, at least a portion of the electrode-based device system receivable in a bodily cavity to perform tissue ablation in the bodily cavity. The method may be summarized as including: transmitting energy between a first electrode of the electrode-based device system and a second electrode of the electrode-based device system; detecting a shunt condition in which a portion of the energy transmitted between the first and the second electrodes of the electrode-based device system is diverted to a physical portion of the electrode-based device system other than the first and the second electrodes of the electrode-based device system; preventing, at least in response to the detecting of the shunt condition, the first electrode of the electrode-based device system, the second electrode of the electrode-based device system, or both the first and the second electrodes of the electrode-based device system from transmitting energy levels sufficient for tissue ablation at least until the shunt condition is detected to no longer exist; and permitting the first electrode of the electrode-based device system, the second electrode of the electrode-based device system, or both the first and the second electrodes of the electrode-based device system to transmit energy levels sufficient for tissue ablation when the shunt condition is detected to no longer exist.

In some embodiments, a computer-readable storage medium system may be summarized as including one or more computer-readable storage mediums storing a program executable by one or more data processing devices of a data processing device system communicatively connected to an input-output device system comprising an electrode-based device system operable to be inserted, at least in part, into a bodily cavity and to perform tissue ablation in the bodily cavity. The program includes: an energy transmission module configured to cause transmission of energy between a first electrode of the electrode-based device system and a second electrode of the electrode-based device system; a detection module configured to cause a detection of a shunt condition in which a portion of the energy transmitted between the first and the second electrodes of the electrode-based device system is diverted to a physical portion of the electrode-based device system other than the first and the second electrodes of the electrode-based device system; a prevention module configured to, at least in response to the detected shunt condition, cause the first electrode of the electrode-based device system, the second electrode of the electrode-based device system, or both the first and the second electrodes of the electrode-based device system to be prevented from transmitting energy levels sufficient for tissue ablation at least until the shunt condition is detected to no longer exist; and a permission module configured to cause the first electrode of the electrode-based device system, the second electrode of the electrode-based device system, or both the first and the second electrodes of the electrode-based device system to be permitted to transmit energy levels sufficient for tissue ablation when the shunt condition is detected to no longer exist.

Various systems may include combinations and subsets of all the systems summarized above.

Various methods may include combinations and subsets of all the methods summarized above. In addition, a computer program product may be provided that comprises program code portions for performing some or all of any of the methods summarized above or otherwise herein, when the computer program product is executed by a computing device. The computer program product may be stored on one or more computer-readable storage mediums. The one or more computer-readable storage mediums may be non-transitory computer-readable storage mediums.

BRIEF DESCRIPTION OF THE DRAWINGS

It is to be understood that the attached drawings are for purposes of illustrating aspects of various embodiments and may include elements that are not to scale.

FIG. 5H is an exploded view of some of the blocks of the block diagram of FIG. 5A according to some example embodiments, the exploded blocks associated with a detection of a proximity condition indicating a proximity between a first non-tissue based electrically conductive surface and a first electrode, according to some embodiments.

FIG. 6A is a schematic cross sectional view, according to various example embodiments, of a first electrode positioned adjacent tissue of a tissue wall that defines, at least in part, a bodily cavity, energy transmittable from the first electrode flowing along a first electrical path, according to some embodiments.

FIG. 6B is a top view of at least the first electrode and tissue wall of FIG. 6A, according to some embodiments.

FIG. 6C illustrates a shunt condition associated with a diversion of a portion of energy transmittable by the first electrode of FIG. 6A from the first electrical path to a second electrical path different than the first electrical path, according to some embodiments.

FIG. 6D is a top view of at least the first electrode and tissue wall of FIG. 6C, according to some embodiments.

DETAILED DESCRIPTION

Figure 1:
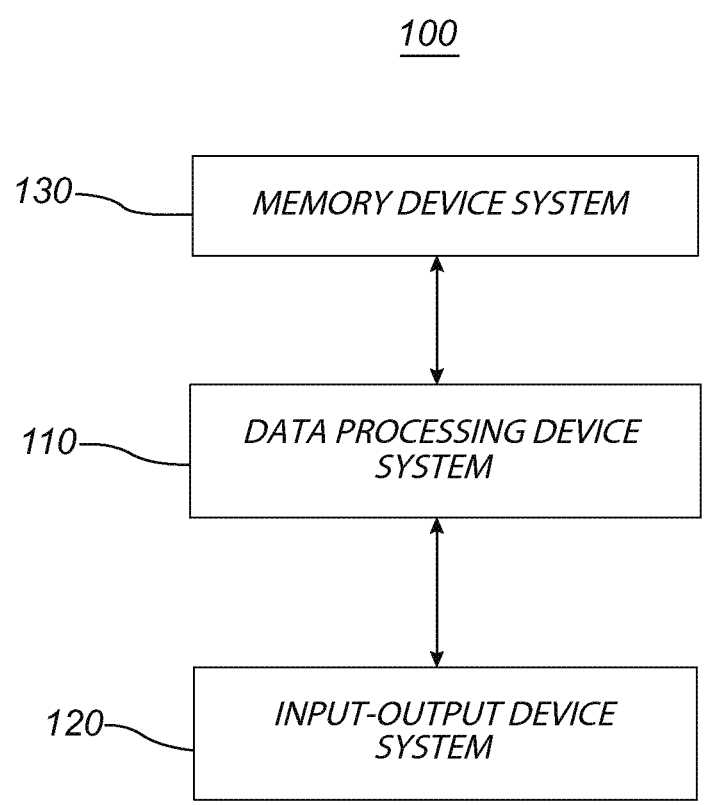
FIG. 1 is a schematic representation of a medical device system according to various example embodiments, where the medical device system may include a data processing device system, an input-output device system, and a memory device system, according to some embodiments.

Some embodiments of the present invention pertain to the detection of conditions where energy intended to be transmitted or delivered to one location could instead be delivered to another location. Although such conditions may arise in other contexts, they may be particularly important in medical device systems where consequences of an improper energy transmission or delivery configuration might be associated with elevated risk. For example, in procedures configured to treat atrial fibrillation, ablative energy is intended to be delivered to tissue forming an interior cavity of a heart by way of one or more electrodes. Often times, an intended operational state of an ablation device including such one or more electrodes is to have such electrode(s) contact or at least be available (e.g., without some obstruction preventing at least some of the ability) to contact the tissue forming the interior cavity of the heart so that ablative energy may be transferred to such tissue in order to form a lesion that blocks or contains (e.g., surrounds) the spurious electrical signals causing the fibrillation. However, if an electrode is inadvertently too close to another conductive portion of the ablation device, it is possible that at least a portion of ablative energy delivered by the electrode will travel towards that other conductive portion of the ablation device and not reach its intended target, an intended portion of the tissue. Such a circumstance can lead to unintended energy being delivered elsewhere to the patient. In this regard, some embodiments of the present invention facilitate detection of at least some of these unintended circumstances so that they can be avoided. However, it can be seen that various embodiments of the present invention are not limited to intra-cardiac medical devices or even medical devices more generally and, instead, have broader applicability.

In the following description, certain specific details are set forth in order to provide a thorough understanding of various embodiments of the invention. However, one skilled in the art will understand that the invention may be practiced without these details. In other instances, well-known structures have not been shown or described in detail to avoid unnecessarily obscuring descriptions of various embodiments of the invention.

Reference throughout this specification to "one embodiment" or "an embodiment" or "an example embodiment" or "an illustrated embodiment" or "a particular embodiment" and the like means that a particular feature, structure or characteristic described in connection with the embodiment is included in at least one embodiment. Thus, the appearances of the phrases "in one embodiment" or "in an embodiment" or "in an example embodiment" or "in this illustrated embodiment" or "in this particular embodiment" and the like in various places throughout this disclosure are not necessarily all referring to one embodiment or a same embodiment. Furthermore, the particular features, structures or characteristics of different embodiments may be combined in any suitable manner to form one or more other embodiments.

Unless otherwise explicitly noted or required by context, the word "or" is used in this disclosure in a non-exclusive sense. In addition, unless otherwise explicitly noted or required by context, the word "set" is intended to mean one or more. For example, the phrase, "a set of objects" means one or more of the objects. In addition, unless otherwise explicitly noted or required by context, the word "subset" is intended to mean a set having the same or fewer elements of those present in the subset's parent or superset.

Further, the phrase "at least" is used herein at times to emphasize the possibility that other elements can exist besides those explicitly listed. However, unless otherwise explicitly noted (such as by the use of the term "only") or required by context, non-usage herein of the phrase "at least" includes the possibility that other elements exist besides those explicitly listed. For example, the phrase, 'based at least upon A' includes A, as well as the possibility of one or more other additional elements besides A. In the same manner, for example, the phrase, 'based upon A' includes A, as well as the possibility of one or more other additional elements besides A. However, for example, the phrase, 'based only upon A' includes only A.

The word "fluid" as used in this disclosure should be understood to include any fluid that can be contained within a bodily cavity or can flow into or out of, or both into and out of a bodily cavity via one or more bodily openings positioned in fluid communication with the bodily cavity. In some embodiments, the word "fluid" may include fluid that is not inherent to the bodily cavity, such as saline or other fluid that might artificially introduced into the bodily cavity. In the case of cardiac applications, fluid such as blood will flow into and out of various intra-cardiac cavities (e.g., a left atrium or right atrium).

The phrase "bodily opening" as used in this disclosure should be understood to include a naturally occurring bodily opening or channel or lumen; a bodily opening or channel or lumen formed by an instrument or tool using techniques that can include, but are not limited to, mechanical, thermal, electrical, chemical, and exposure or illumination techniques; a bodily opening or channel or lumen formed by trauma to a body; or various combinations of one or more of the above or other bodily openings. Various elements having respective openings, lumens or channels and positioned within the bodily opening (e.g., a catheter sheath) may be present in various embodiments. These elements may provide a passageway through a bodily opening for various devices employed in various embodiments.

The words "bodily cavity" as used in this disclosure should be understood to mean a cavity in a body. The bodily cavity may be a cavity provided in a bodily organ (e.g., an intra-cardiac cavity or chamber of a heart).

The word "tissue" often is used in this disclosure, and tissue may include non-fluidic tissue and fluidic tissue. Non-fluidic tissue generally (or predominantly) has solid-like properties, such as tissue that forms a surface of a body or a surface within a bodily cavity, a surface of an anatomical feature or a surface of a feature associated with a bodily opening positioned in fluid communication with the bodily cavity. Non-fluidic tissue can include part or all of a tissue wall or membrane that defines a surface of the bodily cavity.

In this regard, the tissue can form an interior surface of the cavity that at least partially surrounds a fluid within the cavity. In the case of cardiac applications, non-fluidic tissue can include tissue used to form an interior surface of an intra-cardiac cavity such as a left atrium or right atrium. Fluidic tissue, on the other hand, generally (or predominantly) has fluid-like properties (as compared to solid-like properties). An example of fluidic tissue is blood. In this regard, it should be noted that fluidic tissue can have some solid-like component(s) (e.g., non-fluidic tissue may include solid-like components), and non-fluidic tissue can have some fluid-like component(s) (e.g., non-fluidic tissue may include fluidic tissue within it). Unless otherwise explicitly noted or required by context, the word "tissue" should include non-fluidic tissue and fluidic tissue. However, some contexts where the word "tissue" would not include fluidic tissue are when tissue ablation is discussed, and ablation of fluidic tissue could be undesired, as discussed below. In various embodiments, non-fluidic tissue does not include excised tissue.

The word "ablation" as used in this disclosure should be understood to include any disruption to certain properties of tissue. Most commonly, the disruption is to the electrical conductivity of tissue and may be achieved by heating, which can be generated with resistive or radio-frequency (RF) techniques for example. Other properties of tissue, such as mechanical or chemical, and other means of disruption, such as optical, are included when the term "ablation" is used. In some embodiments, ablative power levels may be within the range of 3 W to 5 W (as compared, e.g., to a non-tissue-ablative power level range of 50 mW to 60 mW that may be used for typical impedance determinations). In some embodiments, ratios of employed ablative power levels to employed non-tissue-ablative power levels (e.g., used for typical impedance determinations) may be: at least equal or greater to 50:1 in various embodiments; at least greater than 60:1 in some embodiments; at least greater to 80:1 in other various embodiments; and at least greater than 100:1 in yet other embodiments. In some embodiments, systems are configured to perform ablation of non-fluidic tissue while avoiding the delivery of excessive energy to fluidic tissue, because energy that is sufficient to ablate non-fluidic tissue may also impact fluidic tissue in some circumstances. For example, energy that is sufficient to ablate non-fluidic tissue, in some circumstances, may cause blood (an example of fluidic tissue) to coagulate. In these and other embodiments where ablative energy transferred to fluidic tissue is not desired, it should be understood that any statement or reference to the 'ablation of tissue' or the like in these contexts is intended to refer to ablation of non-fluidic tissue, as opposed to ablation of fluidic tissue. Techniques, according to some embodiments disclosed herein, facilitate the detection of conditions where energy that is intended to ablate non-fluidic tissue might unintentionally be delivered to blood or another object.

The term "transducer" as used in this disclosure should be interpreted broadly as any device capable at least of distinguishing between fluid and non-fluidic tissue, sensing temperature, creating heat, ablating tissue and measuring electrical activity of a tissue surface, stimulating tissue or any combination thereof. A transducer can convert input energy of one form into output energy of another form. Without limitation, a transducer can include an electrode, and references to a "transducer" herein can be replaced with "electrode" according to some embodiments. Without limitation, a transducer can include an electrode or a sensing device, or both an electrode and a sensing device. An electrode, in some embodiments, can be configured at least as a sensing device. Because a transducer can include an electrode according to various embodiments, any reference herein to a transducer may also imply a reference to an electrode, or vice versa. A transducer may be constructed from several parts, which may be discrete components or may be integrally formed.

The term "activation" should be interpreted broadly as making active a particular function as related to various transducers such as those disclosed herein, for example. Particular functions can include, but are not limited to, tissue ablation, sensing electrophysiological activity, sensing temperature and sensing electrical characteristics (e.g., tissue impedance). For example, in some embodiments, activation of a tissue ablation function of a particular transducer is initiated by causing energy sufficient for tissue ablation from an energy source device system to be delivered to the particular transducer. In some embodiments, activation of a tissue ablation function of a particular electrode is initiated by causing energy from an energy source device system to be delivered to the particular electrode, the energy sufficient for tissue ablation. In some embodiments, activation of a tissue ablation function of a particular electrode is initiated by causing energy sufficient for tissue ablation to be transmitted by the particular electrode. Alternatively, in some embodiments, the activation can be deemed to be initiated when the particular transducer or particular electrode causes tissue that is to be ablated to reach or acquire a temperature sufficient for ablation of the tissue, which may be due to the energy provided by the energy source device system or due to the energy transmitted by the particular transducer or electrode. In some embodiments, the activation can last for a duration concluding when the ablation function is no longer active, such as when energy sufficient for the tissue ablation is no longer provided to, or transmitted by, the particular transducer or particular electrode. Alternatively, in some embodiments, the activation period can be deemed to be concluded when the tissue that is being ablated has a temperature below that sufficient for ablation of the tissue, which may be due to a reduction or cessation of the energy provided by the energy source device system or transmitted by the particular transducer or electrode. In some contexts, however, the word "activation" can merely refer to the initiation of the activating of a particular function, as opposed to referring to both the initiation of the activating of the particular function and the subsequent duration in which the particular function is active. In these contexts, the phrase or a phrase similar to "activation initiation" may be used. For example, in some embodiments activation initiation may cause initiation of a transmission of energy (e.g., energy sufficient for tissue ablation) from a particular transducer or electrode.

The term "program" in this disclosure should be interpreted as a set of instructions or modules that can be executed by one or more components in a system, such as a controller system or data processing device system, in order to cause the system to perform one or more operations. The set of instructions or modules can be stored by any kind of memory device, such as those described subsequently with respect to the memory device system 130 shown in FIG. 1. In addition, it may be described that the instructions or modules of a program are configured to cause the performance of a function. The phrase "configured to" in this context is intended to include at least (a) instructions or modules that are presently in a form executable by one or more data processing devices to cause performance of the function (e.g., in the case where the instructions or modules are in a compiled and unencrypted form ready for execution), and (b) instructions or modules that are presently in a form not executable by the one or more data processing devices, but could be translated into the form executable by the one or more data processing devices to cause performance of the function (e.g., in the case where the instructions or modules are encrypted in a non-executable manner, but through performance of a decryption process, would be translated into a form ready for execution). The word "module" can be defined as a set of instructions.

Further, it is understood that information or data may be operated upon, manipulated, or converted into different forms as it moves through various devices or workflows. In this regard, unless otherwise explicitly noted or required by context, it is intended that any reference herein to information or data includes modifications to that information or data. For example, "data X" may be encrypted for transmission, and a reference to "data X" is intended to include both its encrypted and unencrypted forms. For another example, "image information Y" may undergo a noise filtering process, and a reference to "image information Y" is intended to include both the pre-processed form and the noise-filtered form. In other words, both the pre-processed form and the noise-filtered form are considered to be "image information Y". In order to stress this point, the phrase "or a derivative thereof" or the like may be used herein. Continuing the preceding example, the phrase "image information Y or a derivative thereof" refers to both the pre-processed form and the noise-filtered form of "image information Y", with the noise-filtered form potentially being considered a derivative of "image information Y". However, non-usage of the phrase "or a derivative thereof" or the like nonetheless includes derivatives or modifications of information or data just as usage of such a phrase does, as such a phrase, when used, is merely used for emphasis.

The word "device" and the phrase "device system" both are intended to include one or more physical devices or sub-devices (e.g., pieces of equipment) that interact to perform one or more functions, regardless of whether such devices or sub-devices are located within a same housing or different housings. In this regard, for example, the phrase "electrode-based device" could equivalently be referred to as an "electrode-based device system".

In some contexts, the term "adjacent" may be used to refer to objects that do not have another substantially similar object between them. For example, object A and object B could be considered adjacent if they contact each other (and, thus, it could be considered that no other object is between them), or if they do not contact each other but no other object that is substantially similar to object A, object B, or both objects A and B, depending on context, is between them. In some contexts, the term "adjacent" additionally refers to at least a sufficient proximity between the objects defined as adjacent to allow the objects to interact in a designated way. For example, if object A performs an action on an adjacent object B, objects A and B would have at least a sufficient proximity to allow object A to perform the action on the object B. In this regard, some actions may require contact between the associated objects, such that if object A performs such an action on an adjacent object B, objects A and B would be in contact.

Further, the phrase "in response to" may be used in a context where an event A occurs in response to the occurrence of an event B. In this regard, such phrase can include, for example, that at least the occurrence of the event B causes or triggers the event A.

In some contexts, the term "proximity" is used in this disclosure to refer to a degree of closeness between various objects. For example, a proximity between an object A and an object B could be considered to mean a degree of closeness of (a) object A to object B, (b) object B to object A, or both (a) and (b). Such degree of closeness may include contact in some embodiments.

Further still, example methods are described herein with respect to FIGS. 5A, 5B, 5C, 5D, 5E, 5F, 5G, and 5H. Such figures are described to include blocks associated with instructions. It should be noted that the respective instructions associated with various method blocks herein, need not be separate instructions and may be combined with other instructions to form a combined instruction set. In this regard, the blocks shown in each of the method figures herein are not intended to illustrate an actual structure of any program or set of instructions, and such method figures, according to some embodiments, merely illustrate the tasks or processes that instructions are configured to perform upon execution by a data processing device system in conjunction with interactions with one or more other devices or device systems.

FIG. 1 schematically illustrates a medical device system 100 according to some embodiments. Although the system 100 is described as a medical device system 100, such system 100 is not limited thereto, and can be another type of system, such as a system configured to detect one or more improper energy transmission configurations in a system in which energy transmission is a priority. In this regard, such detecting of one or more improper energy transmission configures can be important in, among other systems, medical device systems, where energy transmission may need to be properly controlled to successfully treat a patient in a desired manner.

In some embodiments, the medical device system 100 includes a data processing device system 110, an input-output device system 120, and a processor-accessible memory device system 130. The processor-accessible memory device system 130 and the input-output device system 120 are communicatively connected to the data processing device system 110.

The data processing device system 110 includes one or more data processing devices that implement or execute, in conjunction with other devices, such as one or more of those in the system 100, the methods of various embodiments, including the example methods of 5A, 5B, 5C, 5D, 5E, 5F, 5G, and 5H described herein. Each of the phrases "data processing device", "data processor", "processor", and "computer" is intended to include any data processing device, such as a central processing unit ("CPU"), a desktop computer, a laptop computer, a mainframe computer, a tablet computer, a personal digital assistant, a cellular phone, and any other device configured to process data, manage data, or handle data, whether implemented with electrical, magnetic, optical, biological components, or other.

The memory device system 130 includes one or more processor-accessible memory devices configured to store information, including the information needed to execute the methods of various embodiments, including the example methods of FIGS. 5A, 5B, 5C, 5D, 5E, 5F, 5G, and 5H described herein. The memory device system 130 may be a distributed processor-accessible memory device system including multiple processor-accessible memory devices communicatively connected to the data processing device system 110 via a plurality of computers and/or devices. On the other hand, the memory device system 130 need not be a distributed processor-accessible memory system and, consequently, may include one or more processor-accessible memory devices located within a single data processing device.

Each of the phrases "processor-accessible memory" and "processor-accessible memory device" is intended to include any processor-accessible data storage device, whether volatile or nonvolatile, electronic, magnetic, optical, or otherwise, including but not limited to, registers, floppy disks, hard disks, Compact Discs, DVDs, flash memories, ROMs, and RAMs. In some embodiments, each of the phrases "processor-accessible memory" and "processor-accessible memory device" is intended to include a non-transitory computer-readable storage medium. In some embodiments, the memory device system 130 can be considered a non-transitory computer-readable storage medium system.

The phrase "communicatively connected" is intended to include any type of connection, whether wired or wireless, between devices, data processors, or programs in which data may be communicated. Further, the phrase "communicatively connected" is intended to include a connection between devices or programs within a single data processor, a connection between devices or programs located in different data processors, and a connection between devices not located in data processors at all. In this regard, although the memory device system 130 is shown separately from the data processing device system 110 and the input-output device system 120, one skilled in the art will appreciate that the memory device system 130 may be located completely or partially within the data processing device system 110 or the input-output device system 120. Further in this regard, although the input-output device system 120 is shown separately from the data processing device system 110 and the memory device system 130, one skilled in the art will appreciate that such system may be located completely or partially within the data processing system 110 or the memory device system 130, depending upon the contents of the input-output device system 120. Further still, the data processing device system 110, the input-output device system 120, and the memory device system 130 may be located entirely within the same device or housing or may be separately located, but communicatively connected, among different devices or housings. In the case where the data processing device system 110, the input-output device system 120, and the memory device system 130 are located within the same device, the system 100 of FIG. 1 can be implemented by a single application-specific integrated circuit (ASIC) in some embodiments.

The input-output device system 120 may include a mouse, a keyboard, a touch screen, another computer, or any device or combination of devices from which a desired selection, desired information, instructions, or any other data is input to the data processing device system 110. The input-output device system 120 may include a user-activatable control system that is responsive to a user action, such as actions from a care provider such as a physician or technician. The input-output device system 120 may include any suitable interface for receiving information, instructions or any data from other devices and systems described in various ones of the embodiments. In this regard, the input-output device system 120 may include various ones of other systems described in various embodiments. For example, the input-output device system 120 may include at least a portion of a transducer-based device system or an electrode-based device system. The phrase "transducer-based device system" is intended to include one or more physical devices or systems that include various transducers. Similarly, the phrase "electrode-based device system" is intended to include one or more physical devices or systems that include various electrodes. In this regard, the phrases "transducer-based device system" and "electrode-based device system" may be used interchangeably in accordance with various embodiments. Similarly, the phrases "transducer-based device" and "electrode-based device" may be used interchangeably in accordance with various embodiments.

The input-output device system 120 also may include an image generating device system, a display device system, a speaker device system, a processor-accessible memory device system, or any device or combination of devices to which information, instructions, or any other data is output from the data processing device system 110. In this regard, if the input-output device system 120 includes a processor-accessible memory device, such memory device may or may not form part or all of the memory device system 130. The input-output device system 120 may include any suitable interface for outputting information, instructions or data to other devices and systems described in various ones of the embodiments. In this regard, the input-output device system may include various other devices or systems described in various embodiments.

Figure 2:
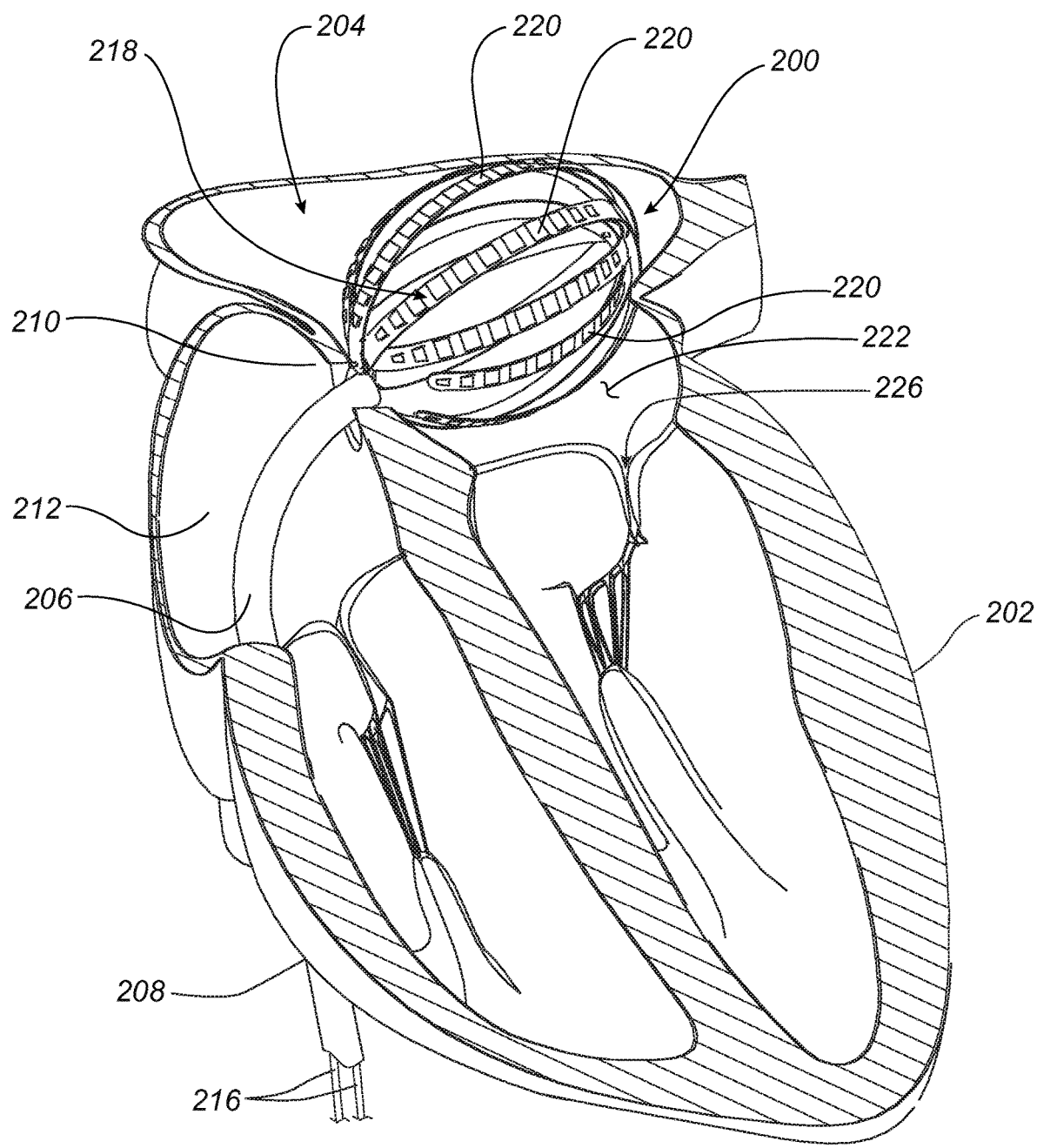
FIG. 2 is a cutaway diagram of a heart showing an electrode-based device system percutaneously placed in a left atrium of the heart according to various example embodiments, the electrode-based device system optionally being part of the input-output device system of FIG. 1, according to some embodiments.

FIG. 2 shows an electrode-based device system 200, which may be included in the input-output device system 120 of FIG. 1, according to some embodiments. Because, as described in more detail below with respect to FIG. 4, electrodes may be part of transducers, according to some embodiments, the system 200 may also be considered a transducer-based device system in some embodiments.

Such a system 200 may be useful for, among other things, investigating or treating a bodily organ, for example a heart 202, according to some example embodiments. The electrode-based device system 200 can be percutaneously or intravascularly inserted into a portion of the heart 202, such as an intra-cardiac cavity like left atrium 204. In this example, the electrode-based device system 200 includes a catheter 206 inserted via the inferior vena cava 208 and penetrating through a bodily opening in transatrial septum 210 from right atrium 212. In other embodiments, other paths may be taken.

Catheter 206 may include an elongated flexible rod or shaft member appropriately sized to be delivered percutaneously or intravascularly. Various portions of catheter 206 may be steerable. Catheter 206 may include one or more lumens (not shown). The lumen(s) may carry one or more communications or power paths, or both. For example, the lumens(s) may carry one or more electrical conductors 216 (two shown in this embodiment). Electrical conductors 216 provide electrical connections for system 200 that are accessible externally from a patient in which the electrode-based device system 200 is inserted.

In some embodiments, the electrical conductors 216 may provide electrical connections to transducers 220 (three called out in FIG. 2) that respectively include one or more electrodes, and optionally one or more other devices, (e.g., both discussed with respect to FIG. 4, below) configured to, among other things, provide stimulation (e.g., electrical stimulation that may include pinging or pacing) to tissue within a bodily cavity (e.g., left atrium 204), ablate tissue in a desired pattern within the bodily cavity, sense characteristics of tissue (e.g., electrophysiological activity, convective cooling, permittivity, force, temperature, impedance, thickness, or a combination thereof) within the bodily cavity, or a combination thereof.

The sensing of characteristics may, among other things, be configured to distinguish between fluid, such as fluidic tissue (e.g., blood), and non-fluidic tissue forming an interior surface of a bodily cavity (e.g., left atrium 204); may be configured to map the cavity, for example, using positions of openings or ports into and out of the cavity to determine a position or orientation (e.g., pose), or both of a portion of the device system 200 in the bodily cavity; may be configured to indicate whether an ablation has been successful; or a combination thereof.

Electrode-based device system 200 may include a frame or structure 218 which assumes an unexpanded or delivery configuration (e.g., FIG. 3A, discussed below) for delivery to left atrium 204. Structure 218 is deployed or expanded (i.e., shown in a deployed or expanded configuration in FIG. 2, as well as FIGS. 3B, 3C, and 3D, which are discussed below) upon delivery to left atrium 204. In this regard, in some embodiments, the electrode-based device system 200 is moveable between a delivery or unexpanded configuration (e.g., FIG. 3A, discussed below) in which a portion (e.g., the structure 218) of the device system 200 is sized for passage though a bodily opening leading to a bodily cavity, and a deployed or expanded configuration (e.g., FIG. 2, as well as FIGS. 3B, 3C, and 3D discussed below) in which the portion of the device system 200 has a size too large for passage through the bodily opening leading to the bodily cavity. An example of an expanded or deployed configuration is when the portion of the electrode-based device system is in its intended-deployed-operational state inside the bodily cavity. Another example of the expanded or deployed configuration is when the portion of the electrode-based device system is being changed from the delivery configuration to the intended-deployed-operational state to a point where the portion of the device system now has a size too large for passage through the bodily opening leading to the bodily cavity. Further, in some embodiments, when the portion (e.g., the structure 218) is in the expanded or deployed configuration in the left atrium 204, various ones of a plurality of transducers 220 are positioned proximate the interior surface formed by non-fluidic tissue 222 of left atrium 204. In some embodiments, when the portion (e.g., the structure 218) is in the expanded or deployed configuration in the left atrium 204, various ones of plurality of transducers 220 are positioned such that a physical portion of each of the various ones of the transducers 220 is configured to contact the interior surface formed by non-fluidic tissue 222 of left atrium 204. In some embodiments, at least some of the transducers 220 are configured to sense a physical characteristic of a fluid (i.e., blood), non-fluidic tissue 222 (i.e., cardiac wall tissue), or both, that may be used to determine a position or orientation (i.e., pose), or both, of a portion of a device system 200 within, or with respect to left atrium 204. For example, transducers 220 may be configured to determine a location of pulmonary vein ostia (not shown) or a mitral valve 226, or both. In some embodiments, at least some of the transducers 220 may be controlled to selectively ablate portions of the non-fluidic tissue 222. For example, some of the transducers 220 may be controlled to ablate a pattern or path around various ones of the bodily openings, ports or pulmonary vein ostia, for instance, to reduce or eliminate the occurrence of atrial fibrillation. Each of various ones of the transducers 220 may include an electrode in various embodiments, as described below with respect to FIG. 4, for example.

Figure 3A:
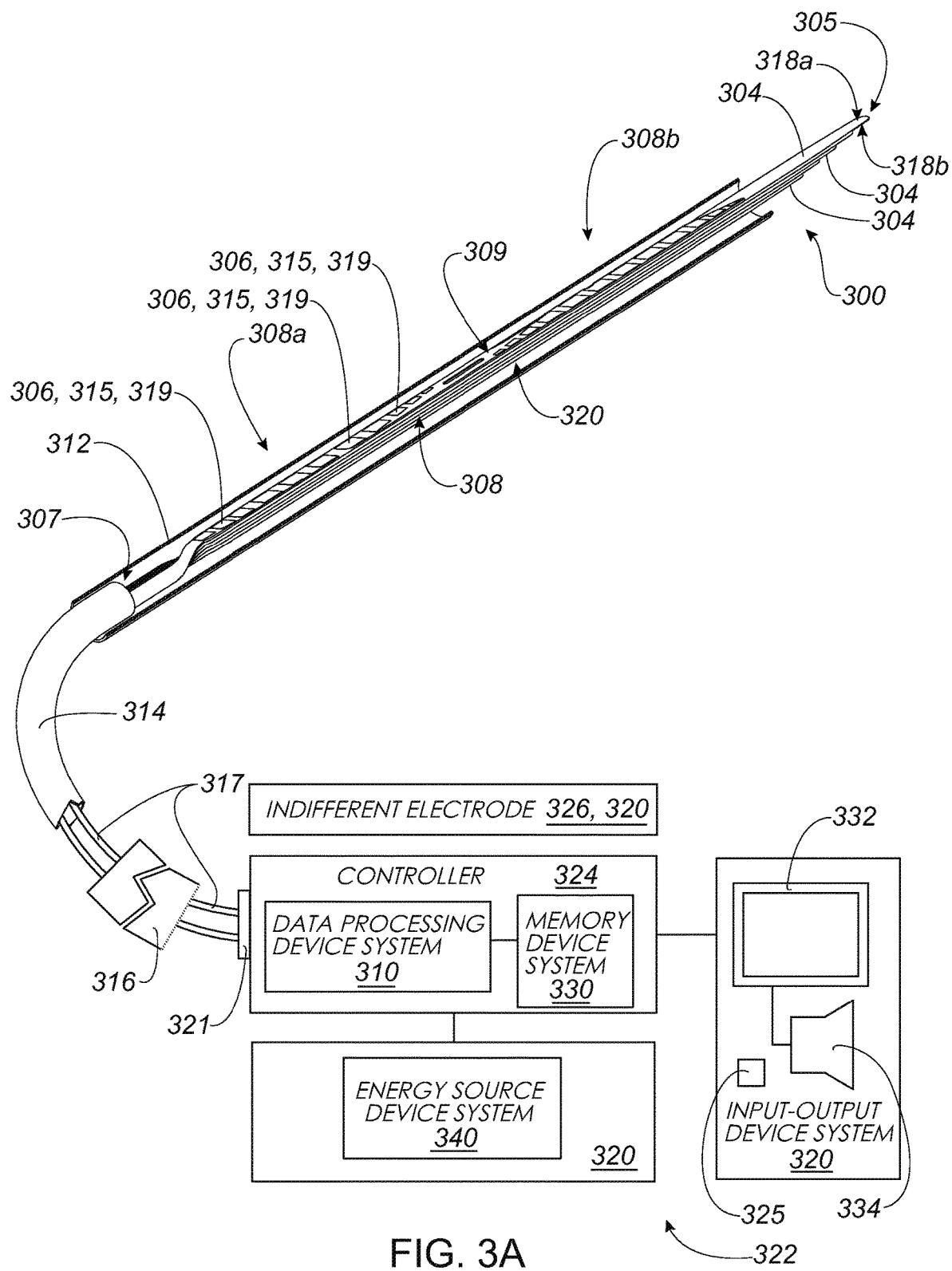
FIG. 3A is a partially schematic representation of a medical device system, which may represent one or more implementations of the medical device system of FIG. 1 in which an expandable structure of an electrode-based device system is in a delivery or unexpanded configuration, according to various example embodiments.
Figure 3B:
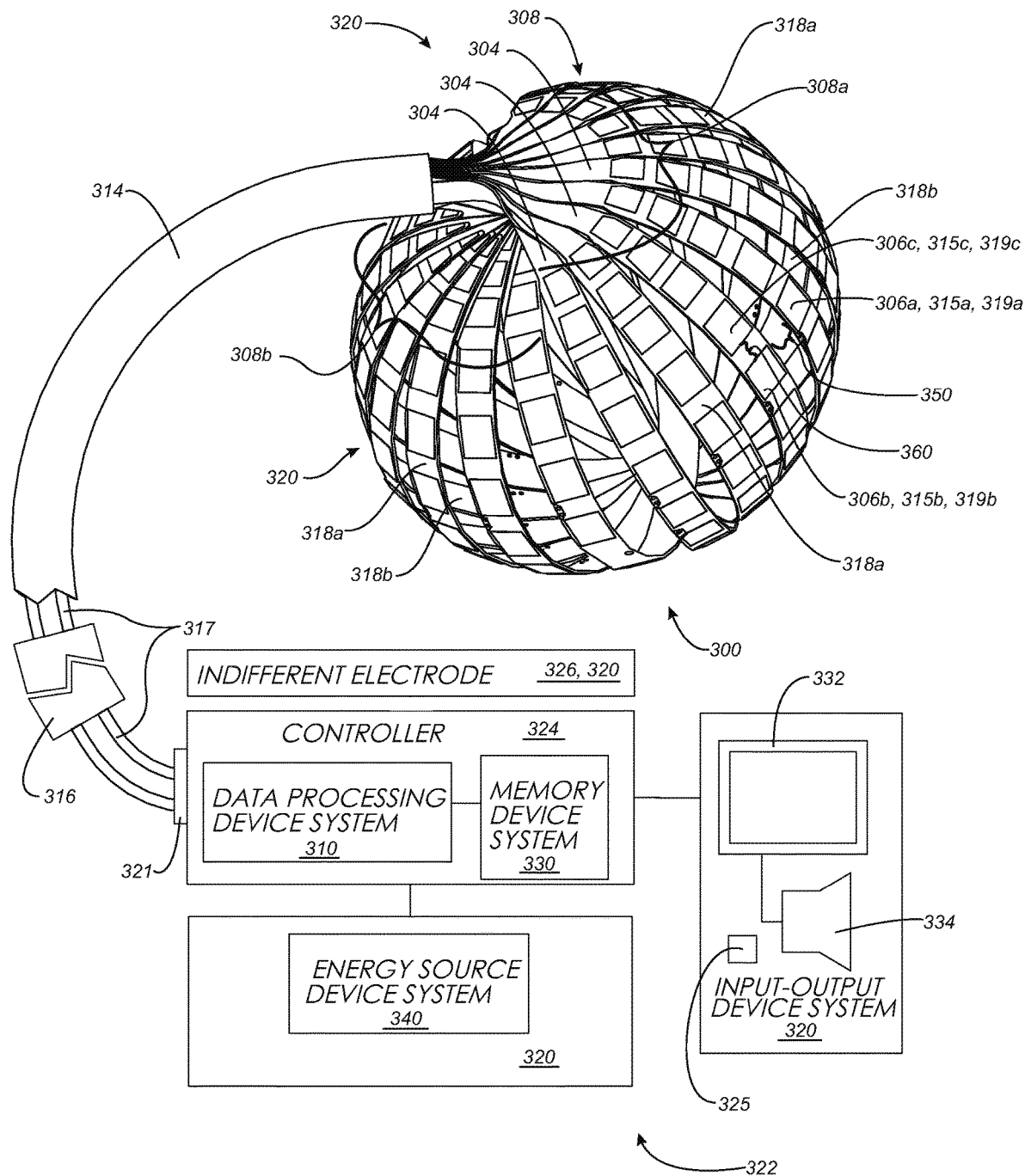
FIG. 3B is the representation of the medical device system of FIG. 3A with the expandable structure shown in a deployed or expanded configuration, according to some embodiments.
Figure 3C:
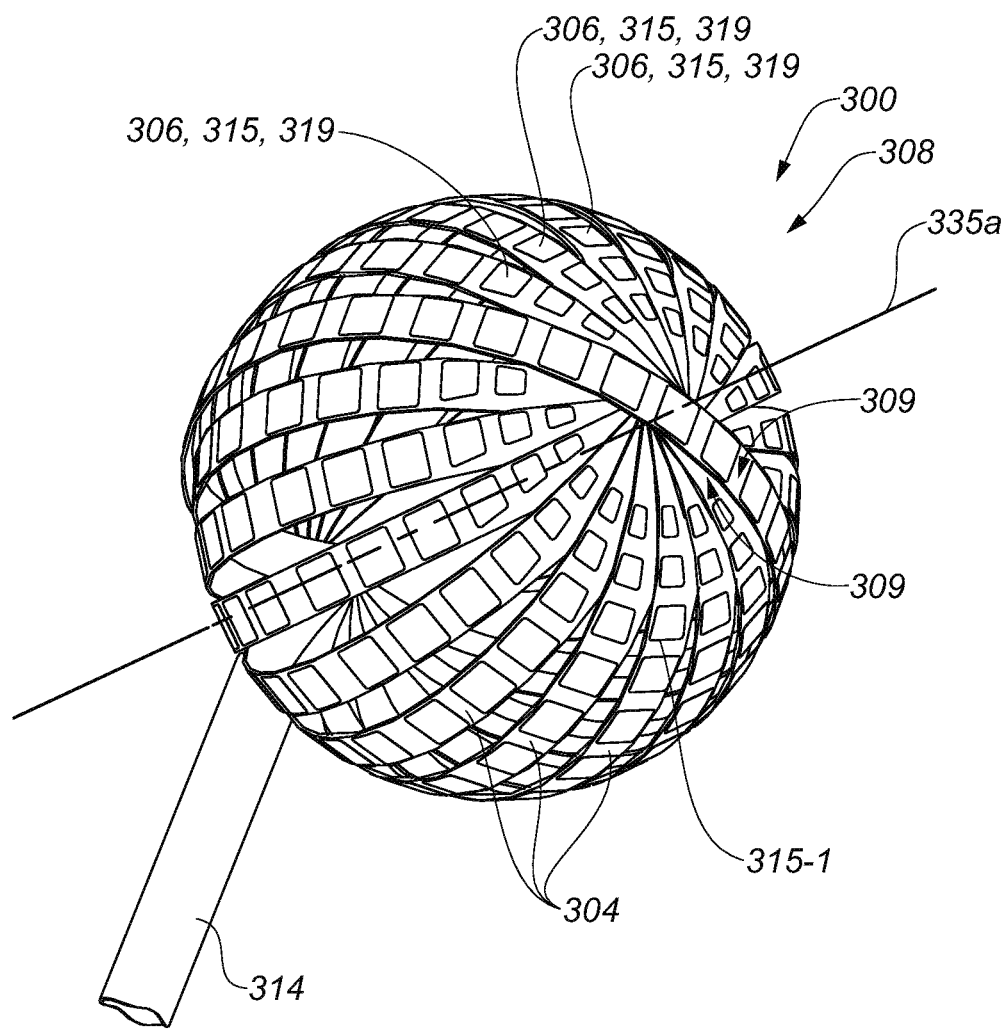
FIG. 3C is a representation of the expandable structure of the medical device system of FIG. 3A in the deployed or expanded configuration, as viewed from a different viewing angle than that employed in FIG. 3B, according to some embodiments.
Figure 3D:
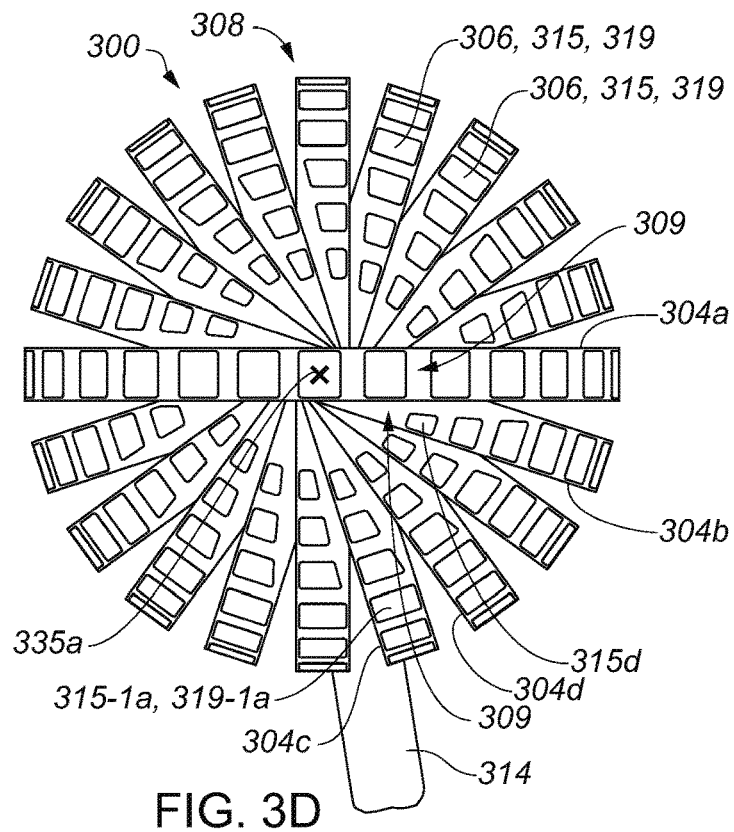
FIG. 3D is a plan view of the expandable structure of FIG. 3C, according to some embodiments.
Figure 3E:
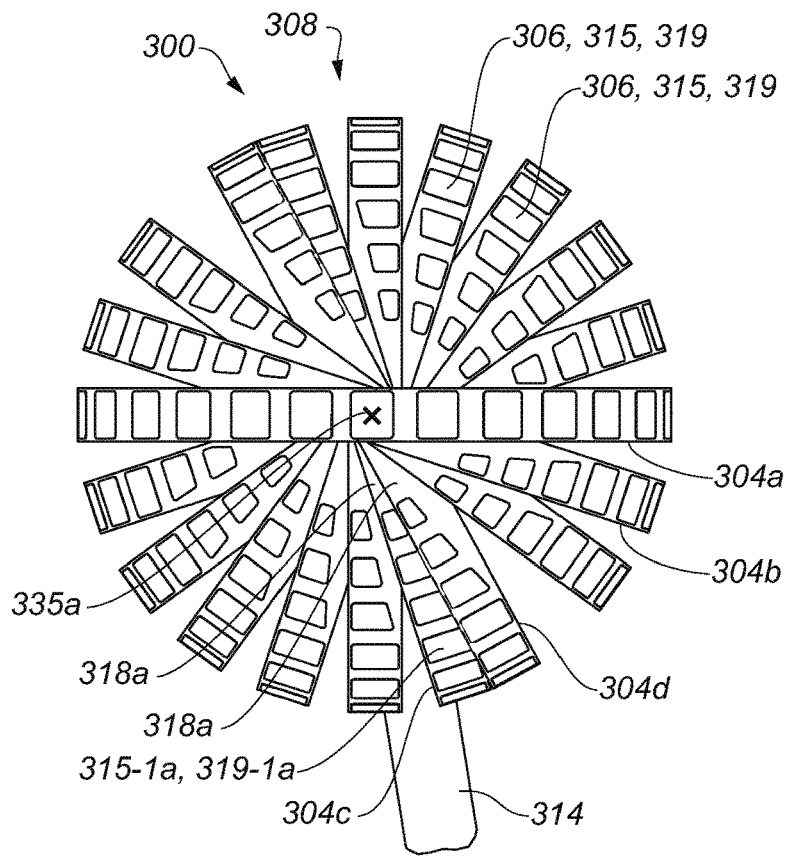
FIG. 3E is the plan view of FIG. 3D but with an improper positioning between various members of the structure, according to some embodiments.

Each of FIGS. 3A and 3B is a partially schematic representation of a medical device system, which may represent one or more implementations of the medical device system 100 of FIG. 1, according to some embodiments. In this regard, the medical device system illustrated in each of FIGS. 3A and 3B may be configured to detect a condition indicating a potentially improper energy transmission configuration, for example, when a transducer or an electrode thereof might be unable to properly transmit energy. Each of the medical device systems of FIGS. 3A and 3B includes an electrode-based device system 300, which is illustrated with different views in FIGS. 3C and 3D, according to some embodiments. The electrode-based device system 300 may include several hundred electrodes 315, but need not include that many. FIG. 3A illustrates the electrode-based device system 300 in the delivery or unexpanded configuration, according to various example embodiments, and each of FIGS. 3B, 3C, and 3D illustrates the electrode-based device system 300 in the deployed or expanded configuration, according to some embodiments. FIG. 3E illustrates the electrode-based device system 300 with an improper positioning between various members of the structure, according to some embodiments.

In this regard, the electrode-based device system 300 includes a plurality of elongate members 304 (three called out in each of FIGS. 3A and 3B, 3C, and four called out in each of FIG. 3D and FIG. 3E as 304a, 304b, 304c and 304d) and a plurality of transducers 306 (three called out in each of FIGS. 3A, 3C and 3D and three called out in FIG. 3B as 306a, 306b and 306c). In some embodiments, the transducers 306 have the configuration of the transducers 220 in FIG. 2. In some embodiments, the transducers 306 are formed as part of, or are located on, the elongate members 304. In some embodiments, the elongate members 304 are arranged as a frame or structure 308 that is selectively movable between an unexpanded or delivery configuration (e.g., as shown in FIG. 3A) and an expanded or deployed configuration (e.g., as shown in FIGS. 3B, 3C, and 3D) that may be used to position elongate members 304 against a tissue surface within the bodily cavity or position the elongate members 304 in the vicinity of, or in contact with, the tissue surface.

In some embodiments, the structure 308 has a size in the unexpanded or delivery configuration suitable for percutaneous delivery through a bodily opening (e.g., via catheter sheath 312, not shown in FIG. 3B) to the bodily cavity. In some embodiments, structure 308 has a size in the expanded or deployed configuration too large for percutaneous delivery through a bodily opening (e.g., via catheter sheath 312) to the bodily cavity. The elongate members 304 may form part of a flexible circuit structure (i.e., also known as a flexible printed circuit board (PCB) circuit). The elongate members 304 can include a plurality of different material layers, and each of the elongate members 304 can include a plurality of different material layers. The structure 308 can include a shape memory material, for instance Nitinol. The structure 308 can include a metallic material, for instance stainless steel, or non-metallic material, for instance polyimide, or both a metallic and non-metallic material by way of non-limiting example. The incorporation of a specific material into structure 308 may be motivated by various factors including the specific requirements of each of the unexpanded or delivery configuration and expanded or deployed configuration, the required position or orientation (i.e., pose) or both of structure 308 in the bodily cavity, or the requirements for successful ablation of a desired pattern.

The plurality of transducers 306 are positionable within a bodily cavity, for example, by positioning of the structure 308. For instance, in some embodiments, the transducers 306 are able to be positioned in a bodily cavity by movement into, within, or into and within the bodily cavity, with or without a change in a configuration of the plurality of transducers 306 (e.g., a change in a configuration of the structure 308 causes a change in configuration of the transducers 306 in some embodiments). In some embodiments, the plurality of transducers 306 are arrangeable to form a two- or three-dimensional distribution, grid or array capable of mapping, ablating or stimulating an inside surface of a bodily cavity or lumen without requiring mechanical scanning. As shown for example, in FIG. 3A, the plurality of transducers 306 are arranged in a distribution receivable in a bodily cavity (not shown in FIG. 3A). As shown for example, in FIG. 3A, the plurality of transducers 306 are arranged in a distribution suitable for delivery to a bodily cavity.

Figure 4:
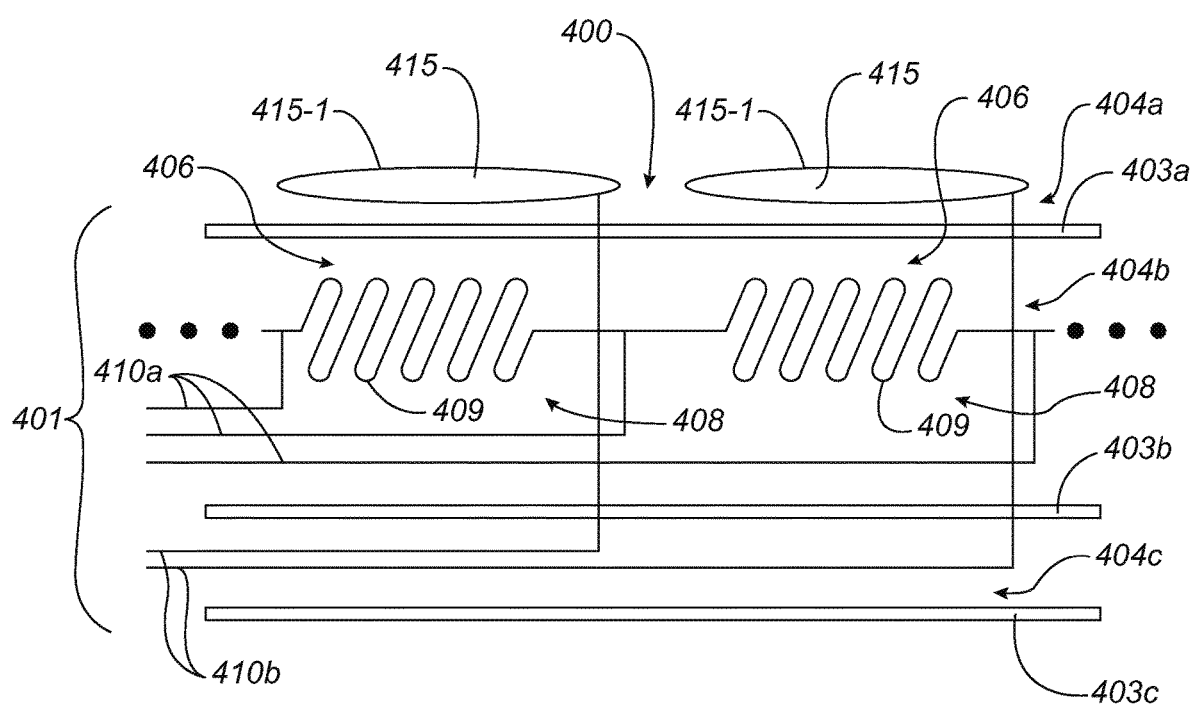
FIG. 4 illustrates a schematic representation of an electrode-based device that includes a flexible circuit structure, according to various example embodiments.

FIG. 4 is a schematic side elevation view of at least a portion of an electrode-based device system 400 that includes a flexible circuit structure 401 that is employed to provide a plurality of transducers 406 (two called out) according to various example embodiments. In some embodiments, the transducers 406 correspond to the transducers 306. In some embodiments, the flexible circuit structure 401 may form part of a structure (e.g., structure 308) that is selectively movable between a delivery configuration sized for percutaneous delivery and an expanded or deployed configuration sized too large for percutaneous delivery. In some embodiments, the flexible circuit structure 401 may be located on, or form at least part of, a structural component (e.g., elongate member 304) of an electrode-based device system (e.g., electrode-based device system 300).

The flexible circuit structure 401 may be formed by various techniques including flexible printed circuit techniques. In some embodiments, the flexible circuit structure 401 includes various layers including flexible layers 403 (three called out in FIG. 4 as reference symbols 403a, 403b and 403c). In some embodiments, each of the flexible layers 403 includes an electrical insulator material (e.g., polyimide). One or more of the flexible layers 403 may include a different material than another of the flexible layers 403. In some embodiments, the flexible circuit structure 401 includes various electrically conductive layers 404 (three called out in FIG. 4 as reference symbols 404a, 404b and 404c). The electrically conductive layers 404 may be interleaved with the flexible layers 403. In some embodiments, each of the electrically conductive layers 404 is patterned to form various electrically conductive elements. For example, electrically conductive layer 404a may be patterned to form a respective electrode 415 included as part of each of the transducers 406. Electrodes 415 may have respective electrode edges 415-1 that form a periphery of an electrically conductive surface or surface portion associated with the respective electrode 415. FIG. 3C shows another example of electrode edges 315-1 and illustrates that the electrode edges can define electrically-conductive-surface-peripheries of various shapes.

In some embodiments, the respective electrically conductive surface or surface portion of one or more of the electrodes 415 (or 315) is configured to transmit energy to contacting tissue at a level sufficient for ablation of the tissue. Other energy levels may be transmitted to, for example, provide stimulation (e.g., electrical stimulation that may include pinging or pacing) to tissue within a bodily cavity (e.g., left atrium 204), sense characteristics of tissue (e.g., electrophysiological activity, convective cooling, permittivity, force, temperature, impedance, thickness, or a combination thereof) within the bodily cavity, or a combination thereof.

Electrically conductive layer 404b is patterned, in some embodiments, to form respective temperature sensors 408 for each of the transducers 406 as well as various leads 410*a* arranged to provide electrical energy to the temperature sensors 408. In some embodiments, each temperature sensor 408 includes a patterned resistive member 409 (two called out) having a predetermined electrical resistance. In some embodiments, each resistive member 409 includes a metal having relatively high electrical conductivity characteristics (e.g., copper). In some embodiments, electrically conductive layer 404*c* is patterned to provide portions of various leads 410*b* arranged to provide an electrical communication path to electrodes 415. In some embodiments, leads 410*b* are arranged to pass though vias (not shown) in flexible layers 403*a* and 403*b* to connect with electrodes 415. Although FIG. 4 shows flexible layer 403*c* as being a bottom-most layer, some embodiments may include one or more additional layers underneath flexible layer 403*c*, such as one or more structural layers, such as a stainless steel or composite layer. These one or more structural layers, in some embodiments, are part of the flexible circuit structure 401 and can be part of, e.g., elongate member 304. In addition, although FIG. 4 shows only three flexible layers 403*a*-403*c* and only three electrically conductive layers 404*a*-404*c*, it should be noted that other numbers of flexible layers, other numbers of electrically conductive layers, or both, can be included.

In some embodiments, electrodes 415 are employed to selectively deliver RF energy to various tissue structures within a bodily cavity (not shown) (e.g., a tissue cavity such as an intra-cardiac cavity). The energy delivered to the tissue structures may be sufficient for ablating portions of the tissue structures. In various embodiments, the tissue structures are typically formed from non-fluidic tissue and the energy sufficient for ablating portions of the tissue structures is typically referred to as sufficient for tissue ablation. It is noted that energy sufficient for non-fluidic-tissue ablation may include energy levels sufficient to disrupt or alter fluidic tissue (e.g., blood) that may, for example, be located proximate the tissue structure. In many cases, the application of non-fluidic-tissue-ablative energy (i.e., energy that is sufficient to ablate non-fluidic tissue) to fluidic tissue, such as blood, is undesired when the energy is sufficient to disrupt or adversely impact a property of the fluidic tissue. For example, the application of non-fluidic-tissue-ablative energy to blood may be undesired when the energy is sufficient to cause various parts of the blood to coagulate in a process typically referred to as thermal coagulation. In this regard, some embodiments facilitate detection of conditions where an electrode configured to deliver non-fluidic-tissue-ablative energy may be in a configuration where it is not able to properly transmit such energy. In some embodiments, a detection of such a condition results in an error notification being transmitted or otherwise presented to a user or, in some embodiments, a restriction of that electrode from transmitting at least a portion of the non-fluidic-tissue-ablative energy. In some embodiments, a detection of such a condition results in an error notification being transmitted or otherwise presented to a user or, in some embodiments, a restriction of that electrode from being selected by a user action (e.g., a user selection of that electrode from a number of selectable electrodes to perform a particular function, such as transmitting at least a portion of the non-fluidic-tissue-ablative energy).

The energy delivered to the tissue may be delivered to cause monopolar tissue ablation, bipolar tissue ablation, or blended monopolar-bipolar tissue ablation by way of non-limiting example. In some embodiments, each electrode 415 is employed to sense an electrical potential in the tissue proximate the electrode 415. In some embodiments, each electrode 415 is employed in the generation of an intra-cardiac electrogram. In some embodiments, each resistive member 409 is positioned adjacent a respective one of the electrodes 415. In some embodiments, each of the resistive members 409 is positioned in a stacked or layered array with a respective one of the electrodes 415 to form a respective one of the transducers 406. In some embodiments, the resistive members 409 are connected in series to allow electrical current to pass through all of the resistive members 409. In some embodiments, leads 410*a* are arranged to allow for a sampling of electrical voltage between each resistive members 409. This arrangement allows for the electrical resistance of each resistive member 409 to be accurately determined. The ability to accurately determine the electrical resistance of each resistive member 409 may be motivated by various reasons including determining temperature values at locations at least proximate the resistive member 409 based at least on changes in the resistance caused by convective cooling effects (e.g., as provided by blood flow). In various embodiments, some of the transducers 406 are controlled to provide one or more electrical signals to tissue (e.g., non-fluidic tissue associated with a tissue wall or fluidic tissue such as blood) and information or a derivative thereof is determined in response to the provided signals, the information or the derivative thereof indicating a result of an interaction between the one or more signals and the tissue. In various ones of these embodiments, the one or more signals may include one or more energy levels insufficient for tissue ablation.

In some embodiments in which the electrode-based device system 200 or 300 is deployed in a bodily cavity (e.g., when the electrode-based device system 200 or 300 takes the form of a catheter device system arranged to be percutaneously or intravascularly delivered to a bodily cavity), it may be desirable to perform various mapping procedures in the bodily cavity. For example, when the bodily cavity is an intra-cardiac cavity, a desired mapping procedure can include mapping electrophysiological activity in the intra-cardiac cavity. Other desired mapping procedures can include mapping of various anatomical features within a bodily cavity. An example of the mapping performed by devices according to various embodiments may include locating the position of the ports of various bodily openings positioned in fluid communication with a bodily cavity. For example, in some embodiments, it may be desired to determine the locations of various ones of the pulmonary veins or the mitral valve that each interrupts an interior surface of an intra-cardiac cavity such as a left atrium.

In some example embodiments, the mapping is based at least on locating bodily openings by differentiating between fluid and non-fluidic tissue (e.g., tissue defining a surface of a bodily cavity). There are many ways to differentiate non-fluidic tissue from a fluid such as blood or to differentiate tissue from a bodily opening in case a fluid is not present. Four approaches may include by way of non-limiting example, and, depending upon the particular approach(es) chosen, the configuration transducers 406 in FIG. 4 may be implemented accordingly:

1. The use of convective cooling of heated transducer elements by fluid. An arrangement of slightly heated transducer elements that is positioned adjacent to the tissue that forms the interior surface(s) of a bodily cavity and across the ports of the bodily cavity will be cooler at the areas which are spanning the ports carrying the flow of fluid.

2. The use of tissue impedance measurements. A set of transducers positioned adjacently to tissue that forms the interior surface(s) of a bodily cavity and across the ports of the bodily cavity can be responsive to electrical tissue impedance. Typically, heart tissue will have higher associated tissue impedance values than the impedance values associated with blood.

3. The use of the differing change in dielectric constant as a function of frequency between blood and tissue. A set of transducers positioned around the tissue that forms the interior surface(s) of the atrium and across the ports of the atrium monitors the ratio of the dielectric constant from 1 KHz to 100 KHz. Such can be used to determine which of those transducers are not proximate to tissue, which is indicative of the locations of the ports.

4. The use of transducers that sense force (i.e., force sensors). A set of force detection transducers positioned around the tissue that forms the interior surface(s) of a bodily cavity and across the bodily openings or ports of the bodily cavity can be used to determine which of the transducers are not engaged with the tissue, which may be indicative of the locations of the ports.

Various ones of the above approaches may be used, at least in part, to determine proximity of a transducer to non-fluidic tissue or to fluidic tissue in some embodiments. Various ones of the above approaches may be used, at least in part, to determine contact between a transducer and non-fluidic tissue or contact between a transducer and fluidic tissue in some embodiments. Various ones of the above approaches may be used, at least in part, to determine an amount of an electrically conductive surface portion of an electrode that contacts non-fluidic tissue or contacts fluidic tissue in some embodiments. Various ones of the above approaches may be used, at least in part, to determine an amount of an electrically conductive surface portion of an electrode that is available to contact non-fluidic tissue or available to contact fluidic tissue in some embodiments, as discussed below.

Referring again to the medical device systems of FIGS. 3A and 3B, according to some embodiments, electrode-based device system 300 communicates with, receives power from or is controlled by a transducer-activation system 322, which may include a controller 324 and an energy source device system 340. In some embodiments, the controller 324 includes a data processing device system 310 and a memory device system 330 that stores data and instructions that are executable by the data processing device system 310 to process information received from other components of the medical device system of FIGS. 3A and 3B or to control operation of components of the medical device system of FIGS. 3A and 3B, for example by activating various selected transducers 306 to ablate tissue, sense tissue characteristics, et cetera. In this regard, the data processing device system 310 may correspond to at least part of the data processing device system 110 in FIG. 1, according to some embodiments, and the memory device system 330 may correspond to at least part of the memory device system 130 in FIG. 1, according to some embodiments. The energy source device system 340, in some embodiments, is part of an input-output device system 320, which may correspond to at least part of the input-output device system 120 in FIG. 1. Although only a single controller 324 is illustrated, it should be noted that such controller 324 may be implemented by a plurality of controllers. In some embodiments, the electrode-based device system 300 (or 200 in FIG. 2) is considered to be part of the input-output device system 320. The input-output device system 320 may also include a display device system 332, a speaker device system 334, or any other device such as those described above with respect to the input-output device system 120.

In some embodiments, elongate members 304 can form a portion or an extension of control leads 317 that reside, at least in part, in an elongated cable 316 and, at least in part, in a flexible catheter body 314. The control leads terminate at a connector 321 or other interface with the transducer-activation system 322 and provide communication pathways between at least the transducers 306 and the controller 324. The control leads 317 may correspond to electrical conductors 216 in some embodiments.

As discussed with respect to FIG. 4, each of various ones of the transducers 306, 406 includes an electrode 315, 415, according to some embodiments. In these various embodiments, each of at least some of the electrodes 315, 415 may include a respective energy transmission surface (e.g., energy transmission surface 319 in FIG. 3A) configured to transfer, transmit, or deliver energy, for example, to tissue. In some embodiments, at least some of the respective energy transmission surfaces are configured to receive energy, for example, from tissue. Each of the energy transmission surfaces may be bound by a respective electrode edge 315-1 (e.g., FIG. 3C), 415-1 (e.g., FIG. 4).

In various embodiments, each of the electrodes 315 includes an electrically conductive surface portion (e.g., energy transmission surface 319) that, in some embodiments, has an electrical conductivity that is typically greater than that of fluidic and non-fluidic tissue. In some embodiments, the entirety of the electrically conductive surface portion is configured to contact or is configured to be available or exposed for contact with a contiguous portion of a non-fluidic tissue surface (e.g., a tissue surface that defines a tissue wall). Complete contact between the entirety of the electrically conductive surface portion and the non-fluidic tissue may be motivated for different reasons. For example, various desired characteristics required in a lesion formed in a tissue wall in a tissue ablation procedure may be dependent on the degree of intimate contact established between the electrically conductive surface portion of the electrode 315 and the tissue wall. For example, intimate contact may be required to form a lesion having sufficient transmurality to act as an effective electrophysiological activity block (e.g., a block capable of forming a barrier to spurious electrical signals causing fibrillation in an atrium). In some cases, complete contact between the entirety of the electrically conductive surface portion and the non-fluidic tissue may be desired to reduce the time required to form a lesion to a desired tissue depth under the influence of a given ablation energy level. In some cases, complete contact between the entirety of the electrically conductive surface portion of the electrode 315 and the non-fluidic tissue may be desired to reduce transmission of ablative energy to a surrounding fluidic tissue. In some cases, complete contact between the entirety of the electrically conductive surface portion of the electrode 315 and the non-fluidic tissue may be desired to reduce or eliminate exposure of the electrically conductive surface portion of the electrode 315 to surrounding fluidic tissue when the electrically conductive surface portion of the electrode 315 is positioned in contact with non-fluidic tissue. In some embodiments, the entirety of the portion of the electrically conductive surface of the electrode 315 that is configured to contact or is configured to be available or exposed (e.g., without some obstruction preventing at least some of the ability) to contact a tissue wall surface includes all of the electrically conductive surface. For example, this may occur when the electrically conductive surface has a generally planar form (e.g., a generally planar conductive surface provided by an electrode formed by flexible circuit fabrication techniques (e.g., electrode 415)). In some embodiments, the entirety of the portion of the electrically conductive surface of the electrode that is configured to contact or is configured to be available or exposed to contact a tissue wall surface includes some, but not all, of the electrically conductive surface. For example, this may occur when the electrode has a generally three-dimensional surface (e.g., a surface having a cylindrical, hemi-spherical or other three-dimensional form) with only a portion less than the entirety of the three-dimensional surface configured to contact or configured to be available or exposed for contact with a tissue surface wall.

In some embodiments, input-output device system 320 may include a sensing device system 325 configured to detect various characteristics or conditions including, but not limited to, at least one of tissue characteristics (e.g., electrical characteristics such as tissue impedance, tissue type, tissue thickness) and thermal characteristics such as temperature. Various other particular conditions described later in this disclosure may be detected by sensing device system 325 according to various embodiments. It is noted that in some embodiments, sensing device system 325 includes various sensing devices or transducers configured to sense or detect a particular condition while positioned within a bodily cavity. In some embodiments, at least part of the sensing device system 325 may be provided by electrode-based device system 300 (e.g., various ones of transducers 306). In some embodiments, sensing device system 325 includes various sensing devices or transducers configured to sense or detect a particular condition while positioned outside a given bodily cavity or even outside a body that includes the bodily cavity. In some embodiments, the sensing device system 325 may include an ultrasound device system or a fluoroscopy device system or portions thereof by way of non-limiting example.

The energy source device system 340 may, for example, be connected to various selected transducers 306 or their respective electrodes 315 to provide energy in the form of electrical current or energy (e.g., RF energy) to the various selected transducers 306 or their respective electrodes 315 to cause ablation of tissue. In this regard, although FIGS. 3A and 3B show a communicative connection between the energy source device system 340 and the controller 324 (and its data processing device system 310), the energy source device system 340 may also be connected to the transducers 306 or their respective electrodes 315 via a communicative connection that is independent of the communicative connection with the controller 324 (and its data processing device system 310). For example, the energy source device system 340 may receive control signals via the communicative connection with the controller 324 (and its data processing device system 310), and, in response to such control signals, deliver energy to, receive energy from, or both deliver energy to and receive energy from one or more of the transducers 306 via a communicative connection with such transducers 306 or their respective electrodes 315 (e.g., via one or more communication lines through catheter body 314, elongated cable 316 or catheter sheath) that does not pass through the controller 324. In this regard, the energy source device system 340 may provide results of its delivering energy to, receiving energy from, or both delivering energy to and receiving energy from one or more of the transducers 306 or the respective electrodes 315 to the controller 324 (and its data processing device system 310) via the communicative connection between the energy source device system 340 and the controller 324.

The energy source device system 340 may, for example, provide energy in the form of electrical current to various selected transducers 306 or their respective electrodes 315. Determination of a temperature characteristic, an electrical characteristic, or both, at a respective location at least proximate each of the various transducers 306 or their respective electrodes 315 may be made under the influence of energy or current provided by the energy source device system 340 in various embodiments. Energy provided to an electrode 315 by the energy source device system 340 may in turn be transmittable by the electrodes 315 to adjacent tissue (e.g., tissue forming a tissue wall surface). In various embodiments, the transmittable energy is sufficient for tissue ablation. In some embodiments, the energy is insufficient for tissue ablation. The energy source device system 340 may include various electrical current sources or electrical power sources. In some embodiments, an indifferent electrode 326 is provided to receive at least a portion of the energy transmitted by at least some of the transducers 306 or their respective electrodes 315. Consequently, although not shown in FIGS. 3A and 3B, the indifferent electrode may be communicatively connected to the energy source device system 340 via one or more communication lines in some embodiments. The indifferent electrode 326 is typically configured to be positioned outside of a bodily cavity and may be positioned on an exterior body surface and, in some embodiments, although shown separately in FIGS. 3A and 3B, is considered part of the energy source device system 340.

Structure 308 can be delivered and retrieved via a catheter member, for example, a catheter sheath 312. In some embodiments, the structure 308 provides expansion and contraction capabilities for a portion of a medical device (e.g., an arrangement, distribution or array of transducers 306). The transducers 306 can form part of, be positioned or located on, mounted or otherwise carried on the structure 308 and the structure may be configurable to be appropriately sized to slide within catheter sheath 312 in order to be deployed percutaneously or intravascularly. FIG. 3A shows one embodiment of such a structure, where the elongate members 304, in some embodiments, are stacked in the delivery or unexpanded configuration to facilitate fitting within the flexible catheter sheath 312. In some embodiments, each of the elongate members 304 includes a respective distal end 305 (only one called out in FIG. 3A), a respective proximal end 307 (only one called out in FIG. 3A) and an intermediate portion 309 (only one called out in FIG. 3A, but two are called out in each of FIGS. 3C and 3D) positioned between the proximal end 307 and the distal end 305. Correspondingly, in some embodiments, structure 308 includes a proximal portion 308a and a distal portion 308b. In some embodiments, the proximal and the distal portions 308a, 308b include respective portions of elongate members 304. The respective intermediate portion 309 of each elongate member 304 may include a first or front surface 318a that is positionable to face an interior tissue surface within a bodily cavity (not shown) and a second or back surface 318b opposite across a thickness of the intermediate portion 309 from the front surface 318a. In some embodiments, each elongate member 304 includes a twisted portion at a location proximate proximal end 307. Similar twisted portions are described in co-assigned International Application No.: PCT/US2012/022062.

The transducers 306 can be arranged in various distributions or arrangements in various embodiments. In some embodiments, various ones of the transducers 306 are spaced apart from one another in a spaced apart distribution as shown, for example in at least FIGS. 3A and 3B. In some embodiments, various regions of space are located between various pairs of the transducers 306. For example, in FIG. 3B the electrode-based device system 300 includes at least a first transducer 306a, a second transducer 306b and a third transducer 306c (all collectively referred to as transducers 306). In some embodiments each of the first, the second, and the third transducers 306a, 306b and 306c are adjacent transducers in the spaced apart distribution. In some embodiments, the first and the second transducers 306a, 306b are located on different elongate members 304 while the second and the third transducers 306b, 306c are located on a same elongate member 304. In some embodiments, a first region of space 350 is between the first and the second transducers 306a, 306b. In some embodiments, the first region of space 350 is not associated with any physical portion of structure 308. In some embodiments, a second region of space 360 associated with a physical portion of device system 300 (e.g., a portion of an elongate member 304) is between the second and the third transducers 306b, 306c. In some embodiments, each of the first and the second regions of space 350, 360 does not include a transducer or electrode thereof of electrode-based device system 300. In some embodiments, each of the first and the second regions of space 350, 360 does not include any transducer or electrode.

It is noted that other embodiments need not employ a group of elongate members 304 as employed in the illustrated figures. For example, other embodiments may employ a structure having one or more surfaces, at least a portion of the one or more surfaces defining one or more openings in the structure. In these embodiments, a region of space not associated with any physical portion of the structure may extend over at least part of an opening of the one or more openings. In other example embodiments, other structures may be employed to support or carry transducers of a transducer-based device such as a transducer-based catheter. For example, an elongated catheter member may be used to distribute the transducers in a linear or curvilinear array. Basket catheters or balloon catheters may be used to distribute the transducers in a two-dimensional or three-dimensional array.

In various example embodiments, the energy transmission surface 319 of each electrode 315 is provided by an electrically conductive surface. In some embodiments, each of the electrodes 315 is located on various surfaces of an elongate member 304 (e.g., front surfaces 318a or back surfaces 318b). In some embodiments, various electrodes 315 are located on one, but not both of the respective front surface 318a and respective back surface 318b of each of various ones of the elongate members 304. For example, various electrodes 315 may be located only on the respective front surfaces 318a of each of the various ones of the elongate members 304. Three of the electrodes 315 are identified as electrodes 315a, 315b and 315c in FIG. 3B. Three of the energy transmission surfaces 319 are identified as 319a, 319b and 319c in FIG. 3B. In various embodiments, it is intended or designed to have the entirety of each of various ones of the energy transmission surfaces 319 be available or exposed (e.g., without some obstruction preventing at least some of the ability) to contact non-fluid tissue at least when structure 308 is positioned in a bodily cavity in the expanded configuration. In various embodiments, it is intended or designed to have no portion of each of at least one of the energy transmission surfaces 319 contact fluidic tissue when the at least one of the energy transmission surfaces 319 contacts a contiguous portion of a non-fluidic tissue surface (e.g., a tissue surface that defines a tissue wall).

FIG. 3C is a perspective view of the expandable structure 308 of the medical device system of FIG. 3A in the expanded or deployed configuration, as viewed from a different viewing angle than that employed in FIG. 3B, according to some embodiments. For clarity of illustration, only structure 308 including various ones of the elongate members 304, and a portion of catheter body 314 are shown in FIG. 3C. In some embodiments, the respective intermediate portions 309 (only two called out) of various ones of the elongate members 304 are angularly arranged with respect to one another about a first axis 335a when structure 308 is in the deployed configuration.

FIG. 3D is a plan view of structure 308 in the deployed or expanded configuration of FIG. 3C. The plan view of FIG. 3D has an orientation such that the first axis 335a is viewed along the axis in this particular embodiment. First axis 335a is represented by an "x" symbol in FIG. 3D as entering and coming out of the page. It is understood that the depicted symbol "x" used to represent first axis 335a does not impart any size or shape attributes to the first axis 335a.

In various embodiments, at least some of the transducers 306 are radially spaced about first axis 335a when structure 308 is in the deployed configuration. For example, various ones of the electrodes 315 are radially spaced about first axis 335a in the deployed configuration in at least some of the embodiments associated with various ones of FIGS. 3B, 3C, 3D and 3E. In various embodiments, at least some of the transducers 306 are circumferentially arranged about first axis 335a when structure 308 is in the deployed configuration. For example, various ones of the electrodes 315 are circumferentially arranged about first axis 335a in the deployed configuration in at least some of the embodiments associated with various ones of FIGS. 3B, 3C, 3D and 3E. It is understood that although electrodes are referred to in these described embodiments, the same analysis applies to the corresponding transducers in some embodiments.

It may be noted that distances between adjacent ones of the elongate members 304 shown in FIGS. 3B 3C, 3D and 3E vary as elongate members 304 extend towards first axis 335a when structure 308 is in the deployed configuration. In some cases, the varying distances between adjacent elongate members 304 in the deployed configuration may give rise to shape, size or dimensional constraints for the electrodes 315 located on the elongate members 304. In some cases, the overlapping portions of various ones of the elongate members 304 in the deployed configuration may give rise to shape, size or dimensional constraints for the electrodes 315 located on the portions of the various ones of the elongate members 304. For example, it may be desirable to reduce a surface area of an electrode adjacent an overlap region on an overlapped elongate member to accommodate the reduced-exposed-surface area of the overlapped elongate member in the region adjacent the overlap region (e.g., electrode 315d in FIG. 3D).

In various embodiments, the respective shape of various electrically conductive surfaces (e.g., energy transmission surfaces 319) of various ones of the electrodes 315 vary among the electrodes 315. In various embodiments, the respective shape of various electrically conductive surfaces (e.g., energy transmission surfaces 319) of various ones of the electrodes 315 vary among the electrodes 315 in accordance with their proximity to first axis 335a. In various embodiments, one or more dimensions or sizes of various electrically conductive surfaces (e.g., energy transmission surfaces 319) of at least some of the electrodes 315 vary among the electrodes 315. In various embodiments, one or more dimensional sizes of various electrically conductive surfaces (e.g., energy transmission surfaces 319) of at least some of the electrodes 315 vary in accordance with their proximity to first axis 335a. The shape or size variances associated with various ones of the electrodes 315 may be motivated for various reasons. For example, in various embodiments, the shapes or sizes of various ones of the electrodes 315 may be controlled in response to various ones of the aforementioned size or dimensional constraints.

Figure 5A:
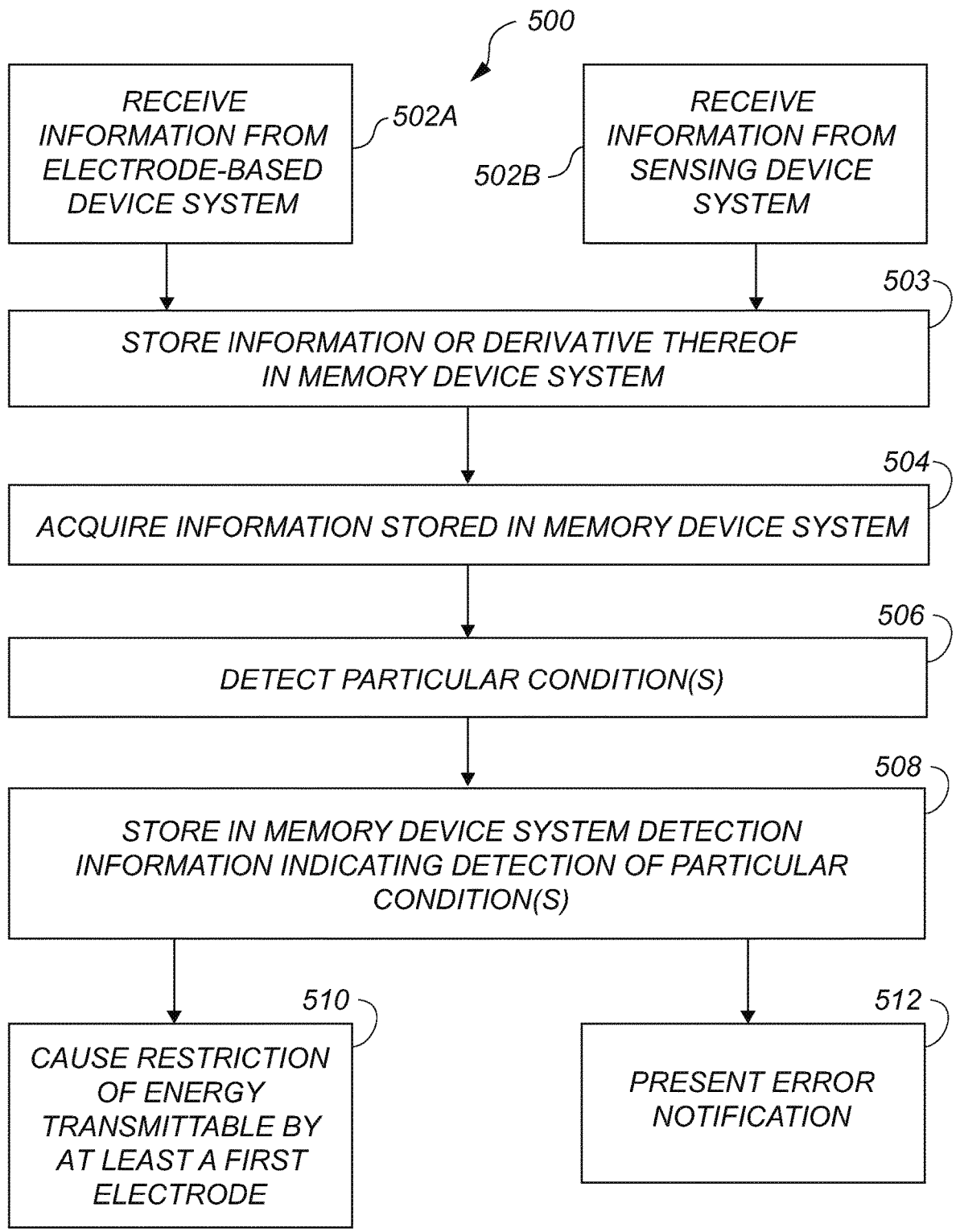
FIG. 5A is a block diagram of a method employed in various embodiments, the method including detecting one or more particular conditions associated with at least one electrode of an electrode-based device system, according to some embodiments.

FIG. 5A is a block diagram of a method 500 employed according to some example embodiments, while FIGS. 5B-5H represent exploded views of some of the blocks shown in FIG. 5A, according to various embodiments. One or more of the methods of FIGS. 5A-5H may be executed or implemented at least by one or more of the components of the system 100 of FIG. 1 or the systems of FIGS. 3A and 3B. For example, in some embodiments, a memory device system (e.g., memory device systems 130 or 330) is communicatively connected to a data processing device system (e.g., data processing device systems 110 or 310) and stores a program executable by the data processing device system to cause the data processing device system to execute one or more of the methods of FIGS. 5A-5H via interaction with at least, for example, an electrode-based device system (e.g., electrode-based device system 200 or 300) or sensing device system (e.g., 325) or data provided by such an electrode-based device system or sensing device system. In these various embodiments, the program may include instructions configured to perform, or cause to be performed, the tasks or processes associated with one or more of the blocks in one or more of the methods illustrated in FIGS. 5A-5H. In some embodiments, method 500 including its exploded examples in FIGS. 5B-5H may include a subset of the associated blocks or additional blocks as compared to those shown in the respective figures. In some embodiments, method 500 including its exploded examples in FIGS. 5B-5H may include a different sequence between various ones of the associated blocks as compared to that shown in the respective figures.

In regard to FIG. 5A, block 504 is associated with acquisition instructions configured to acquire information stored in the memory device system, according to some embodiments. The information stored in the memory device system may be provided to the memory device system in various ways. For example, in some embodiments, an input-output device system (e.g., 120 or 320) may be communicatively connected to the memory device system (possibly by way of the data processing device system) and, consequently, may provide the information that is stored in the memory device system according to storage instructions associated with block 503. In this regard, the input-output device system may include an electrode-based device system (e.g., 200 or 300) that provides the information, which may be received by the data processing device system according to reception instructions associated with block 502A and stored in the memory device system according to the storage instructions associated with block 503. In some embodiments, the input-output device system includes a sensing device system (e.g., 325) that provides the information, which may be received by the data processing device system according to reception instructions associated with block 502B and stored in the memory device system according to the storage instructions associated with block 503. However, the input-output device system need not include an electrode-based device system or a sensing device system, and, in this regard, the information stored according to the instructions associated with block 503 may be information that originated at an electrode-based device system or a sensing device system, but reached the memory device system indirectly from some other source. For example, an electrode-based device system (e.g., 200 or 300) may be in wireless communication with a transceiver that is part of the input-output device system (e.g., 120), and this transceiver provides information from the electrode-based device system for storage in the memory device system according to the instructions associated with block 503. For another example, a user monitoring the electrode-based device system may merely manually input information from the electrode-based device system into an interface terminal of the input-output device system (e.g., 120), which is then received by the data processing device system (e.g., 110) and stored in the memory device system (e.g., 130) according to the instructions associated with block 503.

In embodiments where block 502A is used, the electrode-based device system may be configured to provide to the data processing device system information in the form of one or more electrical signals from its transducers (e.g., transducers 206, 306 or 406) while positioned in the bodily cavity. In some embodiments, the one or more electrical signals are provided to tissue (e.g., non-fluidic tissue making up a tissue wall or fluidic tissue such a blood). In some embodiments, the information stored according to the instructions associated with block 503 indicates a result of an interaction between the one or more electrical signals and the tissue. The one or more electrical signals may include or be limited to levels insufficient for tissue ablation. In some embodiments, the interaction between the one or more electrical signals and the tissue may be an electrical interaction. For example, the information stored in the memory device system according to the storage instructions associated with block 503 may include electrical impedance information determined from the interaction.

In embodiments where block 502B is used, it should be noted that the sensing device system (e.g., 325) may include a portion of an electrode-based device system (e.g., electrode-based device system 200 or 300) that is positionable in a particular bodily cavity. In some embodiments, the sensing device system 325 may include various transducers (e.g., emitters, detectors, et cetera) positionable outside the bodily cavity or even outside the body. In some embodiments, the sensing device system 325 may include an ultrasound device system or a fluoroscopy device system or portions thereof by way of non-limiting example.

Accordingly, the information acquired according to the instructions associated with block 504 may be any information that facilitates detection of a condition detected according to the instructions associated with block 506, discussed below. For example, the information acquired according to block 504 may include impedance information, positional information, fluid flow information, convective heat information, temperature information, or a combination of these items, and such information may be provided by the electrode-based device system (e.g., block 502A), the sensing device system (e.g., block 502B), or both.

In this regard, block 506 of method 500 is associated with detection instructions configured to detect a particular condition or conditions based on an analysis of the information acquired according to the acquisition instructions associated with block 504. In some embodiments, the analysis is based at least upon user input, although user input is not required. For example, in some embodiment, the particular condition or conditions may be detected by the data processing device system 110 merely based on the information received from the electrode-based device system (e.g., block 502A), the sensing device system (e.g., block 502B), or both. However, in some embodiments, the particular condition or conditions may be detected or otherwise identified by the data processing device system 110 based at least on or at least under the instruction of user input. For example, in a case where at least some of the information from block 502A, 502B, or both, is being presented to the user via input-output device system 120, the user may review this information and, consequently, at least assist in detecting the particular condition or conditions (for example, by providing input to the data processing device system 110 via input-output device system 120). The particular condition or conditions may be indicative of an improper energy transmission or delivery configuration where energy intended to be transmitted or delivered to one location could instead be delivered to another location and, in some medical device embodiments, might lead to an undesired result. Various conditions that may be caused to be detected under the influence of the detection instructions associated with block 506 are described later in this disclosure.

In some embodiments, the information received from the electrode-based device system (e.g., block 502A), the sensing device system (e.g., block 502B), or both is limited to information derived from energy levels insufficient to cause tissue ablation. For example, in some embodiments, the electrode-based device system may emit, from one or more transducers (or a respective electrode thereof), electrical signals having respective energy levels insufficient to cause tissue ablation. In some of these embodiments, the electrode-based device system may emit, from one or more transducers (or a respective electrode thereof), electrical signals having respective energy levels insufficient to cause ablation of non-fluidic tissue. In some of these embodiments, the electrode-based device system may emit, from one or more transducers (or a respective electrode thereof), electrical signals having respective energy levels insufficient to cause ablation of fluidic tissue (e.g., thermal coagulation of blood). The electrode-based device system may then detect results of an interaction between tissue and the electrical signals, and such detection results may be received according to the instructions associated with block 502A, in some embodiments. In this example, one or more particular conditions may be detected according to the instructions associated with block 506 based at least upon an analysis of such detection results. Accordingly, in some embodiments, the particular condition(s) may be detected according to the instructions associated with block 506 (including sub-block 506A, sub-block 506B, sub-block 506C, sub-block 506D, sub-block 506F, sub-block 506G, or a combination of two or more of these sub-blocks, which are discussed below) at a time when energy levels insufficient to cause tissue ablation are being applied (e.g., by one or more electrodes of the electrode-based device system or otherwise by another device). In this regard, in some embodiments, the particular condition(s) may be detected according to the instructions associated with block 506 (including sub-block 506A, sub-block 506B, sub-block 506C, sub-block 506D, sub-block 506F, sub-block 506G, or a combination of two or more of these sub-blocks, which are discussed below) at a time when energy levels sufficient to cause tissue ablation have not been applied (e.g., since the electrode-based device system or structure thereof was last placed in an expanded or deployed configuration), are not being applied (e.g., as part of unipolar or bipolar or other ablation), or both have not been applied and are not being applied (e.g., by one or more electrodes of the electrode-based device system or otherwise by another device). However, some embodiments are not limited to situations where energy (e.g., radiation) levels insufficient to cause tissue ablation are used to generate information received according to instructions associated with block 502A, 502B, or both 502A and 502B to detect the particular condition(s) according to block 506.

In some embodiments, block 508 of method 500 is associated with storage instructions configured to cause a storage in the memory device system (e.g., 130 in FIG. 1) of detection information indicating a detection of the particular condition or conditions detected according to the detection instructions associated with block 504.

Upon a detection or determination of the particular condition(s) according to the instructions associated with block 506, a result of such detection or determination may be stored in the memory device system (e.g., 130 in FIG. 1) according to the instructions associated with block 508 in FIG. 5A. Such detection or determination may also lead to the presenting of an error notification according to the instructions associated with block 512 or a restriction of energy transmittable by one or more electrodes according to the instructions associated with block 510 in FIG. 5A, according to some embodiments.

In this regard, the method 500 may include restriction instructions (e.g., associated with block 510 in FIG. 5A) configured to control the data processing device system to cause a restriction of energy transmittable by at least a first electrode in response to the particular condition(s) detected according to the detection instructions associated with block 506. In some embodiments, the energy transmittable by the first electrode is restricted to one or more levels insufficient for tissue ablation. In some embodiments, the energy transmittable by the first electrode is restricted to levels insufficient for detection at various locations at least proximate the first electrode. In some embodiments, the data processing device system causes, under the influence of the restriction instructions, a restriction or prevention of a flow of energy between an energy source device system (e.g., energy source device system 340) and the first electrode. In this regard, detection of a condition that may be indicative of an improper energy transmission or delivery configuration where energy intended to be transmitted or delivered to one location could instead be delivered to another location may result in prevention of energy delivery or at least restriction of energy delivery to a level configured to prevent an undesired outcome. In some embodiments, where the particular condition(s) is/are detected according to the instructions associated with block 506 at a time when energy levels sufficient to cause tissue ablation have not been applied, are not being applied, or both have not been applied and are not being applied, the restriction instructions (or "prevention instructions") associated with block 510 are configured to prevent energy sufficient to cause tissue ablation from being subsequently initiated or otherwise transmitted, e.g., from one or more transducers (or respective electrode thereof) implicated by one or more detected particular conditions, at least until the occurrence of an event, such as one or more detected conditions no longer being detected (e.g., one or more of the conditions previously detected according to the instructions associated with block 506 no longer being detected according to such instructions associated with block 506), the expiration of a predetermined period of time, or some other event. When the shunt condition is no longer detected, the implicated transducer(s) (or respective electrode thereof) may be permitted or allowed (e.g., according to "permission instructions") to initiate or otherwise transmit energy levels sufficient for tissue ablation.

In some embodiments, method 500 includes failure state instructions (e.g., associated with block 512 in FIG. 5A) configured to cause the input-output device system to present an error notification to a user in response to the particular condition(s) being detected according to the detection instructions associated with block 506. The error notification may be provided visually to the user via a display device system (e.g., display device system 332) or audibly via a speaker device system (e.g., speaker device system 334) by way of non-limiting example. In this regard, detection of a condition that may be indicative of an improper energy transmission or delivery configuration where energy intended to be transmitted or delivered to one location could instead be delivered to another location may result in a user being notified at least of the potential for improper operation.

Figure 5B:
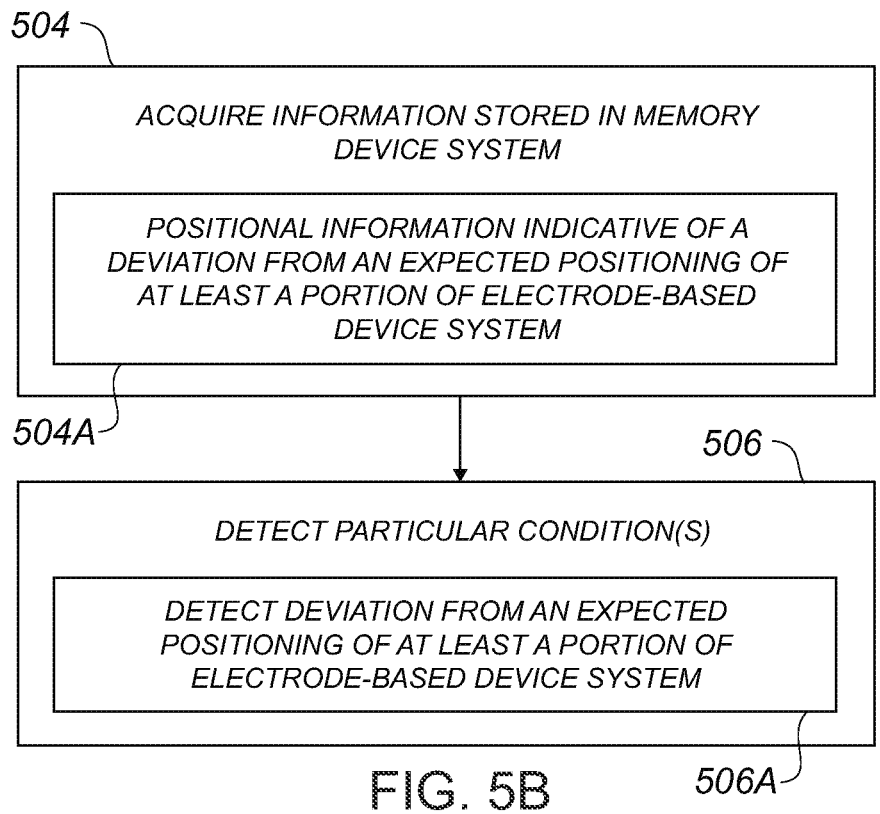
FIG. 5B is an exploded view of some of the blocks of the block diagram of FIG. 5A according to some example embodiments, some of the exploded blocks associated with a detection of a condition indicating a deviation from an expected positioning of at least a portion of an electrode-based device system, according to some embodiments.

Turning now to FIG. 5B, an exploded view, according to some embodiments, of steps 504 and 506 of FIG. 5A is illustrated. In this regard, FIG. 5B illustrates with block 504A that, in some embodiments, the information acquired according to the acquisition instructions associated with block 504 includes positional information indicative of a deviation from an expected positioning of the electrode-based device system (e.g., 200 or 300). In some embodiments, the instructions associated with block 506 can include, as illustrated with block 506A, instructions configured to cause detection of such a deviation from expected positioning of the electrode-based device system, based on an analysis of the positional information acquired according to block 504A. In some embodiments, the analysis is based at least upon user input, although user input is not required. It should be noted that although block 504A is illustrated in the context of FIG. 5B as example embodiments of FIG. 5A, block 504A could be applied to any of the embodiments of FIGS. 5C-5H as well.

In some embodiments, the expected positioning of the electrode-based device system is an intended, designed, or proper operational state of the electrode-based device system. Of course, a device system, such as the electrode-based device system, may have many intended, designed, or proper operational states, and, in this regard, the expected positioning may be a subset of these states and may depend upon the device system's environment and one or more particular or selected functions of the device system.

For example, in some embodiments, FIG. 3D illustrates one intended, designed, or proper operational state of the electrode-based device system 300 that might exist when such system 300 is not subject to external forces, such as that from a tissue wall pressing against some elongate members 304. Of course, the system 300 also is intended or designed to properly operate in conditions where the system 300 is deformed due to, e.g., a tissue wall pressing against at least some elongate members in some embodiments. Accordingly, in some embodiments, when it is known that the system 300 is deployed in a left atrium of a human heart that is somewhat smaller than the system 300 in a deployed configuration, it might be expected that the system 300 will experience some deformation, but not to a point where various ones of the electrodes 315 are contacting a physical portion of the electrode-based device system 300 (instead of being available to contact tissue (e.g., tissue forming a tissue wall). In these cases, an expected positioning of the electrode-based device system might be that none of the various ones of the electrodes are contacting a physical portion of the electrode-based device system 300, according to some embodiments. In some embodiments, situations may arise in which various ones of the electrodes 315 are not contacting a physical portion of the electrode-based device system 300, but, rather, are improperly positioned too close to the physical portion of the electrode-based device system 300 in a manner that could negatively impact energy delivery characteristics of the various ones of the electrodes 315. In these cases, a desired or an expected positioning of the electrode-based device system might be that none of the various ones of the electrodes are too close to a physical portion of the electrode-based device system 300, according to some embodiments.

Similarly, the expected positioning of the electrode-based device system might be based on a particular function or functions of the device system. For example, in some embodiments, if an ablative-energy-delivery function of the electrode-based device system is deemed of interest (e.g., by an operator), the expected positioning of the electrode-based device system may be defined in terms of this function, for example, by defining the expected positioning to be a configuration that allows the electrodes to properly deliver or transmit their respective ablative energies. Accordingly, the definition of expected positioning of at least a portion of the electrode-based device system may be selected to fit particular circumstances.

Deviations from expected positioning need not only arise due to deformation of the electrode-based device system 300, but can also arise for other reasons. For example, an improper positioning of a portion of the electrode-based device system 300 may occur when the structure 308 is moved between a delivery configuration and a deployed configuration. In this regard, FIG. 3E provides an example of a deviation in an expected positioning between a first electrode 315-1a and a physical portion (e.g., an elongate member 304) of the electrode-based device system 300 when the structure 308 on which the first electrode 315-1a is located is positioned in the deployed configuration. It is understood that reference to electrode 315-1a as the first electrode in various embodiments herein described in this disclosure is made for convenience of discussion and any electrode described as a first electrode in the various embodiments may include electrodes other than electrode 315-1a (e.g., any of electrodes 315, 415 by way of non-limiting example). In FIG. 3E, first electrode 315-1a is located on an elongate member 304c. As compared with an expected positioning between the first electrode 315-1a and elongate member 304d shown in FIG. 3D, a deviation in the expected positioning between first electrode 315-1a and the elongate member 304d is shown in FIG. 3E. In this case, the deviation in the expected positioning between first electrode 315-1a and the elongate member 304d occurs when structure 308 is in the deployed configuration. In FIG. 3E, elongate member 304d is positioned such that it overlaps at least a portion of the first electrode 315-1a. Varying degrees or amounts of overlap may occur. In FIG. 3E, elongate member 304d is positioned such that it overlaps some, but not all, of an electrically conductive surface portion (e.g., energy transmission surface 319-1a) associated with first electrode 315-1a of elongate member 304c. In some embodiments, at least an overlapping portion of the overlapping member 304d may be positioned between adjacent non-fluidic tissue and at least an overlapped portion of the overlapped member 304c, such as an overlapped portion of the electrically conductive surface portion (e.g., energy transmission surface 319-1a) associated with first electrode 315-1a. The deviation in the expected positioning between the first electrode 315-1a and the elongate member 304d may arise from an improper positioning of (a) the first electrode 315-1a (e.g., via an improper positioning of elongate member 304c), (b) an improper positioning of elongate member 304d, or both (a) and (b). In this particular case, the deviation in the expected positioning between the first electrode 315-1a and the elongate member 304d has occurred because of an improper positioning of elongate member 304d (in this case, an improper overlapping positioning), which may be caused due to the elongate member 304d improperly deploying from the delivery configuration.

Other causes of a deviation from an expected positioning, such as that illustrated in FIG. 3E, of at least a portion of an electrode-based device system (e.g., 300) include interaction or interference with an anatomical structure as the structure 308 is moved between a delivery configuration and a deployed configuration. In some cases, positioning the structure 308 adjacent to, or in contact with tissue may cause an improper positioning of a portion of the electrode-based device system 300. For example, contact with a highly irregular tissue surface may lead to varying degrees of misposition. In some cases, when part of an electrode-based device system is improperly sized for a desired deployment in a bodily cavity, an improper positioning of the portion of the electrode-based device system may result when the part of the electrode-based device system is deployed in the bodily cavity. In some cases, interaction or interference with ancillary or other device systems used in conjunction with the electrode-based device system may cause an improper positioning of the portion of the electrode-based device system. Ancillary or other device systems may include a second electrode (e.g., a roving electrode). Roving electrodes employed by ancillary or other device systems may be used to determine a location, orientation or pose of at least part of an electrode-based-base device system in some example embodiments. By way of non-limiting example, ancillary or other device systems may respectively include other treatment or diagnostic device systems that may be used in conjunction with an electrode-based device system. In some cases, a deployment error or malfunction during one or more actuations of an electrode-based device system may cause an improper positioning of the portion of the electrode-based device system.

Any information that facilitates detection of or is indicative of the above-discussed deviation (e.g., FIG. 3E or any other deviation or particular condition (e.g., block 506)) from an expected positioning of at least a portion of an electrode-based device system according to the instructions associated with block 506A may be acquired according to the instructions associated with block 504A in FIG. 5B. Such information may include information that facilitates detection of or is indicative of the present positioning of at least a portion of the electrode-based device system and that is provided by the electrode-based device system itself (e.g., 200 or 300) or by another sensing device system (e.g., 325) that is working along with the electrode-based device system (e.g., internally (in the bodily cavity), such as by a roving electrode, or externally by fluoroscopy or ultrasound). Having an understanding of the present positioning of the electrode-based device system via information acquired according to block 504 in FIG. 5A or 504A in FIG. 5B allows a comparison of the present positioning with the expected positioning, which may be predetermined and pre-stored in the memory device system 130, and such a comparison may lead to a detection of the particular condition (e.g., block 506 in FIG. 5A), which may be a deviation from the expected positioning (e.g., block 506A in FIG. 5B). It should be noted, however, that the expected positioning need not be pre-determined or pre-stored in a memory device system, and the particular condition may be detected without a comparison to a pre-determined/pre-stored expected positioning. For example, detecting an error condition in information acquired according to the instructions associated with block 504 or 504A may result in the detection of the particular condition(s) as block 506 or 506A without need for comparison to an expected positioning. For instance, as discussed below, detection of a shunt condition or detection of a proximity below a threshold amount between an electrode and an object other than tissue may lead to a detection of an improper energy transmission configuration or a deviation in an expected positioning of at least one portion of the electrode-based device system.

In some embodiments, information acquired according to block 504 that facilitates detection of or is indicative of the particular condition(s) of block 506, or in the case of block 506A, the deviation from an expected positioning of at least a portion of the electrode-based device system, may include impedance information (e.g., associated with at least one electrode, such as the first electrode 315-1a), positional information, fluid flow information, convective heat information, temperature information, or a combination of these items. In the embodiments associated with FIG. 5B, the information acquired according to the instructions associated with block 504A includes positional information. This positional information, however, need not (but may, in some embodiments) take the form of positional mapping information that may, for example, employ various indicators such as locational coordinate systems and the like. Alternatively, the positional information may include impedance information, fluid flow information, convective heat information, temperature information, a combination of these items, or any other information that may facilitate identification of a present positioning of the electrode-based device system.

In this regard, the positional information can indicate various conditions. As with the example of FIG. 3E, the positional information may be indicative of a deviation in an expected positioning between a first electrode 315-1a and a physical portion of the electrode-based device system 300 when the structure 308 on which the first electrode 315-1a is located is positioned in the deployed configuration. Similarly, positional information that indicates the condition of FIG. 3E also may indicate that a portion of the structure 308 is not in an expected or desired position with respect to tissue adjacent the portion of the structure. For example, the condition of FIG. 3E may indicate that the portion of the first electrode 315-1a (an example of a portion of the structure 308) that is overlapped is not in its expected position where a desired portion of a tissue contact surface of the first electrode 315-1a should be in contact with or at least be available or fully exposed (e.g., without some obstruction preventing at least some of the ability) to contact tissue of a tissue wall that is adjacent the first electrode 315-1a. Positional information, such as an (e.g., an abnormally low) impedance reading from the first electrode 315-1a, that indicates that the electrode 315-1a is not fully available or fully exposed (e.g., without some obstruction preventing at least some of the ability) to contact or to be fully in contact with tissue indicates the condition of FIG. 3E which may, consequently, be detected according to the instructions associated with block 506 based on an analysis of such impedance reading.

In some embodiments, where a structure includes a plurality of elongate members (e.g., structure 308 including elongate members 304) with at least some of a plurality of electrodes located on each of the plurality of elongate members, the first electrode may be located on a first elongate member of the plurality of elongate members and the information acquired according to the acquisition instructions associated with block 504A may include positional information indicative of a deviation in an expected positioning between the first electrode and at least a second elongate member of the plurality of elongate members (e.g., an elongate member other than the first elongate member) when the structure is positioned in the bodily cavity in the deployed configuration. In some embodiments, the structure may include one or more elongate members with at least some of a plurality of electrodes located on each of the one or more elongate members (for example, a single elongate member on which a group of electrodes is located, the single elongate member having a curvilinear form in the deployed configuration). In various embodiments, the first electrode may be an electrode located on a first elongate member of the one or more elongate members and the information acquired according to the acquisition instructions associated with block 504 may include positional information indicative of a deviation in an expected positioning between the first electrode and an elongate member of the one or more elongate members when the structure is positioned in the bodily cavity in the deployed configuration. In various embodiments, the first electrode may be an electrode located on a first elongate member of the one or more elongate members and the information acquired according to the acquisition instructions associated with block 504 may include positional information indicative of a deviation in an expected positioning between the first electrode and a second electrode of the plurality of electrodes (i.e., other than the first electrode) when the structure is positioned in the bodily cavity in the deployed configuration. In some of these various embodiments, the second electrode may be located on the first elongate member. In some of these various embodiments, the one or more elongate members include a plurality of elongate members, and the second electrode is located on one of the plurality of elongate members other than the first elongate member. Different forms of positional deviations may be indicated in other embodiments. In some embodiments, the information acquired according to the acquisition instructions associated with block 504 includes positional information indicative of a deviation in an expected positioning between a portion of the electrode-based device system (e.g., electrode, structural member) and a tissue structure within a bodily cavity in which the portion of the electrode-based device system is positioned.

Figure 5C:
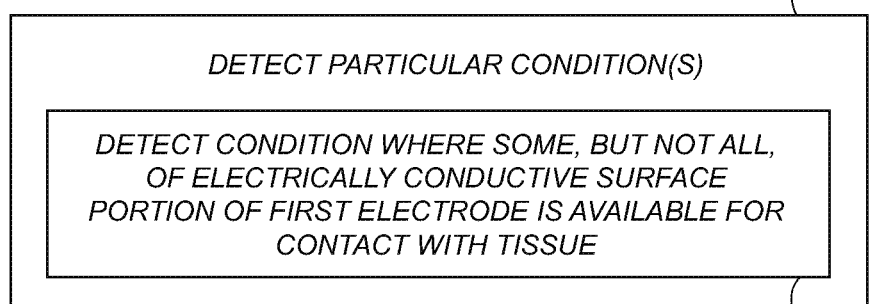
FIG. 5C is an exploded view of a block of the block diagram of FIG. 5A according to some example embodiments, the exploded block associated with a detection of a condition indicating that some, but not all, of an electrically conductive surface portion of a first electrode is available to contact tissue of a tissue wall, according to some embodiments.

FIG. 5C includes exploded views of the block 506 as employed in various embodiments. In this regard, block 506 may include a block 506B whose associated instructions are configured to cause a detection of a particular condition based on an analysis of the information acquired according to the acquisition instructions associated with block 504 (or block 504A, e.g.), the particular condition indicating that some, but not all, of the respective electrically conductive surface portion of at least the first electrode (e.g., first electrode 315-1a) is available or fully exposed (e.g., without some obstruction preventing at least some of the ability) to contact tissue of a tissue wall of a bodily cavity (e.g., left atrium 204 (i.e., in absence of the particular condition, a contiguous surface portion of the tissue wall is contactable by all of the respective electrically conductive surface portion of at least the first electrode). In some embodiments, the particular condition indicates that at least a portion of the respective electrically conductive surface portion of at least the first electrode (e.g., first electrode 315-1a) is obstructed.

The particular condition may be detected in similar manners described above with respect to FIGS. 5B and 3E, where the overlapped first electrode 315-1a in FIG. 3E may be considered to have some, but not all, of its electrically conductive surface portion (defined, in some embodiments, by an electrode edge 415-1 in FIG. 4) available for contact with tissue due to the overlapping (e.g., of the elongate member 304d acting as a partial obstruction in the example of FIG. 3E). In some of these various embodiments, this particular condition is detected when a structure (e.g., 308) on which the first electrode (e.g., first electrode 315-1a) is located is positioned in the bodily cavity in the deployed configuration. In some of these various embodiments, the entirety of the electrically conductive surface portion of each of at least the first electrode is configured, in absence of the particular condition, to contact a contiguous surface portion of the tissue wall when the structure on which the first electrode is located is positioned in the bodily cavity in the deployed configuration. For example, the entirety of the electrically conductive surface portion of the first electrode (e.g., 315-1a) is configured to be available or fully exposed (e.g., without some obstruction preventing at least some of the ability) for contact, as shown in FIG. 3D, when the condition of FIG. 3E is absent. In some embodiments, at least part of the electrically conductive surface portion (e.g., at least part of the energy transmission surface) of the first electrode (e.g., 315-1a) is outward facing, e.g., positioned to face outward or towards an adjacent surface positioned to face towards a surface portion of the tissue wall, when the structure (e.g., 308) is positioned in the bodily cavity in the deployed configuration. In some of these embodiments, the condition is associated with a positioning of a physical portion (e.g., an obstruction, such as elongate member 304d, which is a portion of the structure 308; the first electrode being located on the structure 308) of the electrode-based device system between the electrically conductive surface portion of the first electrode and the surface portion of the tissue wall when the structure is positioned in the bodily cavity in the deployed configuration. In other words, in some embodiments, the condition detected according to the instructions associated with block 506B may be associated with an obstruction, such as a physical portion (e.g., elongate member 304d) of the electrode-based device system being between the first electrode (e.g., 315-1a) and the tissue wall. Possible obstructions are not limited to elongate member 304d and may include other electrodes or even other elements that do not form part of, or are located on structure 308 in other embodiments.

In some particular embodiments associated with FIG. 3E, structure 308 includes a plurality of elongate members 304 with at least some of the plurality of electrodes 315 located on each of the plurality of elongate members 304. In the some of these particular embodiments, at least some of the electrodes 315 are located on one, but not both, of the respective front and back surfaces 318a, 318b (only front surfaces 318a called out in FIG. 3E) of each of the plurality of elongate members 304. In FIG. 3E, at least the first electrode 315-1a is located on the respective front surface 318a of a first elongate member (i.e., elongate member 304c) and the information acquired according to the acquisition instructions of block 504 may include positional information indicative of a positioning when at least part of the electrically conductive surface portion of the first electrode 315-1a faces the respective back surface 318b (not called out) of the second elongate member (e.g., elongate member 304d) when structure 308 is positioned in the bodily cavity in the deployed configuration. In various ones of embodiments described above, the detected conditions may arise because of a deviation in an expected positioning between the first electrode and some physical portion of the electrode-based device system.

It should be noted that a deviation detected in accordance with the detection instructions associated with 506A may also be related to the particular condition detected in accordance with the detection instructions associated with 506B or any other instructions associated with block 506 as well as various other instruction blocks that may be associated with method 500. For example, a deviation detected in accordance with block 506A may also be indicative of the particular condition detected in accordance with block 506B and vice-versa.

In some embodiments, the detection of a particular condition in accordance with a particular constituent detection instruction set associated with 506 may cause storage instructions associated with block 508 to additionally or alternatively store information that is related to another particular condition that is detectable by another particular detection instruction set associated with block 506. It is noted that in some embodiments, activity initiated by (a) the restriction instructions associated with 510, (b) the failure state instructions associated with 512 or both (a) and (b) may be dependent on (c) the detection information indicating the result of the detection of a particular condition according to the detection instructions of any of the constituent detection instruction sets associated with block 506 or various other blocks of method 500, (d) determination information indicating a particular determination indicating a result of determination instructions associated with various blocks of method 500, or (e) various information stored in the memory device system by the storage instructions associated with 508.

Figure 5D:
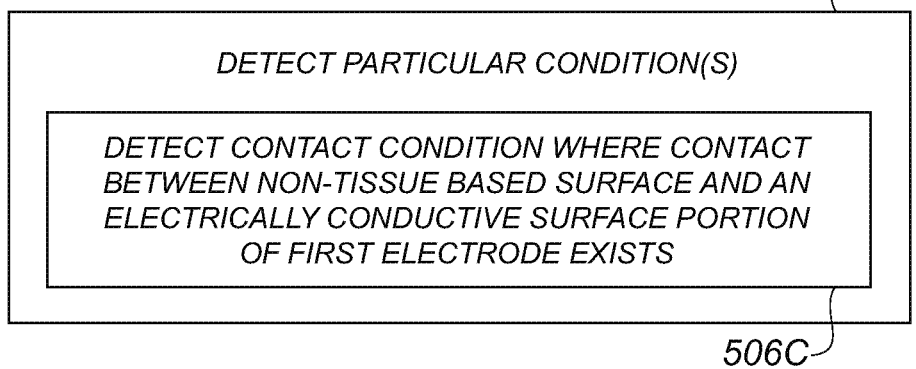
FIG. 5D is an exploded view of a block of the block diagram of FIG. 5A according to some example embodiments, the exploded block associated with a detection of a condition indicating contact between a non-tissue based surface and an electrically conductive surface portion of a first electrode, according to some embodiments.

FIG. 5D includes an exploded view of block 506 as employed in various embodiments. In this regard, block 506 may include a block 506C whose associated instructions are configured to cause a detection of a particular condition based on an analysis of the information acquired according to the acquisition instructions associated with block 504, the particular condition indicating contact (e.g., a contact condition) between a non-tissue based surface positioned in the bodily cavity and the electrically conductive surface portion of the first electrode (e.g., first electrode 315-1a) when a structure on which the first electrode is located (e.g., structure 308) is positioned in the bodily cavity in the deployed configuration. The non-tissue based surface may take various forms in various ones of these embodiments. For example, the non-tissue based surface may be a surface of a second electrode other than the first electrode. In some embodiments, the second electrode is a roving electrode that is not located on the structure. In some embodiments, the second electrode is an electrode that is also located on the structure. In some embodiments, the non-tissue based surface does not form part of any electrode (e.g., a portion of an elongate member 304 that does not include an electrode). In some embodiments, the non-tissue based surface forms a surface of a physical portion of the electrode-based device system that includes the first electrode (e.g., elongate member 304). In some embodiments, the non-tissue based surface forms a portion of the structure. For example in FIG. 3E, the non-tissue based surface may form part of the back surface 318b (not called out) of the second elongate member 304d.

Contact between a first electrode (e.g., first electrode 315-1a) and a non-tissue based surface can be detected in various ways, such as those described above with respect to FIG. 5B and FIG. 3E. Other techniques may be used (e.g., various imaging techniques) however, not only for the embodiments of FIG. 5D, but also for the embodiments of FIGS. 5B, 5C, 5E, 5F, 5G, and 5H. For example, in some embodiments, when the non-tissue based surface is an electrically conductive non-tissue based surface, contact between the first electrode and the electrically conductive non-tissue based surface may be detected by detecting a shunt condition (also referred to as shunted condition).

Figure 5E:
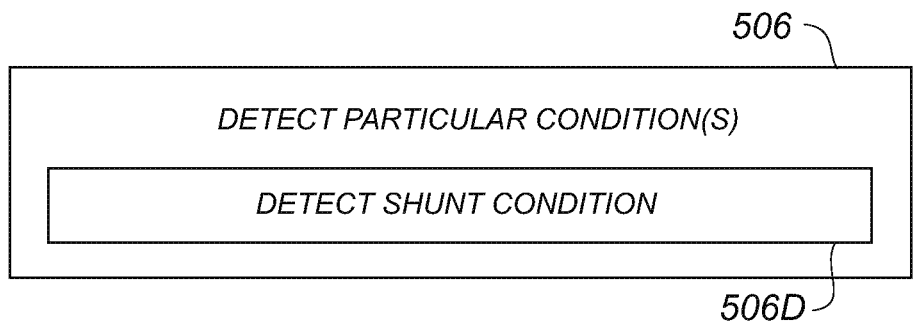
FIG. 5E is an exploded view of a block of the block diagram of FIG. 5A according to some example embodiments, the exploded block associated with a detection of a shunt condition, according to some embodiments.

FIG. 5E includes an exploded view of the block 506 as employed in various embodiments. In this regard, block 506 may include a block 506D whose associated instructions are configured to cause a detection of a particular condition based on an analysis of the information acquired according to the acquisition instructions associated with block 504, the particular condition being a shunt condition, the shunt condition associated with a diversion of a portion of energy (e.g., electric current) transmittable by a first electrode (e.g., first electrode 315-1a located on structure 308) positionable in a bodily cavity (e.g., left atrium 204) defined at least in part by a tissue wall. In various embodiments, the shunt condition is created in an electric circuit that includes at least the first electrode. In some embodiments, the shunt condition includes a diversion of a portion, but not all, of energy (e.g., electric current) transmittable by the first electrode away from a portion of adjacent tissue of the tissue wall, the adjacent tissue adjacent the first electrode. In some embodiments, the energy transmittable by the first electrode is sufficient for tissue ablation. However, in some embodiments, the energy transmittable by the first electrode is insufficient for tissue ablation.

Figure 5F:
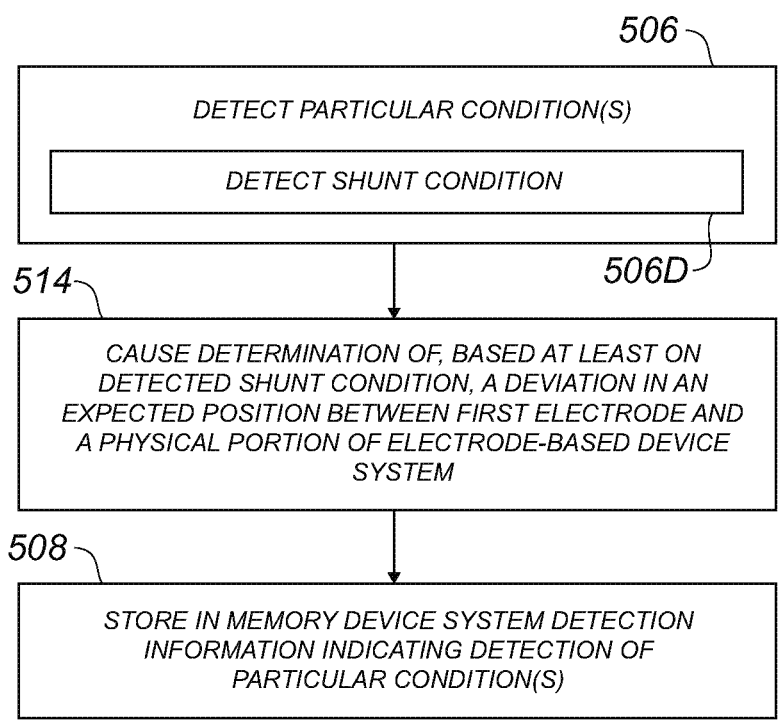
FIG. 5F is an exploded view of a portion of the block diagram of FIG. 5A according to some example embodiments, the exploded view associated with a determination of a deviation in an expected position between a first electrode and a physical portion of an electrode-based device system based at least on a detected shunt condition, according to some embodiments.
Figure 5G:
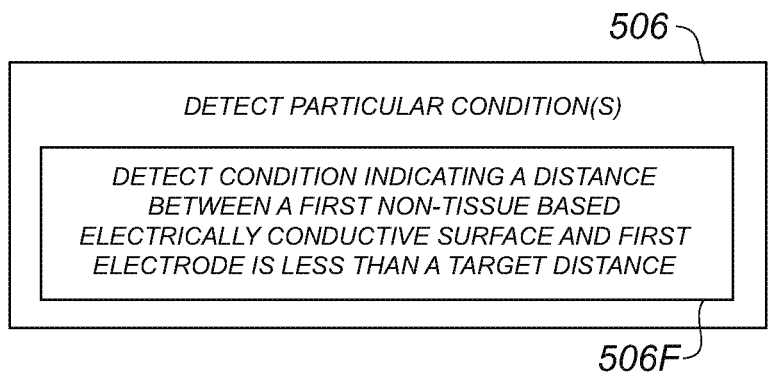
FIG. 5G is an exploded view of a block of the block diagram of FIG. 5A according to some example embodiments, the exploded block associated with a detection of a condition indicating that a distance between a first non-tissue based electrically conductive surface and a first electrode is less than a target distance, according to some embodiments.

In some embodiments, as shown with block 514 in FIG. 5F the detection of the shunt condition may lead to a determination of a deviation in an expected positioning, as discussed above with respect to block 506A in FIG. 5B. In the example of block 514, the deviation in expected position may be between a first electrode and a physical portion of an electrode-based device system, at least when a structure (e.g., 308) of the electrode-based device system on which the first electrode is located, is in a deployed configuration. In this regard, a detected shunt condition may indicate and lead to a determination of an improper energy delivery configuration such as that shown in FIG. 3E.

In some embodiments, the shunt condition includes a diversion of the portion of the energy (e.g., electric current) transmittable by the first electrode from traveling along (a) a first electrical path extending from the first electrode to the portion of the adjacent tissue of the tissue wall, to (b) a second electrical path extending from the first electrode away from the portion of the adjacent tissue of the tissue wall. For example, FIG. 6A is a schematic cross-sectional view of a first electrode 615-1a positioned adjacent tissue 621a of a tissue wall 622a that defines at least part of a bodily cavity 624a, the adjacent tissue 621a located adjacent first electrode 615-1a. First electrode 615-1a is located on a portion of a structural member 604-1a (e.g., an elongate member 304). In FIG. 6A, energy is transmittable from the first electrode 615-1a to a second electrode 626a along a first electrical path (schematically depicted at least in part by electric field lines 625a) extending from the first electrode 615-1a to the second electrode 626a. In various embodiments, the second electrode is an indifferent electrode configured to be positioned outside of the bodily cavity 624a or even outside a body that includes the bodily cavity 624a. It is understood that that each of the various tissue walls depicted in FIG. 6 (e.g., tissue wall 622a, 622b, or 622c) need not include a single tissue layer, but may also include multiple combinations of non-fluidic tissue and fluidic tissue or multiple layers of different tissue. The first electrical path may be associated with monopolar ablation in various example embodiments. It is noted that in this disclosure, the use of field lines such as field lines 625a to schematically illustrate an electrical path is employed merely for the convenience of discussion and it is understood that electrical paths described in various embodiments can take various different forms or can be illustrated in other manners. As used herein, the phrase "electrical path" is typically associated with a flow of electrical current, the electrical current preferentially following a particular route along which the path electrical impedance is the lowest. Some electrical paths may be readily identified (e.g., electrical current flowing through a conductor having a relatively high electrical conductivity such as a metallic conductor). Other electrical paths may be more difficult to identify (e.g., electrical current flowing through tissue made up of different constituent tissue parts). In this disclosure, the diversion of energy or electrical current flowing along a first electrical path to a different second electrical path is typically characterized by a lower path impedance being present along the second electrical path.

FIG. 6B is a top view of FIG. 6A from within the bodily cavity 624a from above the structural member 604-1a and looking towards the structural member 604-1a. In this regard, the first electrode 615-1a is shown in broken lines, and structural member 604-1a is shown over the tissue wall 622a. Some of the electric field lines 625a are represented by the symbols "●" in FIG. 6B. The electric field lines have a relatively high electric field density in this embodiment. A relatively high electric field density may be required for effective tissue ablation in various embodiments.

FIG. 6C includes a shunt condition associated with various example embodiments where a diversion occurs of a portion of energy (e.g., electric current) transmittable by the first electrode 615-1a from the first electrical path (e.g., FIG. 6A, 6B) to a second electrical path schematically depicted at least in part by electric field lines 625b different than the first electrical path. In some of these example embodiments, the shunt condition is defined to occur at least when contact between the first electrode 615-1a (or an electrically conductive surface portion thereof) and a first non-tissue based electrically conductive surface 630-1 (in the example of FIG. 6C, a rear surface of an overlapping structural member 604-1b on which another electrode 615-1b is located, the rear surface facing inwardly into bodily cavity 624a) located in the bodily cavity 624a is established. In some of these example embodiments, the shunt condition includes a diversion of a portion of the energy (e.g., electric current) transmittable by the first electrode 615-1a to the second electrode 626a, the diversion to the first non-tissue based electrically conductive surface 630-1 or structural member 604-1b thereof.

It should be noted that a non-tissue based electrically conductive surface (such as surface 630-1 or any other non-tissue based electrically conductive surface discussed in this disclosure) can form part of any number of different devices according to various embodiments. For example, a non-tissue based electrically conductive surface may be a surface of an electrode (e.g., a roving electrode) that is not located on the structure (e.g., 308) on which the first electrode (e.g., first electrode 615-1a) is located. In some embodiments, a non-tissue based electrically conductive surface may be a surface of another electrode besides the first electrode located on a structure on which the first electrode is located (e.g., electrode 615-1b). However, in some embodiments, a non-tissue based electrically conductive surface does not form part of any electrode. For example, a first non-tissue based electrically conductive surface may form an electrically conductive surface or portion (e.g., a metallic surface or portion) of a device or structure (e.g., 308) of an electrode-based device system (e.g., 200 or 300) that includes the first electrode. In some example embodiments, a first non-tissue based electrically conductive surface may form an electrically conductive surface of a structure (e.g., 308), the structure having the first electrode located thereon or therein (e.g., the electrically conductive surface may be a surface of structural member 604-1b on which another electrode 615-1b is located, both structural members 604-1a and 604-1b forming part (e.g., respective elongate members 304) of a selectively configurable structure such as structure 308, the structure 308 also supporting the first electrode, e.g., 615-1a).

In various embodiments associated with various ones of FIGS. 6A, 6B, 6C and 6D, the shunt condition includes a diversion of the portion of the energy (e.g., electric current) transmittable by the first electrode 615-1a from traveling along (a) a first electrical path extending from the first electrode 615-1a to a portion of the adjacent tissue 621a, to (b) a second electrical path extending from the first electrode 615-1a away from the portion of the adjacent tissue 621a, the second electrical path extending through an element that includes the first non-tissue based electrically conductive surface 630-1.

One or more of electrodes 615-1a, 615-1b and structural members 604-1a, 604-1b may take different forms, shapes or sizes in other embodiments. It is noted that tissue of a tissue wall against which the first electrode is positioned may be sufficiently compliant to allow a respective portion of a shunting element to be depressed into the tissue during the shunting. For example, in embodiments associated with FIG. 6C, (a) respective portion of electrode 615-1b, (b) a respective portion of structural member 604-1b, or both (a) and (b) may be depressed into tissue of tissue wall 622 by a different amount than other elements (e.g., electrode 615-1a). This may occur, for example, due to positioning or mispositioning of the structure 308 and the particular contours of the bodily cavity in which it is deployed or expanded. Various electrodes and structural members depicted in FIG. 6 have their dimensions exaggerated for clarity.

It is noted that in some embodiments, the shunt condition includes a smaller portion of the energy transmittable by the first electrode 615-1a being receivable by the portion of the adjacent tissue 621a as compared to an unshunted condition. For example, in various embodiments, an amount of energy transmittable by the first electrode 615-1a and receivable by the portion of the adjacent tissue 621a will be less in the shunted condition shown in FIG. 6C than in the unshunted condition shown in FIG. 6A. This is schematically represented in FIG. 6C by a relatively fewer number of electric field lines 625a-1 located in the vicinity of adjacent tissue 621a. It is noted that some unshunted conditions may result in a situation where not all of the energy that is transmittable by the first electrode is directly deliverable to the adjacent tissue 621a and that a portion of this transmittable energy may be deliverable or delivered to another particular entity (e.g. an electrically conductive surface provided by another electrode, structural member, et cetera positioned in the bodily cavity). A magnitude or amount of this portion of the transmittable energy will typically vary in accordance with the distance between the first electrode 615-1a and the particular entity. However, in various embodiments, a shunt condition may typically result in an increase in the amount of the transmittable energy (e.g., electric current) that is diverted as compared to an unshunted condition. In some embodiments, an increase in the amount of the transmittable energy traveling through non-fluid tissue other than the portion of the adjacent tissue 621a may occur in the shunted condition as compared to an unshunted condition.

In some example embodiments, the second electrical path also extends from the first electrode 615-1a to the second electrode 626a but along a different path than the first electrical path. An example of this is shown in FIG. 6C in which the second electrical path (represented by electric field lines 625b) extends from the first electrode 615-1a to the second electrode 626a via tissue (e.g., tissue including non-fluid tissue) different than at least a portion of the adjacent tissue 621a. This situation can occur for various reasons. For example, when the first non-tissue based electrically conductive surface 630-1 contacts the first electrode 615-1a, the energy transmission surface of the first electrode 615-1a is effectively increased and allows energy to be delivered to the second electrode 626a via a different electrical path or paths. In FIG. 6C, the first non-tissue based electrically conductive surface 630-1 forms an electrically conductive surface of a structure (e.g., structural member 604-1b). The first electrode 615-1a may also be located on the structure. In cases where a first non-tissue based electrically conductive surface forms a relatively large portion of the structure (e.g., a back surface 318b of an elongate member 304 in some embodiments) energy transmission along electrical paths different than the first electrical path is likely.

FIG. 6D is a top view like FIG. 6B, but of FIG. 6C, and illustrates the overlapping of the structural members 604-1a and 604-1b over tissue wall 622a, according to some embodiments. The overlapping edge of structural member 604-1b is illustrated in broken lines, while each of the electrodes 615-1a and 615-1b also are illustrated in broken lines. In FIG. 6D, the electrode 615-1a is shunted by the first non-tissue based electrically conductive surface 630-1. Some of the electric field lines 625a-1 and 625b are represented by the symbols "●". The electric field lines 625a-1 have a relatively low field density in various embodiments (as compared to the electric field density shown in FIG. 6B). In some cases, low field densities may not be conducive for effective tissue ablation. Accordingly, the detection of a shunt condition that may indicate a condition in which these lower electric field densities may exist is advantageous. In various embodiments, the electric field lines 625b have a relatively high field density in regions of contact between the first electrode 615-1a and the first non-tissue based electrically conductive surface 630-1. The electric field lines 625b illustrated away from the overlap region between structural members 604-1a and 604-1b in FIG. 6D illustrate the electric field lines that enter the tissue wall 622a on the right hand side of FIG. 6C.

Figure 6E:
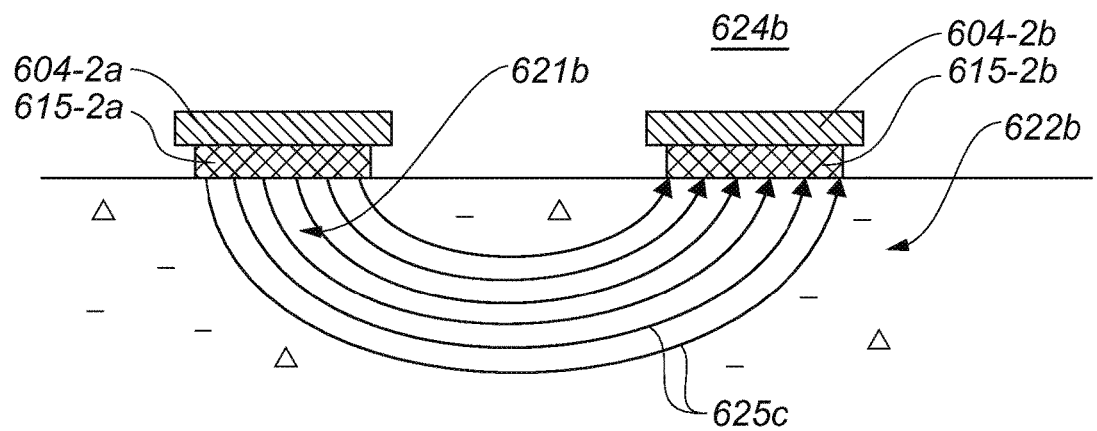
FIG. 6E is a schematic cross sectional view, according to various example embodiments, of a first electrode positioned adjacent tissue of a tissue wall that defines, at least in part, a bodily cavity, energy transmittable from the first electrode flowing along a first electrical path to a second electrode positioned in the bodily cavity, according to some embodiments.

Shunted conditions may also be encountered in other energy transmission configurations. For example, FIGS. 6E and 6F respectively show unshunted and shunted conditions associated with a first electrode 615-2a located on a structural member 604-2a (e.g., an elongate member 304). FIG. 6E schematically depicts first electrode 615-2a positioned adjacent tissue 621b of a tissue wall 622b that defines at least part of a bodily cavity 624b. In this embodiment, energy is transmittable from the first electrode 615-2a to a second electrode 615-2b along a first electrical path (schematically depicted at least in part by electric field lines 625c) extending from the first electrode 615-2a to the second electrode 615-2b. In various embodiments, the second electrode 615-2b is another electrode positioned within the bodily cavity 624-b. In various embodiments, the second electrode 615-2b is located on a structural member 604-2b (e.g., an elongate member 304). In various embodiments, structural members 604-2a and 604-2b may form part of a selectively configurable structure such as structure 308. The first electrical path may be associated with bipolar ablation in various example embodiments associated with FIGS. 6E and 6F. Although an indifferent electrode is not shown in FIGS. 6E and 6F for clarity, it is understood that it may be included especially in blended monopolar-bipolar applications. It is understood that in various embodiments, current may flow back and forth between electrodes 615-2a and 615-2b in a reciprocating or alternating manner.

Figure 6F:
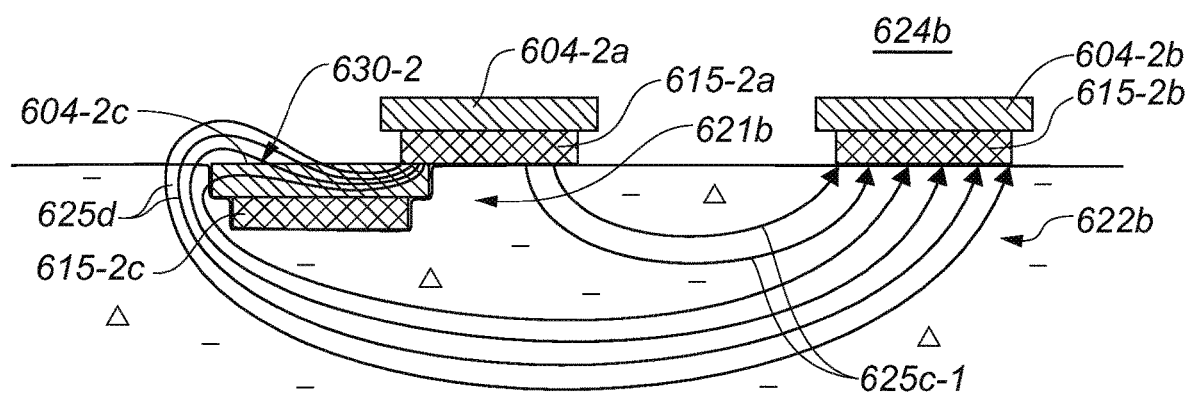
FIG. 6F illustrates a shunt condition associated with a diversion of a portion of energy transmittable by the first electrode of FIG. 6E from the first electrical path to a second electrical path different than the first electrical path, according to some embodiments.

FIG. 6F, as compared to FIG. 6E, shows a shunt condition (i.e., also referred to as a shunted condition) associated with various example embodiments where a portion of energy (e.g., electric current) transmittable by the first electrode 615-2a is diverted from the first electrical path (e.g., FIG. 6E) to a second electrical path schematically depicted at least in part by electric field lines 625d different than the first electrical path. In some of these example embodiments, the shunt condition is defined to occur at least due to contact between the first electrode 615-2a and a first non-tissue based electrically conductive surface 630-2 located in the bodily cavity 624b. In some of these example embodiments, the shunt condition includes a diversion of a portion of the energy (e.g., electric current) transmittable by the first electrode 615-2a to the second electrode 615-2b, the diversion to the first non-tissue based electrically conductive surface 630-2 or structural member 604-2b thereof. As discussed above, a non-tissue based electrically conductive surface, including the first non-tissue based electrically conductive surface 630-2, can form part of any number of different devices. In some embodiments, such as those according to FIG. 6F, the first non-tissue based electrically conductive surface 630-2 is provided by a structural member 604-2c on which a third electrode 615-2c is located. One or more of electrodes 615-2a, 615-2b, 615-2c and structural members 604-2a, 604-2b, 604-2c may take different forms, shapes or sizes in other embodiments. In various embodiments associated with FIGS. 6E and 6F, the shunt condition includes a diversion of a portion of the energy (e.g., electric current) transmittable by the first electrode 615-2a from traveling along (a) a first electrical path extending from the first electrode 615-2a to a portion of the adjacent tissue 621b, to (b) a second electrical path extending from the first electrode 615-2a away from the portion of the adjacent tissue 621b, the second electrical path extending through an element that includes the first non-tissue based electrically conductive surface 630-2. In various embodiments associated with FIGS. 6E and 6F, the second electrical path (e.g., represented by electric field lines 625d) extends to the second electrode 615-2b. In various embodiments associated with FIGS. 6E and 6F, the second electrical path (e.g., represented by electric field lines 625d) extends to the second electrode 615-2b via the structural member 604-2c (e.g., a physical portion of the electrode-based device system and via tissue different than the portion of adjacent tissue 621-b (e.g., part of the tissue wall 622b other than the portion of adjacent tissue 621-b). For example, when the first non-tissue based electrically conductive surface 630-2 forms a relatively large portion of the structure (e.g., a back surface 318b of an elongate member 304 in some embodiments), energy transmission to the second electrode 615-2b along electrical paths different than the first electrical path can occur.

As illustrated in FIG. 6F and discussed above with respect to FIG. 6C, reference 625a-1, the shunting need not divert all energy (e.g., electric current) transmittable by the first electrode 615-2a. This circumstance is illustrated by field lines 625c-1 which follow the same or approximately the same portion of the first electrical path illustrated in FIG. 6E.

In some example embodiments, the shunt condition includes at least a portion of the first electrode being overlapped by a physical portion of an electrode-based device system that includes the first electrode 615-2a. For example, as shown in FIG. 6F, a shunt condition may be associated with at least a portion of the first electrode 615-2a (i.e., located on structural member 604-2a) being overlapped by a portion of structural member 604-2c (i.e., as viewed from tissue wall 622b towards first electrode 615-2a). In some embodiments, the structure on which the first electrode 615-2a is located includes one or more elongate members with at least some of a plurality of electrodes that include the first electrode 615-2a being located on each of the one or more elongate members. In some embodiments, the shunt condition includes at least a portion of the first electrode 615-2a being overlapped by an elongate member of the one or more elongate members when the structure is deployed in the bodily cavity. It is noted that, in some embodiments, contact may or may not be present between the overlapped portion of the first electrode 615-2a and the overlapping member to cause a shunt condition.

In this regard, it is noted that a shunt condition detected in accordance with various embodiments need not necessarily involve contact between the first electrode (e.g., electrodes 315-1a, 615-1a, 615-2a or another electrode 415) and some other non-tissue based electrically conductive surface (e.g., first non-tissue based electrically conductive surface 630-1 or 630-2). In some embodiments, a shunt condition may occur that is associated with a diversion of energy (e.g., electric current) transmittable by the first electrode due to the first electrode's proximity, but not contact, to some other non-tissue based electrically conductive surface.

According to some embodiments, a shunt may be an alternate current path as compared to an original current path that allows current to pass through a new or different point that was not passed through by current in the original current path. In some embodiments involving various tissue ablation applications where lesions are formed in tissue (e.g., tissue forming a tissue surface), a circuit is formed from an energy source device system (e.g., energy source device system 340 (e.g., typically in the form of a radio-frequency (RF) generator device system in some embodiments)) to an electrode (e.g., an electrode 315, 415) of an electrode based-device system (e.g., electrode-based device system 200 or 300), through the tissue of the body, back through another electrode (e.g. an indifferent electrode such as indifferent electrode 326 or some other electrode (e.g., some other electrode 315, 415)) of the electrode-based device system, and finally back to the energy source device system. In cardiac ablation procedures, the lesions can provide electrophysiological blocks configured to block electrophysiological activity in cardiac tissue. In this regard, a lesion typically is formed in close proximity to the electrode where the electrical current density through the tissue is sufficiently high to ablate the tissue. At some distance from the electrode, the current flows through a large volume of tissue, which causes the electrical current density to be low and typically results in an insignificant amount of heating. If a first non-tissue based electrically conductive surface (e.g., first non-tissue based electrically conductive surface 630-1 or 630-2) is positioned sufficiently close to the electrode, then the non-tissue based electrically conductive surface will provide a low impedance path along which current can flow. The low impedance path will introduce a shunt path which will divert some of the current to the first non-tissue based electrically conductive surface. The diverted current will typically alter the distribution of the current density in the tissue.

In the case where the first non-tissue based electrically conductive surface is in contact with the electrode, the first non-tissue based electrically conductive surface typically will form a shunt diverting most of the current away from tissue proximate the electrode (e.g., at least a portion of adjacent tissue 621a or 621b). The electrical current may be diverted to the tissue surrounding the non-tissue based electrically conductive surface (e.g., as described above in this disclosure). The effect may be such that the energy source device system (e.g., an RF generator device system) may see a noticeably lower impedance than when the shunt condition did not exist. The diverted current will result in an overall lower current density in the tissue adjacent the electrode (e.g., adjacent tissue which will cause less heating and may typically not form a suitable lesion).

In the case where the first non-tissue based electrically conductive surface is in sufficiently close proximity to the electrode, but is not contacting the electrode, the first non-tissue based electrically conductive surface can provide a lower impedance path which will tend to divert some portion of the electrical current to the first non-tissue based electrically conductive surface. The volume of any tissue which is in proximity to both the electrode and the non-tissue based electrically conductive surface may likely see a higher electric current density due to a portion of the electrical current being diverted from the electrode to the first non-tissue based electrically conductive surface. In cases where the tissue proximate to both the electrode and the first non-tissue based electrically conductive surface is blood tissue, the higher electrical current density could result in excessive heating in the blood tissue which may lead to undesired thermal coagulum formation. Close proximity between the first non-tissue based electrically conductive surface and the electrode may have an effect in which the energy source device system (e.g., an RF generator device system) may likely see a lower impedance than when the shunt condition does not exist.

Figure 6G:
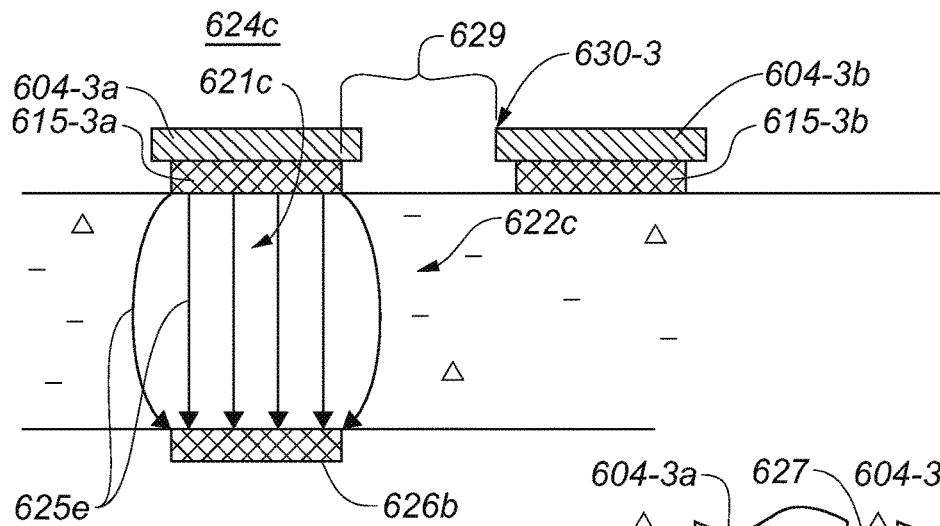
FIG. 6G is a schematic cross sectional view, according to various example embodiments, of a first electrode positioned adjacent tissue of a tissue wall that defines a bodily cavity, energy transmittable from the first electrode flowing along a first electrical path, according to some embodiments.
Figure 6I:
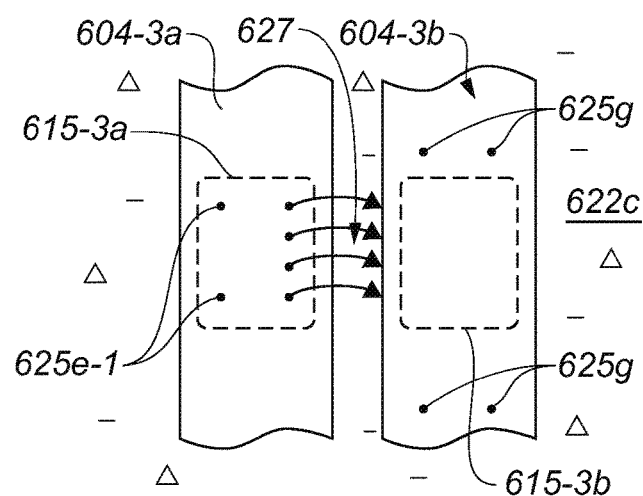
FIG. 6I is a top view of at least the first electrode and tissue wall of FIG. 6H, according to some embodiments.
Figure 6H:
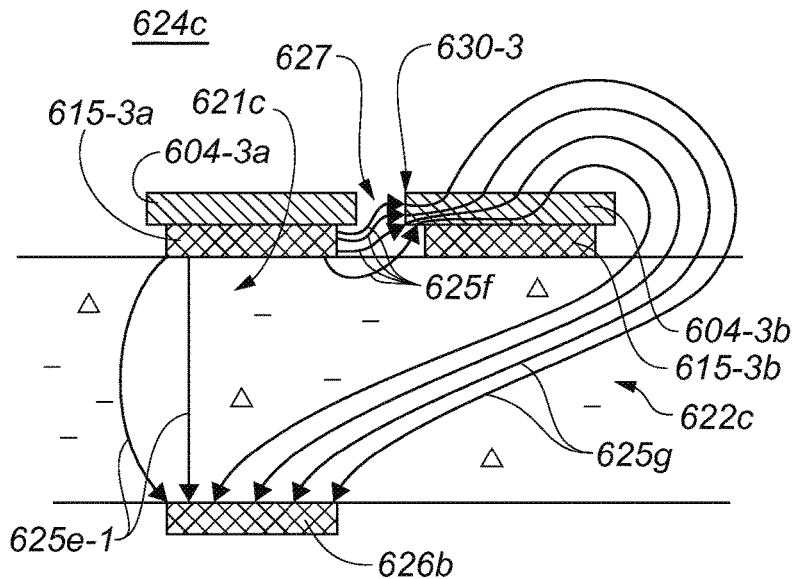
FIG. 6H illustrates a shunt condition associated with a diversion of a portion of energy transmittable by the first electrode of FIG. 6G from the first electrical path to a second electrical path different than the first electrical path, according to some embodiments.

FIGS. 6G and 6H respectively represent unshunted and shunted conditions associated with a first electrode 615-3a. FIG. 6G schematically shows first electrode 615-3a positioned adjacent tissue 621c of a tissue wall 622c that defines a bodily cavity 624c. In this example, energy is transmittable from the first electrode 615-3a to a second electrode 626b (e.g., an indifferent electrode in various embodiments) along a first electrical path (schematically depicted at least in part by electric field lines 625e) extending from the first electrode 615-3a to the second electrode 626b. The first electrical path may be associated with monopolar ablation in various example embodiments. FIG. 6H shows a shunt condition (also referred to as a shunted condition) associated with various example embodiments in which a diversion of a portion of energy (e.g., electric current) transmittable by the first electrode 615-3a from the first electrical path (e.g., FIG. 6G) to a second electrical path (schematically depicted at least in part by electric field lines 625f) different than the first electrical path occurs. In some of these embodiments, some of the energy continues to be transmittable from the first electrode 615-3a along the first electrical path (i.e., represented by electric field lines 625e-1) in the shunted condition. In some of these example embodiments, the shunt condition is defined to occur at least due to sufficient proximity (e.g., as described above in this disclosure) between the first electrode 615-3a and a first non-tissue based electrically conductive surface 630-3 located in the bodily cavity 624c. In some of these example embodiments, the shunt condition includes a diversion of a portion of the energy (e.g., electric current) transmittable by the first electrode 615-3a to the second electrode 626b, the diversion to the first non-tissue based electrically conductive surface 630-3 or structural member 604-3b thereof. The first non-tissue based electrically conductive surface 630-3 can form part of any number of different devices as described above in this disclosure, and, in this regard, may, e.g., be a surface of structural member 604-3b, second electrode 615-3b, or both structural member 604-3b and second electrode 615-3b. In various embodiments, the first non-tissue based electrically conductive surface 630-3 is provided by a structural member 604-3b on which a second electrode 615-3b is located. Energy in turn flows via an electrical path (i.e., represented by field lines 625g) from structural member 604-3b to second electrode 626b. In embodiments where bodily cavity 624c is an intra-cardiac cavity, blood tissue in region 627 may be subjected to formation of thermal coagulum due to the higher energy current density associated with the shunted condition shown in FIG. 6H. In various embodiments associated with FIG. 6H, the shunt condition includes a diversion of the portion of the energy (e.g., electric current) transmittable by the first electrode 615-3a from traveling along (a) a first electrical path extending from the first electrode 615-3a to a portion of the adjacent tissue 621c, to (b) a second electrical path extending from the first electrode 615-3a away from the portion of the adjacent tissue 621c, the second electrical path extending through an element that includes the first non-tissue based electrically conductive surface 630-3. In various embodiments associated with FIG. 6H, the second electrical path (e.g., represented by electric field lines 625f and 625g) extends to second electrode 626b. In various embodiments associated with FIG. 6H, the second electrical path (e.g., represented by electric field lines 625f and 625g) extends to second electrode 626b via tissue (e.g., non-fluidic tissue) different than at least a portion of the adjacent tissue 621c. For example, when the first non-tissue based electrically conductive surface 630-3 forms a relatively large portion of the structure (e.g., a back surface 318b of an elongate member 304 in some embodiments) energy transmission to the second electrode 626b along electrical paths different than the first electrical path and involving passage through different tissue can occur.

FIG. 6I illustrates a top view like FIG. 6B and FIG. 6D, but of FIG. 6H, and illustrates the electrodes 615-3a and 615-3b as broken lines. Structural member 604-3a is illustrated over tissue wall 622c, and the first electrode 615-3a is shunted by structural member 604-3b due to sufficient proximity of the structural member 604-3b with the electrode 615-3a, as discussed above with respect to FIG. 6G. Some of the electric field lines 625e-1 and field lines 625g are represented by the symbols "●". In various embodiments, the electric field lines 625f emerging from first electrode 615-3a have a relatively higher electric field density than the electric field lines 625e-1 emerging from first electrode 615-3a. The higher electric field density may lead to thermal coagulation of blood in some cases. One or more of electrodes 615-3a, 615-3b and structural members 604-3a, 604-3b may take different forms, shapes or sizes in other embodiments. Similar results can occur in bipolar applications. Distances between first electrode 615-3a and first non-tissue based electrically conductive surface 630-3 have been exaggerated for clarity.

In view of the above discussion pertaining to FIGS. 6G, 6H, and 6I, FIG. 5G illustrates an exploded view of block 506 of FIG. 5A according to, among other embodiments, some embodiments pertaining to detection of a condition in which an electrode is too close to (or even improperly contacts in some embodiments) a non-tissue based electrically conductive surface. In this regard, block 506 may include a block 506F whose associated instructions are configured to cause a detection of a particular condition based on an analysis of the information acquired according to the acquisition instructions associated with block 504, the particular condition indicating that a distance between a first non-tissue based electrically conductive surface positioned in a bodily cavity (e.g., first non-tissue based electrically conductive surface 630-1, 630-2 or 630-3) and a first electrode positioned in the bodily cavity (e.g., first electrode 615-1a, 615-2a, or 615-3a) has been detected to be less than a non-zero target distance between the first non-tissue based electrically conductive surface and the first electrode. In various embodiments, the first electrode is located on a structure (e.g., structure 308) that is positioned in the bodily cavity (e.g., left atrium 204) in a deployed configuration (e.g., a deployed configuration such as shown in FIGS. 3B, 3C and 3D). In various embodiments, energy sufficient for tissue ablation is transmittable by the first electrode, at least some of the energy transmittable to adjacent tissue of a tissue wall of the bodily cavity. In various embodiments, the energy transmittable by the first electrode is sufficient for tissue ablation. (It should be recalled, however, that the detection of the particular condition according to the instructions associated with block 506 may occur based on energy transmitted at levels insufficient for tissue ablation. Accordingly, when detecting the particular condition, the electric field lines illustrated in FIGS. 6G, 6H, and 6I (as well as the other figures of FIG. 6), discussed above, may represent energy insufficient for tissue ablation, according to some embodiments. However, the electric field lines illustrated in FIG. 6, discussed below, may alternatively represent tissue-ablative energy and, in that case, particular conditions to be avoided, according to some embodiments.) Again, the first non-tissue based electrically conductive surface can form part of any number of different devices as described above in this disclosure. In various embodiments, the target distance between the first non-tissue based electrically conductive surface and the first electrode may be associated with a configuration in which the structure on which the first electrode is located is in a deployed configuration.

In some embodiments, the target distance may be predetermined based on previous testing to identify the minimum distance between the first electrode (e.g., 615-3a in FIG. 6H) and the first non-tissue based electrically conductive surface (e.g., 630-3 in FIG. 6H) that allows for proper energy transmission by the first electrode, e.g., to allow for proper ablation or other functioning. In some embodiments, the target distance is a distance between the first electrode and the first non-tissue based electrically conductive surface required to reduce occurrences of a shunt condition, the shunt condition associated with a portion of the energy (e.g., electric current) transmittable by the first electrode being improperly diverted to the first non-tissue based electrically conductive surface. In some embodiments, the target distance is determined to be sufficient to limit at least some of the energy that is transmittable from the first electrode to blood to have a magnitude insufficient for thermal coagulation of the blood. For example, as shown in FIG. 6G, the first electrode 615-3a is sufficiently spaced from a respective one of the first non-tissue based electrically conductive surface 630-3 by a target distance 629 that is sufficient to avoid the shunt condition shown in corresponding FIGS. 6H and 6I. It is noted in some embodiments, that when a shunted condition is not present, a distance between the first electrode and the first non-tissue based electrically conductive surface may be greater than an associated target distance when a structure on which the first electrode in located is in a deployed configuration. In these embodiments, the target distance may be interpreted as a minimum desirable distance between the first electrode and the first non-tissue based electrically conductive surface when the structure is in the deployed configuration. In some embodiments, this target distance is 0.8 mm between the most adjacent electrically conductive surface portions (e.g., most-adjacent-edge-to-most-adjacent-edge or most most-adjacent-surface-to-most-adjacent-surface) of the first electrode and the first non-tissue based electrically conductive surface when the structure is in the deployed configuration. In various embodiments, different target distances may be associated with different first electrodes, different first non-tissue based electrically conductive surfaces, or combinations thereof.

Various methods may be employed to detect, determine or characterize a distance between the first electrode and the first non-tissue based electrically conductive surface, including various imaging methods. In some embodiments, electrical impedance based detection/determination methods are employed to detect a distance between the first electrode and the first non-tissue based electrically conductive surface. It is noted that, in some of the embodiments described with respect to FIGS. 6A, 6B, 6C, 6D, 6E, 6F, 6G, 6H and 6I, each of various ones of the structural members 604-1a, 604-1b, 604-2a, 604-2b, 604-2c, 604-3a and 604-3b may include different material compositions including various combinations of electrically insulative and electrically conductive materials (e.g., an assemblage of electrically insulative and electrically conductive material layers like that shown, e.g., with respect to FIG. 4). In some embodiments, an electrically insulative material is disposed between an electrically conductive portion of various ones of the structural members 604-1a, 604-1b, 604-2a, 604-2b, 604-2c, 604-3a and 604-3b and an associated one of the electrodes 615-1a, 615-1b, 615-2a, 615-2b, 615-2c, 615-3a, and 615-3b. It is noted that various ones of the sectioned elements depicted in FIGS. 6A, 6B, 6C, 6D, 6E, 6F, 6G, 6H and 6I need not represent a single material composition.

Figure 7:
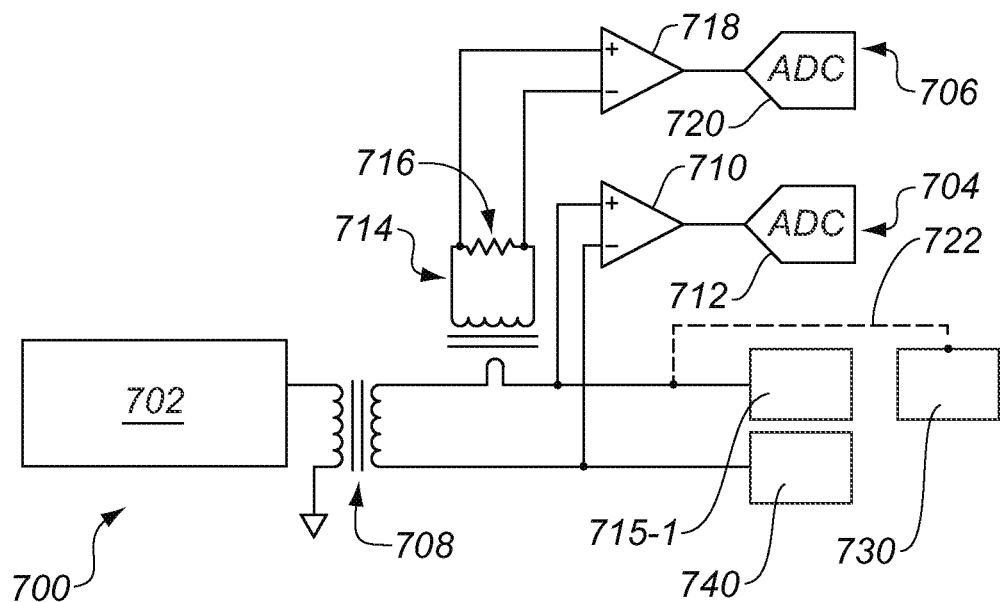
FIG. 7 is a block diagram of an electric circuit configured to determine an electrical impedance between various objects, according to some embodiments.

FIG. 7 is a schematic block diagram of an electric circuit 700 that is configured to determine electrical impedance (e.g., RF impedance) between various objects according to various embodiments. Such a circuit 700 may be incorporated into the medical device system of FIG. 1, 3A, or 3B, or more particularly, into an electrode-based device system (e.g., 200 or 300), and may provide information according to block 502A or 502B.

In various embodiments, electric circuit 700 includes a radio-frequency (RF) driver 702 and respective RF driver voltage and RF driver current sensing circuits 704 and 706. In FIG. 7, voltage can be sensed using an amplifier 710 and analog to digital converter (ADC) 712. Current can be sensed using a current sense transformer 714 with a sense resistor 716 (e.g., a 1:100 current sense transformer with a sense resistor). The voltage across the sense resistor 716 is amplified via amplifier 718 and sampled using an ADC 720. The signals can be sampled using sequential sampling to reconstruct the RF waveform. The RF current and voltage waveforms can then be demodulated into the in-phase and quadrature-phase components. From these components, the complex impedance of the load can be calculated. In some embodiments, sampled waveforms are used to calculate the power delivered to the load.

In various embodiments, electrical impedance (e.g., RF impedance) is determined between (a) either a first electrode 715-1 (e.g., a first electrode 315, 415, 615-1a, 615-2a, or 615-3a) or a first non-tissue based electrically conductive surface 730, and (b) a second non-tissue based electrically conductive surface 740. In some embodiments, the first non-tissue based electrically conductive surface 730 is a surface of a second electrode (other than the first electrode 715-1), and this second electrode may be located on the same structure (e.g., 308) on which the first electrode 715-1 is located. In some embodiments, the second non-tissue based electrically conductive surface 740 is a surface of a third electrode (other than the first electrode 715-1 and the second electrode), and this third electrode may be located on a structure that may also support the first electrode 715-1, the second electrode, or both the first electrode 715-1 and the second electrode. In some embodiments, the second non-tissue based electrically conductive surface 740 is arranged to be positioned outside of a bodily cavity in which the first electrode 715-1 is positioned. In some embodiments, the second non-tissue based electrically conductive surface 740 is arranged to be positioned inside a bodily cavity in which the first electrode 715-1 is positioned. In some embodiments, the second non-tissue based electrically conductive surface 740 is a surface of an indifferent electrode (e.g., indifferent electrode 326, 626a or 626b). In some embodiments in which electrical impedance (e.g., RF impedance) is determined between the first electrode 715-1 and the second non-tissue based electrically conductive surface 740, the second non-tissue based electrically conductive surface 740 forms part of or is a surface of a second electrode (other than the first electrode 715-1) positionable in the bodily cavity. In some embodiments, this second electrode is located on the same structure (e.g., 308) on which the first electrode 715-1 is located. In some example embodiments, the second non-tissue based electrically conductive surface 740 is part of a non-electrode portion of an electrode-based device system (e.g., 200 or 300), the electrode-based device system including the first electrode 715-1. For example, the second non-tissue based electrically conductive surface 740 may be a non-electrode portion of a structure (the first electrode 715-1 also being located on the structure), the non-electrode portion appropriately communicatively connected to the circuit 700 for the impedance determination.

In various embodiments, electrical impedance (e.g., RF impedance) is detected to assess whether the first electrode 715-1 is in contact with non-fluidic tissue (e.g., cardiac tissue) forming a surface of a bodily cavity in which the first electrode 715-1 is located or whether the first electrode 715-1 is in contact with fluidic tissue (e.g., blood) in the bodily cavity. For example, fluidic tissue such as blood typically has higher conductivity than non-fluidic tissue such as cardiac tissue. Accordingly, when the first electrode 715-1 is in contact with blood, the electrical impedance will be lower than when the first electrode 715-1 is in contact with the cardiac tissue (i.e., tissue forming part of a cardiac tissue wall). Partial contact with blood and cardiac tissue may lead to intermediate impedance readings. In addition, as noted above in this disclosure, the proximity of a first non-tissue based electrically conductive surface to a first electrode can affect a flow of electrical current and impedance readings between the first electrode and a second non-tissue based electrically conductive surface such as an indifferent electrode or a second electrode located on a structure on which the first electrode is located.

FIG. 5H includes an exploded view of blocks 504 and 506 as employed in various embodiments. In this regard, block 506 may include a block 506G whose associated instructions are configured to cause a detection of a particular condition based on an analysis of the information acquired according to the acquisition instructions associated with block 504, the particular condition being a proximity condition indicating or defined to indicate proximity between a first non-tissue based electrically conductive surface (e.g., first non-tissue based electrically conductive surface 730) positionable in a bodily cavity and the first electrode (e.g., first electrode 715-1) also positionable in the bodily cavity. The proximity, as with any other discussion of proximity with respect to the detection of at least the proximity condition of block 506G, in some embodiments, may also be referred to as an improper proximity. In some embodiments, the proximity may include contact. In some embodiments, the proximity condition indicates or is defined to indicate a proximity between a first non-tissue based electrically conductive surface (e.g., first non-tissue based electrically conductive surface 730) positionable in a bodily cavity and the first electrode (e.g., first electrode 715-1) also positionable in the bodily cavity when the first non-tissue based electrically conductive surface, the first electrode, or each of the first non-tissue based electrically conductive surface and the first electrode contacts a surface of a tissue wall of the bodily cavity. In some embodiments, the first electrode may be located on a structure (e.g., structure 308) which is in a deployed configuration.

In this regard, it may be beneficial in some embodiments to detect or determine a proximity between an electrode (e.g., 315-1a and FIGS. 3D and 3E; an example of the first electrode) and a non-electrode, metallic or otherwise electrically conductive portion of an elongate member (e.g., 304d in FIGS. 3D and 3E; an example of the first non-tissue based electrically conductive surface), so that the improper proximity condition illustrated in FIG. 3E may be detected.

In various embodiments, a particular electrical impedance between the first electrode (e.g., 715-1) and a second non-tissue based electrically conductive surface (e.g., 740) or changes or variances in the electrical impedance between the first electrode (e.g., 715-1) and the second non-tissue based electrically conductive surface (e.g., 740), may be used, at least in part, to detect or characterize proximity between the first electrode (e.g., 715-1) and the first non-tissue based electrically conductive surface (e.g., 730). It is noted that in some embodiments, a particular electrical impedance between the first non-tissue based electrically conductive surface (e.g., 730) and the second non-tissue based electrically conductive surface (e.g., 740), or changes or variances in the electrical impedance between the first non-tissue based electrically conductive surface (e.g., 730) and the second non-tissue based electrically conductive surface (e.g., 740), may be used, at least in part, to detect or characterize proximity between the first electrode (e.g., 715-1) and the first non-tissue based electrically conductive surface (e.g., 730).

For example, in FIG. 5H, block 504 may include a block 504G-1 whose associated instructions include acquisition instructions configured to acquire first information or a derivative of the first information stored in the memory device system according to the storage instructions associated with block 503. In some of these embodiments, the first information or the derivative thereof is indicative of an electrical impedance between (a) either the first electrode (e.g., 715-1) or the first non-tissue based electrically conductive surface (e.g., 730) and (b) a second non-tissue based electrically conductive surface (e.g., 740), the second non-tissue based electrically conductive surface being other than the first non-tissue based electrically conductive surface, and the second non-tissue based electrically conductive surface not forming part of the first electrode. For example, electrical impedance may be detected between the first non-tissue based electrically conductive surface 730 and the second non-tissue based electrically conductive surface 740 by communicatively connecting (via electrical path 722 (shown in broken lines)) the first non-tissue based electrically conductive surface 730 to transformer 708 instead of communicatively connecting first electrode 715-1 to transformer 708.

In some embodiments, the first information or the derivative thereof is indicative of an electrical impedance between the first electrode (e.g., first electrode 715-1 or 615-3a) and a second non-tissue based electrically conductive surface (e.g., 740 or a surface of indifferent electrode 626b) that is different or other than a first non-tissue based electrically conductive surface (e.g., provided by structural member 604-3b). If the electrical impedance is lower than a target electrical impedance between the first electrode and the second non-tissue based electrically conductive surface, the instructions associated with block 506G may be configured to detect a proximity condition in which the first electrode and the first non-tissue based electrically conductive surface are insufficiently spaced or improperly in contact with respect to one another, (e.g., the positioning between the first electrode and the first non-tissue based electrically conductive surface may be a cause of the unexpectedly low impedance). It should be noted that the instructions associated with block 506F in FIG. 5G may also use such first information, when it indicates an electrical impedance lower than the target electrical impedance, to detect a condition in which the first electrode and the first non-tissue based electrically conductive surface are within a target distance of each other.

As discussed above, it may be beneficial in some embodiments to detect or determine a proximity between a first electrode (e.g., 315-1a and FIGS. 3D and 3E) and a non-electrode, metallic portion of an elongate member (e.g., 304d in FIGS. 3D and 3E; an example of the first non-tissue based electrically conductive surface), so that the improper proximity condition illustrated in FIG. 3E may be detected. In some of these embodiments, this proximity condition (e.g., FIG. 3E) is detected based at least on an analysis of an electrical impedance between (a) either the first electrode (e.g., 315-1a and FIGS. 3D and 3E) or the non-electrode, metallic portion of the elongate member (e.g., 304d in FIGS. 3D and 3E; an example of the first non-tissue based electrically conductive surface) and (b) a second non-tissue based electrically conductive surface. In some of these embodiments, the second non-tissue based electrically conductive surface is other than the non-electrode, metallic portion of the elongate member, and the second non-tissue based electrically conductive surface does not form part of the first electrode.

In this regard, it should be noted that the electrical impedance need not measured between the two objects for which proximity is being detected. For example, to determine a proximity between a first electrode (e.g., 315-1a and FIGS. 3D and 3E) and a first non-tissue based electrically conductive surface exemplified in some embodiments by a non-electrode, metallic portion of an elongate member (e.g., 304d in FIGS. 3D and 3E), electrical impedance need not be measured between the first electrode and the non-electrode, metallic portion of the elongate member (i.e., an example of the first non-tissue based electrically conductive surface). Instead, the electrical impedance may be measured between (a) either the first electrode or the non-electrode, metallic portion of the elongate member (i.e., an example of the first non-tissue based electrically conductive surface) and (b) some other non-tissue based electrically conductive surface, such as a different electrode or an indifferent electrode. If the measured electrical impedance between (a) and (b) is lower than a target or expected impedance, the improper proximity condition (e.g., FIG. 3E) may be detected without the need to measure electrical impedance between the two objects for which proximity is being detected.

Figure 9:
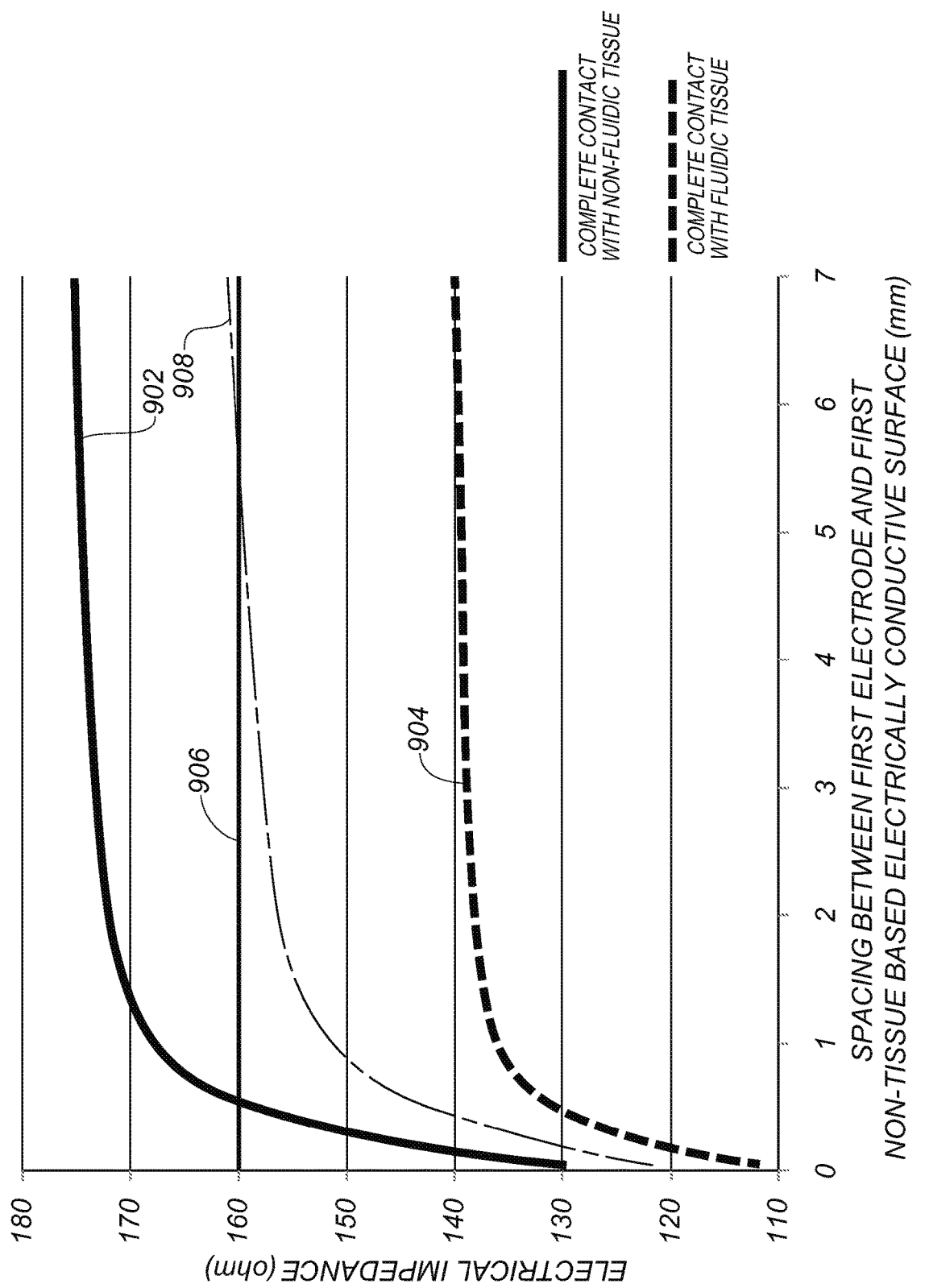
FIG. 9 illustrates various graphs of electrical impedance as a function of a spacing between a first electrode and a first non-tissue based electrically conductive surface, according to some embodiments.

FIG. 9 includes graphs 902, 904, each representing electrical impedance between a first electrode and a second non-tissue based electrically conductive surface. The electrical impedance in each graph varies as a function of a distance or spacing between the first electrode and a first non-tissue based electrically conductive surface that is different than the second non-tissue based electrically conductive surface. Each graph was generated using data generated by Multiphysics® 4.1, Version 4.1.0.88 software provided by Comsol Inc. The modeled first electrode was representative of an essentially planar electrode structure (e.g., electrode 315, 415). The modelled first non-tissue based electrically conductive surface was representative of a structural member similar to elongate member 304, the structural member including an electrically conductive bottom layer and an electrically insulative top layer. The modelled second non-tissue based electrically conductive surface was representative of an electrically conductive surface positioned approximate 100 mm from the first non-tissue based electrically conductive surface. Modelled non-fluidic tissue was representative of myocardial tissue (i.e., a conductivity of 0.5 S/m was employed). Modeled fluidic tissue was representative of blood (i.e., a conductivity of 0.75 S/m was employed).

Graph 902 is representative of a case in which the entirety of the electrically conductive surface portion (e.g., an energy transmission surface 319) of the first electrode is in contact with non-fluidic tissue (e.g., modeled as cardiac tissue forming a tissue wall) and graph 904 is representative of a case in which the entirety of the electrically conductive surface portion of the first electrode is in contact with fluidic tissue (e.g., modeled as blood). It is appreciated that various other graphs representative of partial contact between the electrically conductive surface portion of the first electrode and the non-fluidic tissue (or between the electrically conductive surface portion of the first electrode and the fluidic tissue) may be provided between graphs 902 and 904. The electrical impedances associated with graph 902 (i.e., complete contact with cardiac tissue) are greater than the electrical impedances associated with graph 904 (i.e., complete contact with blood) for a given distance or spacing between the first electrode and the first non-tissue based electrically conductive surface. The electrical impedances associated with each of the graphs 902 and 904 fall as the spacing between the first electrode and the first non-tissue based electrically conductive surface becomes smaller. In the case of graph 902, relatively smaller distances or spacings between the first electrode and the first non-tissue based electrically conductive surface may be associated with electrical impedances having values low enough to lead to a shunt condition as described above in this disclosure. Line 906 represents a target electrical impedance that may be used according to some embodiments (e.g., a target impedance may be set 10% below a maximum electrical impedance indicated on graph 902). In FIG. 9, the target electrical impedance is set to 160 ohms. In some embodiments, the target electrical impedance is related to the target distance associated with block 506F of FIG. 5G.

Electrical impedance values below that target impedance value indicated by line 906 may be employed in various embodiments to determine various conditions such as a shunt condition, a condition indicating a distance or spacing between the first electrode and the first non-tissue based electrically conductive surface or various other conditions (e.g., as described above in this disclosure), especially when complete contact between an electrically conductive surface portion of the first electrode and the non-fluidic tissue is known to exist. In some embodiments however, a particular contact condition between the electrically conductive surface portion of the first electrode and the non-fluidic tissue may not be known. In FIG. 9, graph 908 is representative of a case in which some, but not all, of the electrically conductive surface portion of the first electrode is in contact with the non-fluidic tissue. Graph 908 was not modeled using the software provided by Comsol Inc., but rather was added for the convenience of discussion. If an electrical impedance value of 150 ohms was determined to exist between the first electrode and the second non-tissue based electrically conductive surface, various conclusions may be arrived at. For example, a determined impedance value of 150 ohms would be less than the target electrical impedance value (e.g., 160 ohms) indicating that a shunt condition likely exists. Alternatively, a determined impedance value of 150 ohms may also indicate a condition in which some, but not all, of the electrically conductive surface portion of the first electrode is in contact with the non-fluidic tissue. In either case, when the first electrode is operable for transmitting tissue ablation energy, undesired thermal coagulation of blood may result. If an electrical impedance value of 135 ohms was determined to exist between the first electrode and the second non-tissue based electrically conductive surface, various conclusions may be arrived at. For example, a determined impedance value of 135 ohms would be less than the target electrical impedance value (e.g., 160 ohms) indicating that a shunt condition likely exists. Alternatively, a determined impedance value of 135 ohms may also indicate a condition in which some amount (even possibly all) of the electrically conductive surface portion of the first electrode is in contact with the fluidic tissue (e.g., blood). The formation of thermal coagulum may result in either case if the first electrode transmits tissue ablation energy.

Referring back to FIG. 5H, block 504 may include a block 504G-2 that may be employed in some embodiments. The instructions associated with block 504G-2 include acquisition instructions configured to acquire second information. In some embodiments, the second information or a derivative thereof stored in the memory device system according to the storage instructions associated with block 503. In some embodiments, the second information is different than the first information acquired according to the instructions associated with block 504G-1. In some embodiments, the second information is indicative of a proximity between the first electrode and non-fluidic tissue (e.g., tissue making up a tissue wall of the bodily cavity). In some of these embodiments, the second information is indicative of an amount of contact between the first electrode and the non-fluidic tissue. As previously indicated, varying amounts of an electrically conductive surface portion of the first electrode may be available or exposed (e.g., without some obstruction preventing at least some of the ability) to contact or may actually make contact with a non-fluidic tissue surface in various embodiments. In this regard, the second information may indicate the amount of contact that exists between the first electrode and the non-fluidic tissue. In some embodiments, the detection instructions associated with block 506G are configured to cause a data processing device system (e.g., 110) to detect the proximity condition (between the first electrode and the first non-tissue-based electrically conductive surface) based at least on the first information acquired in block 504G-1 as discussed above. In some embodiments, the detection instructions of block 506G are configured to cause a data processing device system (e.g., 110) to detect the proximity condition based at least on a combination of the first information acquired in accordance with block 504G-1 and the second information acquired in accordance with block 504G-2. In this regard, a deviation from an expected amount of non-fluidic-tissue-contact that an electrode experiences may indicate that something is obstructing the surface of the electrode, such as shown in FIG. 3E. However, since unexpected partial or no contact with non-fluidic tissue can be caused by other reasons, besides obstruction by another part of an electrode-based device system, it may be helpful in some embodiments for the second information to include fluid flow (e.g., flow sensing) information, convective heat information, or temperature information to facilitate a determination of whether, for example, unexpected partial or no non-fluidic tissue contact is due to obstruction from another part of an electrode-based device system or is due, e.g., to the electrode being all or partially exposed to a port (instead of fully contacting non-fluidic tissue) that interrupts a tissue wall in a bodily cavity. Accordingly, in some embodiments, where the proximity condition associated with block 506G is detected based at least on a combination of the first information and the second information, a data processing device system (e.g., 110) may be configured to determine based on an analysis of the first information and the second information whether such information indicates a proximity between the first electrode and the first non-tissue based electrically conductive surface or indicates an amount of contact that exists between and electrically conductive surface portion of the first electrode and a non-fluidic tissue surface (e.g., tissue forming a tissue wall) or fluidic tissue (e.g., blood).

Figure 8:
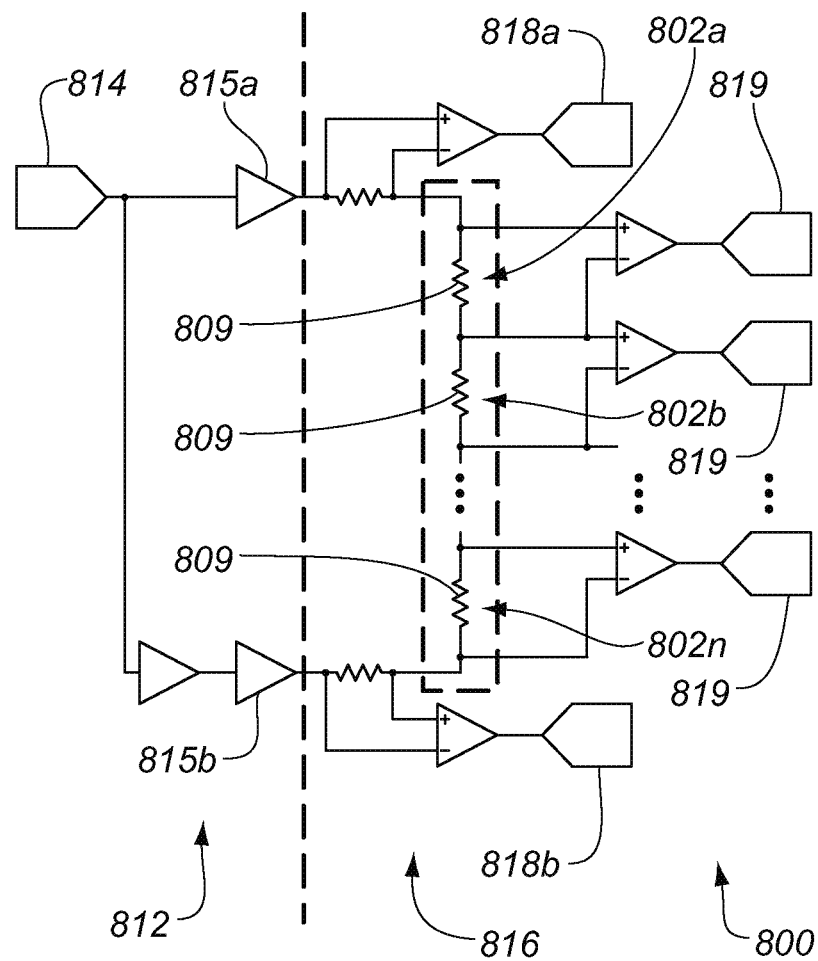
FIG. 8 is a block diagram of an electrical circuit configured to determine an electrical resistance of various resistive members employed by various transducer elements, according to some example embodiments.

In this regard, various methods and systems may be used to detect an amount of an electrically conductive surface portion of an electrode that contacts non-fluidic tissue or contacts fluidic tissue. FIG. 8 is a block diagram of an electrical circuit 800 that is configured to detect an amount of an electrically conductive surface portion of an electrode that contacts non-fluidic tissue or contacts fluidic tissue, according to some embodiments. Such a circuit 800 may be incorporated into the medical device system of FIG. 1, 3A, or 3B, or more particularly, into an electrode-based device system (e.g., 200 or 300), and may provide information (e.g., at least part of second information referred to in block 504G-2) according to block 502A or 502B. Electrical circuit 800 is configured, according to some embodiments, to determine an electrical resistance of various resistive members 809 employed by various transducers (e.g., FIG. 4) 802a, 802b, . . . 802n (collectively 802) which may be positioned in a bodily cavity (e.g., left atrium 204) having one or more ports (e.g., pulmonary vein ostiums (not shown) or a mitral valve 226) in fluid communication with the bodily cavity. In some embodiments, a portion (e.g., an electrode surface or a portion thereof) of a first transducer may be positioned in contact with non-fluidic tissue (e.g., cardiac tissue) while a portion (e.g., an electrode surface or a portion thereof) of a second transducer 802 may be in contact with fluidic tissue (e.g., blood). The number of transducers 802 employed may vary in different embodiments.

Each resistive member 809 may be formed from copper traces on a flexible printed circuit board substrate (e.g., resistive members 409), or resistive elements provided on a structure. Each transducer 802 is driven by a state machine (not shown) within a controller (e.g., controller 324), according to some embodiments. In various embodiments, electrical circuit 800 includes a signal source device system 812 and a sensing device system 816, each schematically distinguished from one another by a broken line in FIG. 8. It is understood that one or both of signal source device system 812 and sensing device system 816 may each include different circuitry than those shown in FIG. 8.

In various embodiments, signal source device system 812 provides various input signals to at least some of the transducers 802 during a temperature sensing mode. In some embodiments, signal source device system 812 provides various input signals to at least some of the transducers 802 during a flow sensing mode. In some example embodiments, signal source device system 812 provides various input signals to each of the transducers 802 during a mapping mode in which information specifying a location of various anatomical features within a bodily cavity is provided. For example, information specifying a location of each of one or more regions of an interior tissue surface within a bodily cavity may be provided along with information specifying a location of each of at least one of one or more ports on the interior tissue wall with respect to the one or more regions during the mapping mode. In some example embodiments, signal source device system 812 provides various input signals to each of the transducers 802 during a tissue contact mode in which contact or an amount of contact between a portion (e.g., an electrically conductive surface portion of an electrode) of each of the various transducers 802 and non-fluidic tissue or a fluidic tissue is made. In some example embodiments, signal source device system 812 provides various input signals during an ablation mode. In some example embodiments, a state machine (not shown) in the controller may be employed to cause various control signals (not shown) to be provided to signal source device system 812 to configure electrical circuit 800 in at least one of a temperature sensing mode and a flow sensing mode. In some example embodiments, signal source device system 812 includes a radio-frequency generator (not shown) configured to transfer energy to, or from, the tissue wall. In some example embodiments, the radio-frequency generator (not shown) is arranged to provide a varying electrical current to at least one of the transducers 802 to provide energy to tissue from the at least one of the transducers 802.

In various embodiments, digital-to-analog converter (DAC) 814 generates an input signal that is amplified and is driven across the series of the connected resistive members 809 during a temperature sensing mode. Amplifiers including driver 815a and driver 815b are arranged to produce a balanced output across the series of connected resistive members 809. Electrical current driven through resistive members 809 is sampled by sensing device system 816. In this example embodiment, electrical current driven through resistive members 809 is sampled at each of the drivers 815a, 815b via respective ones of analog-to-digital converters (ADC) 818a, 818b. It is noted that sensing the electrical current at each of the drivers 815a, 815b can allow the system to detect possible failures that may result in the electrical current leaking through another path. Voltage across each of the resistive members 809 is also sampled by sensing device system 816 via respective ones of analog-to-digital converters (ADC) 819 (three called out in FIG. 8). In some embodiments, the current and voltage measurements are sampled synchronously with the input signal and the demodulation of each measurement is computed by the controller. Electrical circuit 800 allows for the electrical resistance of each of the resistive members 809 to be precisely determined. The resistance of an electrically conductive metal (e.g., copper) changes based on the temperature of the electrically conductive metal. The rate of change is denominated as a temperature coefficient of resistance (TCR). The resistance of various ones of the resistive members 809 may be related to the temperature of the resistive member 809 by the following relationship:

$$R = R_0 * [1 + TCR * (T - T_0)], \text{ where:}$$

R is a resistance of the electrically conductive metal at a temperature T;

$R_0$ is a resistance of the electrically conductive metal at a reference temperature $T_0$;

TCR is the temperature coefficient of resistance for the reference temperature (i.e., the TCR for copper is 4270 ppm at $T_0 = 0°$ C.); and T is the temperature of the electrically conductive metal.

When signal source device system 812 applies energy to a resistive element (e.g., resistive member 809 employed by various transducers 802) positioned within a medium having relatively high flow conditions (for example, when subjected to blood flow conditions proximate a pulmonary vein port in the left atrium of a heart or when not shielded from the flow by contact with non-fluidic tissue), the resistive element will heat to a lower temperature and will settle more quickly than if the resistive element were positioned within a medium having relatively low flow conditions (for example when positioned proximate, or in contact with a region of a non-fluidic tissue surface within a left atrium positioned away from the pulmonary vein port). Likewise, when the signal source ceases to apply energy, the resistive element positioned within a medium having relatively high flow conditions will cool faster and will return to ambient temperature faster than if the resistive element were to be within a medium having relatively lower flow conditions. When the signal source repetitively applies and ceases to apply energy to the resistive element, the resulting temperature changes of the resistive element positioned in a medium having relatively low flow conditions will appear to have a phase delay compared to the resulting temperature changes of the resistive element when positioned in a medium having relatively higher flow conditions.

In various embodiments, flow sensing is provided by electrical circuit 800 by determining the rate of convective cooling at various ones of the resistive members 809. In some embodiments, when the flow sensing mode is enabled, various ones of the resistive members 809 whose temperature is determined during the temperature sensing mode can also be employed to deliver energy (i.e., heat) during the flow sensing mode. In various embodiments, the energy is delivered using the same drivers 815a, 815b employed in the temperature sensing mode. It is understood that additional and or alternate drivers may be employed in other example embodiments but with additional cost and complexity. When the temperature sensing mode is not active, the controller system may continue to drive an input signal to each of the resistive members 809 in various embodiments.

In various embodiments in which the plurality of transducers 802 are arranged within a bodily cavity (e.g., an intra-cardiac cavity such as a left atrium) having various internal anatomical features, the controller can provide information specifying a location of at least one of the internal anatomical features within the bodily cavity based at least in part on the flow sensing information. As an example, the plurality of transducers 802 may be arranged within a bodily cavity (e.g., an intra-cardiac cavity such as a left atrium 204) defined at least in part by a tissue wall having an interior tissue surface interrupted by one or more ports in fluid communication with the bodily cavity (e.g., pulmonary veins). In such an example, the controller system can provide information specifying a location of each of one or more regions of the interior tissue surface and a location of at least one of the one or more ports on the interior tissue surface with respect to the one or more regions based on the flow sensing information. Additionally or alternatively, in some embodiments, contact or an amount of contact between a portion of a particular transducer 802 (e.g., an electrode surface) and non-fluidic tissue or fluidic tissue may be determined based at least in part on the flow sensing information.

Although the above disclosure often is described in the context of 'transmittable energy' to emphasize a typical desire to detect potentially improper energy delivery conditions before energy is delivered, it should be noted that some embodiments are not limited to this context and some embodiments pertain to the detection of the particular conditions (e.g., block 506) during energy delivery. In this regard, in some embodiments, the above-discussed context of 'transmittable energy' may be replaced with the context of 'energy that is or is being transmitted' or the like to pertain to detection of conditions during energy delivery.

Further, the above disclosure describes various techniques for detecting various particular conditions (e.g., block 506), and some of these techniques are described within a context of detecting one or more particular conditions. However, it should be noted that any of the techniques for detecting a condition may be used to detect any of the other conditions discussed above. For example, the techniques for detecting a shunt condition (e.g., FIG. 5E) may be used to detect contact between a non-tissue based surface and an electrically conductive surface portion of an electrode (e.g., FIG. 5D), to detect a condition where some, but not all, of an electrically conductive surface portion of an electrode is available or exposed (e.g., without some obstruction preventing at least some of the ability) for tissue contact (e.g., FIG. 5C), to detect a deviation in an expected positioning of at least a portion of an electrode-based device system (e.g., FIGS. 5B and 5F), to detect a condition indicating a distance between a first non-tissue based electrically conductive surface and a first electrode is less than a target distance (e.g., FIG. 5G), or a combination thereof, because detecting a shunt condition involving an electrode of an electrode-based device system can indicate all of such conditions. In this regard, it should be noted that any of the techniques for detecting a condition pursuant to FIGS. 5A-5H may be used to detect any of the other conditions of FIGS. 5A-5H.

Further still, it should be noted that an electrode-based device system need not take the respective forms shown by electrode-based device system 200 or electrode-based device system 300, and that any form of electrode-based device system may be used in which a condition discussed above may be detected, whether such electrode-based device system includes electrodes of the configuration shown in FIG. 4 or otherwise.

While some of the embodiments disclosed above are described with examples of cardiac ablation, the same or similar embodiments may be used for ablating other bodily organs or any lumen or cavity into which the devices of the present invention may be introduced.

While some embodiments disclosed herein pertain to the data processing device system 110 detecting one or more particular conditions according to instructions associated with block 506 and thereafter restricting energy transmission according to instructions associated with block 510 or presenting an error notification according to instructions associated with block 512, other embodiments are not so limited. For example, in some embodiments, the data processing device system 110 may cause the input-output device system 120 to present some or all of the information received according to the instructions associated with block 502A and 502B to a user, and the user may detect the one or more particular conditions based on a review of that presented information. In this regard, in some embodiments, the user or some other user may choose to avoid, restrict, or permit energy transmission by one or more electrodes of the medical device system of, e.g., FIG. 2 or FIG. 3, based on a user determination of existence (or non-existence) of one or more of the particular conditions based on the review of the presented information.

Subsets or combinations of various embodiments described above provide further embodiments.

These and other changes can be made to various embodiments in light of the above-detailed description. In general, in the following claims, the terms used should not be construed to limit the invention to the specific embodiments disclosed in the specification and the claims, but should be construed to include other electrode-based device systems including all medical treatment device systems and all medical diagnostic device systems in accordance with the claims. Further, it should be noted that, although several of the above-discussed embodiments are described within the context of an intra-cardiac medical device system, other embodiments apply to other medical and non-medical device systems, such as an device system in which detecting one or more improper energy transmission configurations is beneficial. Accordingly, the invention is not limited by this disclosure, but instead its scope is to be determined entirely by the claims.

What is claimed is:

1. A medical device system comprising:
   a data processing device system; and
   a memory device system communicatively connected to the data processing device system and storing a program executable by the data processing device system, the program comprising:
   acquisition instructions configured to cause an acquisition of information stored in the memory device system;
   detection instructions configured to cause a detection of an obstruction condition, based at least upon an analysis of the information acquired according to the acquisition instructions, the obstruction condition indicating that some, but not all, of a respective electrically conductive surface portion of each of at least a first electrode of one or more electrodes is obstructed and unavailable to contact tissue of a tissue wall of a bodily cavity when a structure, on which each of the one or more electrodes is located, is positioned in the bodily cavity in a deployed configuration, the obstruction condition associated with contact between a non-tissue based surface positioned in the bodily cavity and the electrically conductive surface portion of the first electrode of the one or more electrodes when the structure is positioned in the bodily cavity in the deployed configuration, the deployed configuration being different than a delivery configuration in which the structure is sized for percutaneous delivery to the bodily cavity, the entirety of the respective electrically conductive surface portion of each of at least the first electrode of the one or more electrodes configured, in absence of the obstruction condition, to contact a contiguous surface portion of the tissue wall when the structure is positioned in the bodily cavity in the deployed configuration, and for each respective electrically conductive surface portion, energy is transmittable between the respective electrically conductive surface portion and the tissue wall, the energy sufficient for tissue ablation; and
   storage instructions configured to cause a storage in the memory device system of detection information indicating the detection of the obstruction condition according to the detection instructions.

2. The medical device system of claim 1, further comprising an electrode-based device system communicatively connected to the data processing device system, the electrode-based device system comprising the structure and the one or more electrodes located on the structure, the structure selectively movable between the delivery configuration and the deployed configuration.

3. The medical device system of claim 2, further comprising an input-output device system communicatively connected to the data processing device system, the input-output device system comprising the electrode-based device system,
   wherein the program further comprises reception instructions configured to cause (a) a reception of first information from the electrode-based device system, and (b) a storage of the first information or a derivative thereof in the memory device system, and
   wherein the information acquired according to the acquisition instructions is the first information or the derivative of the first information stored in the memory device system according to the reception instructions.

4. The medical device system of claim 3
   wherein the electrode-based device system includes one or more transducers, the one or more transducers configured to, while positioned in the bodily cavity, provide one or more electrical signals to the tissue wall,
   wherein the first information or the derivative thereof indicates a result of an interaction between the one or more electrical signals and the tissue wall, and
   wherein the one or more electrical signals comprise one or more energy levels insufficient for tissue ablation.

5. The medical device system of claim 2 wherein the non-tissue based surface does not form part of any electrode.

6. The medical device system of claim 2 wherein the obstruction condition is associated with contact between the electrically conductive surface portion of the first electrode of the one or more electrodes and a portion of the structure when the structure is positioned in the bodily cavity in the deployed configuration.

7. The medical device system of claim 2 wherein the obstruction condition is associated with contact between a second electrode positioned in the bodily cavity and the electrically conductive surface portion of the first electrode of the one or more electrodes when the structure is positioned in the bodily cavity in the deployed configuration.

8. The medical device system of claim 2 wherein the one or more electrodes include a second electrode, and the obstruction condition is associated with contact between the electrically conductive surface portion of the first electrode of the one or more electrodes and the second electrode of the one or more electrodes when the structure is positioned in the bodily cavity in the deployed configuration.

9. The medical device system of claim 2 wherein at least part of the electrically conductive surface portion of the first electrode of the one or more electrodes is positioned to face towards a surface portion of the tissue wall when the structure is positioned in the bodily cavity in the deployed configuration, and the obstruction condition is associated with a positioning of a physical portion of the electrode-based device system between the electrically conductive surface portion of the first electrode of the one or more electrodes and the surface portion of the tissue wall when the structure is positioned in the bodily cavity in the deployed configuration.

10. The medical device system of claim 2 wherein at least part of the electrically conductive surface portion of the first electrode of the one or more electrodes is positioned to face towards a surface portion of the tissue wall when the structure is positioned in the bodily cavity in the deployed configuration, and the obstruction condition is associated with a positioning of a portion of the structure between the electrically conductive surface portion of the first electrode of the one or more electrodes and the surface portion of the tissue wall when the structure is positioned in the bodily cavity in the deployed configuration.

11. The medical device system of claim 2 wherein the information acquired according to the acquisition instructions includes positional information indicative of a deviation in an expected positioning between the first electrode of the one or more electrodes and a physical portion of the electrode-based device system when the structure is positioned in the bodily cavity in the deployed configuration.

12. The medical device system of claim 2
wherein the structure comprises one or more elongate members,
wherein the one or more electrodes comprise a plurality of the electrodes, at least some of the plurality of the electrodes located on each of the one or more elongate members,
wherein the first electrode of the one or more electrodes is located on a first elongate member of the one or more elongate members, and
wherein the information acquired according to the acquisition instructions includes positional information indicative of a deviation in an expected positioning between the first electrode of the one or more electrodes and an elongate member of the one or more elongate members when the structure is positioned in the bodily cavity in the deployed configuration.

13. The medical device system of claim 2
wherein the structure comprises a plurality of elongate members,
wherein the one or more electrodes comprise a plurality of the electrodes, at least some of the plurality of the electrodes located on each of the plurality of elongate members,
wherein the first electrode of the one or more electrodes is located on a first elongate member of the plurality of elongate members,
wherein the information acquired according to the acquisition instructions includes positional information indicative of a deviation in an expected positioning between the first electrode of the one or more electrodes and at least a second elongate member of the plurality of elongate members when the structure is positioned in the bodily cavity in the deployed configuration, and
wherein the first elongate member is other than the second elongate member.

14. The medical device system of claim 2
wherein the structure comprises a plurality of elongate members, each of the elongate members comprising a proximal end, a distal end, an intermediate portion positioned between the proximal end and the distal end, and a thickness, each intermediate portion comprising a front surface and a back surface opposite across the thickness of the elongate member from the front surface,
wherein the one or more electrodes comprise a plurality of the electrodes, at least some of the plurality of the electrodes located on each of the respective front surfaces of the plurality of elongate members,
wherein the first electrode of the one or more electrodes is located on the respective front surface of a first elongate member of the plurality of elongate members,
wherein the information acquired according to the acquisition instructions includes positional information indicative of positioning where at least part of the electrically conductive surface portion of the first electrode of the one or more electrodes faces the respective back surface of a second elongate member of the plurality of elongate members when the structure is positioned in the bodily cavity in the deployed configuration, and
wherein the first elongate member is other than the second elongate member.

15. The medical device system of claim 2 wherein the structure is sized too large for percutaneous delivery to the bodily cavity when the structure is in the deployed configuration.

16. The medical device system of claim 1, further comprising an input-output device system communicatively connected to the data processing device system, the input-output device system comprising a sensing device system,
wherein the program further comprises reception instructions configured to cause (a) a reception of first information from the sensing device system, and (b) a storage of the first information or a derivative thereof in the memory device system, and
wherein the information acquired according to the acquisition instructions is the first information or the derivative of the first information stored in the memory device system according to the reception instructions.

17. The medical device system of claim 1 wherein the program further comprises restriction instructions configured to cause a restriction of the energy transmittable by at least the first electrode of the one or more electrodes in response to the detected obstruction condition.

18. The medical device system of claim 1 wherein the program further comprises restriction instructions configured to prevent initiation of transmission of the energy transmittable by at least the first electrode of the one or more electrodes in response to the detected obstruction condition.

19. The medical device system of claim 1, further comprising an input-output device system communicatively connected to the data processing device system,
wherein the program further comprises failure state instructions configured to cause the input-output device system to present an error notification to a user in response to the detection of the obstruction condition according to the detection instructions.

20. The medical device system of claim 1 wherein the information acquired according to the acquisition instructions includes impedance information associated with at least the first electrode of the one or more electrodes.

21. A method executed by a data processing device system according to a program stored by a memory device system communicatively connected to the data processing device system, the method comprising:
- acquiring information stored in the memory device system;
- detecting an obstruction condition, based at least upon an analysis of the acquired information, the obstruction condition indicating that some, but not all, of a respective electrically conductive surface portion of each of at least a first electrode of one or more electrodes is obstructed and unavailable to contact tissue of a tissue wall of a bodily cavity when a structure, on which each of the one or more electrodes is located, is positioned in the bodily cavity in a deployed configuration, the obstruction condition associated with contact between a non-tissue based surface positioned in the bodily cavity and the electrically conductive surface portion of the first electrode of the one or more electrodes when the structure is positioned in the bodily cavity in the deployed configuration, the deployed configuration being different than a delivery configuration in which the structure is sized for percutaneous delivery to the bodily cavity, the entirety of the respective electrically conductive surface portion of each of at least the first electrode of the one or more electrodes configured, in absence of the obstruction condition, to contact a contiguous surface portion of the tissue wall when the structure is positioned in the bodily cavity in the deployed configuration, and for each respective electrically conductive surface portion, energy is transmittable between the respective electrically conductive surface portion and the tissue wall, the energy sufficient for tissue ablation; and
- storing in the memory device system of detection information indicating the detecting of the obstruction condition.

22. One or more non-transitory computer-readable storage mediums storing a program executable by one or more data processing devices of a data processing device system, the program comprising:
- acquisition instructions configured to cause an acquisition of information stored in the memory device system;
- detection instructions configured to cause a detection of an obstruction condition, based at least upon an analysis of the information acquired according to the acquisition instructions, the obstruction condition indicating that some, but not all, of a respective electrically conductive surface portion of each of at least a first electrode of one or more electrodes is obstructed and unavailable to contact tissue of a tissue wall of a bodily cavity when a structure, on which each of the one or more electrodes is located, is positioned in the bodily cavity in a deployed configuration, the obstruction condition associated with contact between a non-tissue based surface positioned in the bodily cavity and the electrically conductive surface portion of the first electrode of the one or more electrodes when the structure is positioned in the bodily cavity in the deployed configuration, the deployed configuration being different than a delivery configuration in which the structure is sized for percutaneous delivery to the bodily cavity, the entirety of the respective electrically conductive surface portion of each of at least the first electrode of the one or more electrodes configured, in absence of the obstruction condition, to contact a contiguous surface portion of the tissue wall when the structure is positioned in the bodily cavity in the deployed configuration, and for each respective electrically conductive surface portion, energy is transmittable between the respective electrically conductive surface portion and the tissue wall, the energy sufficient for tissue ablation; and
- storage instructions configured to cause a storage in the memory device system of detection information indicating the detection of the obstruction condition according to the detection instructions.

* * * * *